US007635722B1

(12) United States Patent
Bachynsky et al.

(10) Patent No.: US 7,635,722 B1
(45) Date of Patent: Dec. 22, 2009

(54) CHEMICAL INDUCED INTRACELLULAR HYPERTHERMIA

(75) Inventors: Nicholas Bachynsky, Parkland, FL (US); Woodie Roy, Parkland, FL (US)

(73) Assignee: Saint Jude Pharmaceuticals, Inc., Texarkana, TX (US)

( * ) Notice: Subject to any disclaimer, the term of this patent is extended or adjusted under 35 U.S.C. 154(b) by 0 days.

(21) Appl. No.: 09/744,622

(22) PCT Filed: Jul. 27, 1999

(86) PCT No.: PCT/US99/16940

§ 371 (c)(1),
(2), (4) Date: May 7, 2002

(87) PCT Pub. No.: WO00/06143

PCT Pub. Date: Feb. 10, 2000

Related U.S. Application Data

(60) Provisional application No. 60/094,286, filed on Jul. 27, 1998.

(51) Int. Cl.
*A01N 33/18* (2006.01)
*A01N 33/24* (2006.01)
*A61K 31/045* (2006.01)
*A61K 39/00* (2006.01)

(52) U.S. Cl. .................................. 514/728; 424/176.1
(58) Field of Classification Search ................. 514/728, 514/12; 424/176.1
See application file for complete search history.

(56) References Cited

U.S. PATENT DOCUMENTS

| | | | | |
|---|---|---|---|---|
| 4,337,760 A | * | 7/1982 | Rubin | 604/500 |
| 4,481,195 A | * | 11/1984 | Rubin | 514/25 |
| 4,555,397 A | | 11/1985 | Bachynsky | |
| 4,569,836 A | | 2/1986 | Gordon | |
| 4,673,691 A | | 6/1987 | Bachynsky | |
| 4,724,234 A | | 2/1988 | Cone, Jr. | |
| 5,005,588 A | * | 4/1991 | Rubin | 607/2 |
| 5,240,914 A | * | 8/1993 | Rubin | 514/23 |
| 5,340,803 A | * | 8/1994 | Rubin | 514/25 |
| 5,391,142 A | | 2/1995 | Sites et al. | |
| 5,434,163 A | | 7/1995 | Edlind et al. | |
| 5,476,842 A | * | 12/1995 | Rubin | 514/25 |
| 5,622,686 A | | 4/1997 | Gordon et al. | |
| 5,639,737 A | * | 6/1997 | Rubin | 514/53 |
| 5,674,190 A | | 10/1997 | Kelly | |
| 5,760,008 A | * | 6/1998 | Rubin | 514/25 |
| 6,090,788 A | * | 7/2000 | Lurie | 514/23 |

FOREIGN PATENT DOCUMENTS

WO    WO 97/05870 A2  *  2/1997

WO    WO-97/35540    10/1997

OTHER PUBLICATIONS

Kumar V. "Melatonin: A Master Hormone and a Candidate ofr Universal Panacea." Indian Journal of Experimental Biology. 1996; 34(5):391-402. (Abstract Only).*
Oka et al. "Immunosuppression in Organ Transplantation". Japanese Journal of Pharmacology. 1996; 71(2):89-100. (Abstract Only).*
Smith et al. "Hormone Replacement Therapy in the Menopause: A Pro Opinion". CA: A Cancer Journal for Clinicians. 1996; 46(6):343-363.(Abstract Only).*
Rickels et al. "The Clinical Presentation of Generalized Anxiety in Primary-Care Settings: Practical Concepts of Classification and Management". Journal of Clinical Psychiatry. 1997; 58 Suppl 11: 4-10. (Abstract Only).*
Goldman et al. (Editors). Cecil's Textbook of Medicine (Twenty-First Edition).W.B. Saunders Company. 2000. p. 1060-1074, 1591-1603 and 1858-1888.*
Monographs 3274-3276. The Merck Index (Eleventh Edition). Merck & Co., Inc. 1989. p. 518.*
Pilepich et al. "Androgen deprivation therpay with radiation therapy compared with radiation therapy alone for locally advanced prostatic carcinoma: A randomized comparative trial of the Radiation Therapy Oncology Group". Urology, 45(4); 1995:616-623.*
Jacob LS [Editor]. "Cancer Chemotherapy". The National Medical Series for Independent Study: Pharmacology (Fourth Edition). Williams and Wilkins, p. 253-274.*
Martiniello-Wilks et al. "In Vivo Gene Therapy for Prostate Cancer: Preclinical Evaluation of Two Different Enzyme-Directed Prodrug Therapy Systems Delivered by Identical Adenovirus Vectors". Human Gene Therapy, 9(11); 1998:1617-1626.*
Jacob LS [Editor]. "Cancer Chemotherapy". The National Medical Series for Independent Study: Pharmacology (Fourth Edition). Williams and Wilkins, p. 253-274, (1996).*
Dismukes, "Histoplasmosis," In: *Ceclin Textbook of Medicine*, Goldman and Bennett, eds., 21st Edition, vol. 1, 1860-1862, 2000.
Dismukes, "Introduction to the Mycoses," In: *Ceclin Textbook of Medicine*, Goldman and Bennett, eds., 21st Edition, vol. 1, 1858-1860, 2000.
Dismukes, "Paracoccidioidomycosis," In: *Ceclin Textbook of Medicine*, Goldman and Bennett, eds., 21st Edition, vol. 1, 1866-1867, 2000.

(Continued)

*Primary Examiner*—Ardin Marschel
*Assistant Examiner*—Leslie A Royds
(74) *Attorney, Agent, or Firm*—Fulbright & Jaworski LLP

(57) ABSTRACT

An invention relating to therapeutic pharmacological agents and methods to chemically induce intracellular hyperthermia and/or free radicals for the diagnosis and treatment of infections, malignancy and other medical conditions. The invention relates to a process and composition for the diagnosis or killing of cancer cells and inactivation of susceptible bacterial, parasitic, fungal, and viral pathogens by chemically generating heat, and/or free radicals and/or hyperthermia-inducible immunogenic determinants by using mitochondrial uncoupling agents, especially 2,4 dinitrophenol and, their conjugates, either alone or in combination with other drugs, hormones, cytokines and radiation.

9 Claims, 33 Drawing Sheets

OTHER PUBLICATIONS

Dismukes, "Sporotrichosis," In: *Ceclin Textbook of Medicine*, Goldman and Bennett, eds., 21st Edition, vol. 1, 1870-1871, 2000.

Emge et al., "Effects of Dinitrophenol on an Experimental Sarcoma of the White Rat," *Proc. Soc. Exper. Biol. Med.*, 31: 152-154, 1933.

Feinberg, "Pneumocystis Carinil Pneumonia," In: Ceclin Textbook of Medicine, Goldman and Bennett, eds., 21$^{st}$ Edition, vol. 1, 1877-1883.

Galgiani, "Coccidioidomycosis," In: *Ceclin Textbook of Medicine*, Goldman and Bennett, eds., 21st Edition, vol. 1, 1863-1864, 2000.

Ghosh et al., "Post-Metaphase Mitotic Events in Cells Treated with Dinitrophenol," *Indian Journal of Experimental Biology*, 27(4): 317-323, 1989.

Karchmer, "Antibacterial Therapy," In: *Ceclin Textbook of Medicine*, Goldman and Bennett, eds., 21st Edition, vol. 1, 1591-1603, 2000.

Kumar, "Melatonin: a master hormone and a candidate for universal panacea," *Indian Journal of Experimental Biology*, 34(5): 391-402, 1996.

Lock et al., "Differential Ability of 2, 4-Dinitrophenol to Modulate Etoposide Cyctotoxicity in Mammalian Tumor Cell Lines Associated with Inhibition of Macromolecular Synthesis," *International Journal of Oncology*, 8(2): 305-311, 1996.

Nozue et al., "Effect of Some Enzyme Inhibitors on ATP Level and Hypersensitive Reactivity of Potato Tuber Disks to Incompatible Race of Phytophthora Infestans," *Nippon Shokubutsu Byori Gakkaiho—Annals of the Phytopathological Society of Japan*, 46(1): 34-39, 1980.

Oda et al., "The Effect of Induced Hyperthermia on Kidney Function in Dogs," *Japanese Journal of Anesthesiology*, 35(9): 1374-1379, 1986.

Oka et al., "Immunosuppression in organ transplantation," *Japanese Journal of Pharmacology*, 71(2): 89-100, 1996.

Rickels et al., "The clinical presentation of generalized anxiety in primary-care settings: practical concepts of classification and management," *J. Clin. Psychiatry*, 58(Suppl. 11): 4-10, 1997.

Saag, "Dematiaceous Fungal Infections," In: *Ceclin Textbook of Medicine*, Goldman and Bennett, eds., 21st Edition, vol. 1, 1887-1888, 2000.

Saag, "Mycetoma," In: *Ceclin Textbook of Medicine*, Goldman and Bennett, eds., 21st Edition, vol. 1, 1885-1887, 2000.

Smith et al., "Hormone replacement therapy in the menopause: a pro opinion," *CA Cancer J. Clin.*, 46(6): 343-63, 1996.

Sri-Pathmanathan et al., "Clofazimine Alters the Energy Metabolism and Inhibits the Growth Rate of a Human Lung-Cancer Cell Line In Vitro and In Vivo," *International Journal of Cancer*, 56(6): 900-905, 1994.

Weitzel et al., "Similar Dose Response of Heat Shock Protein Synthesis and Intracellular pH Change in Yeast," *Exp. Cell. Res.*, 159: 252-256, 1985.

European Search Report for EP 99 93 5949, issued Jul. 15, 2003.

Summons to attend oral proceedings pursuant to Rule 71(1) EPC for EP 99 93 5949, issued Apr. 6, 2006.

Chun et al., "Mucormycosis," In: *Ceclin Textbook of Medicine*, Goldman and Bennett, eds., 21st Edition, vol. 1, 1883-1885, 2000.

Database WPI, ZA 9 208 419 A, Derwent Publications Ltd., London, GB, 1994 [abstract].

Description of 2,4-Dinitrophenol, The Marck Index: An Encyclopedia of Chemicals, Drugs, and Biologicals, 11th Edition, Budavari et al., eds., 1989.

Dismukes, "Blastomycosis," In: *Ceclin Textbook of Medicine*, Goldman and Bennett, eds., 21st Edition, vol. 1, 1865-1866, 2000.

Dismukes, "Candidiasis," In: *Ceclin Textbook of Medicine*, Goldman and Bennett, eds., 21st Edition, vol. 1, 1871-1875, 2000.

Dismukes, "Cryptococcosis," In: *Ceclin Textbook of Medicine*, Goldman and Bennett, eds., 21st Edition, vol. 1, 1868-1870, 2000.

Feinberg, "Pneumocystis Carinii Pneumonia," In: Ceclin Textbook of Medicine, Goldman and Bennett, eds., 21$^{st}$ Edition, vol. 1, 1877-1883, (2000).

Galgiani, "Coccidioidomycosis," In: *Ceclin Textbook of Medicine*, Goldman and Bennett, eds., 21st Edition, vol. 1, 1863-1864, 2000.

Rickels et al., "The clinical presentation of generalized anxiety in primary-care settings: practical concepts of classification and management," *J. Clin. Psychiatry*, 58(Suppl. 11): 4-10, 1997.

* cited by examiner

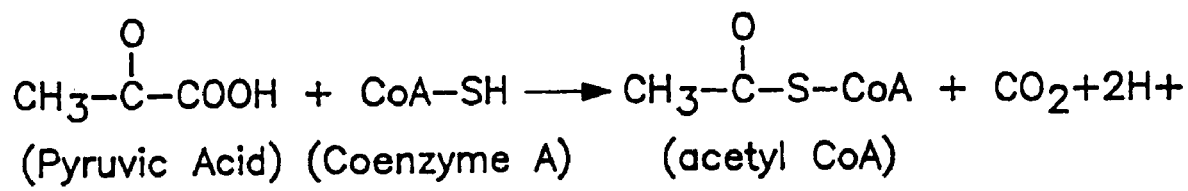
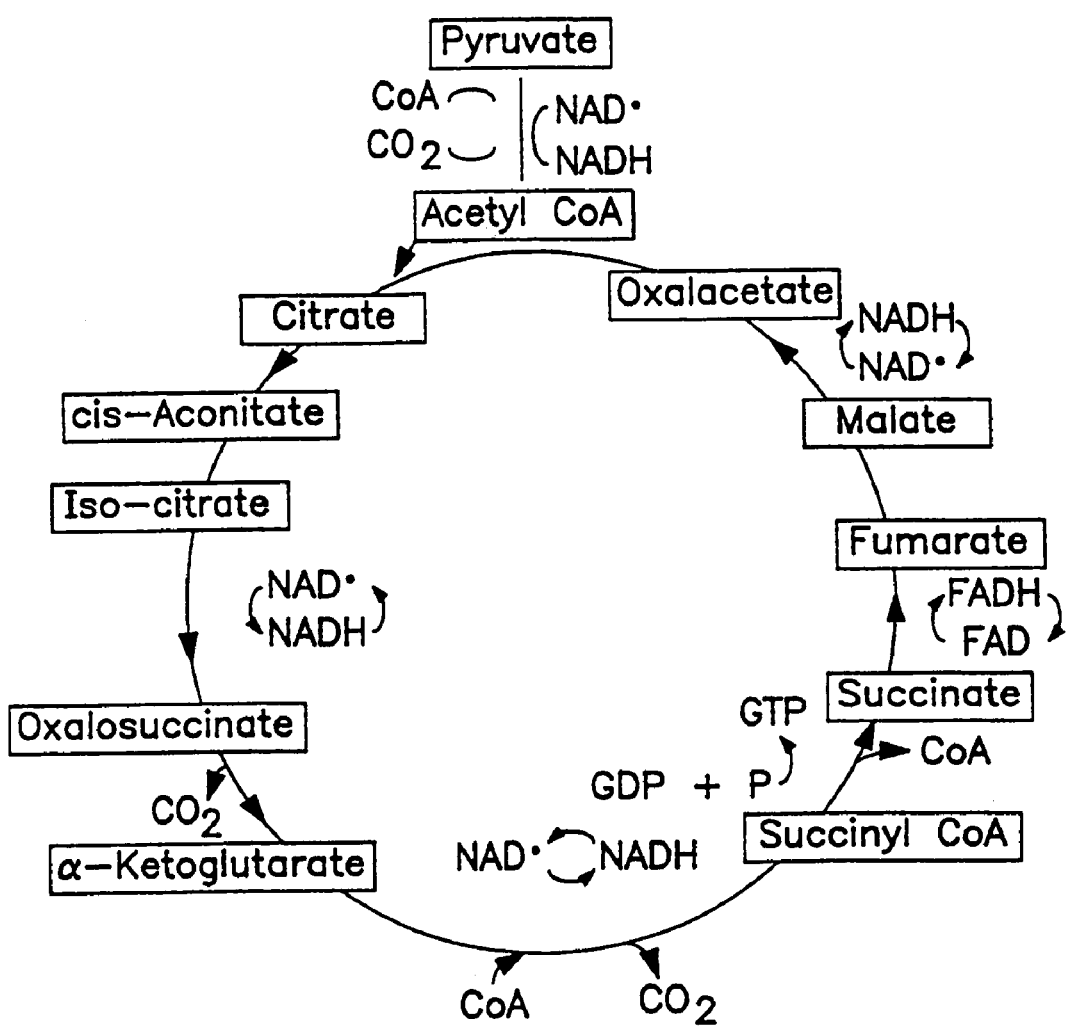
FIG. 2

| Tissue | Mass (kg)* | Blood Flow (L/min)* | Metabolic Rate (W)* |
|---|---|---|---|
| Liver | 2.6 | 1.5 | 18 |
| Brain | 1.4 | 0.75 | 17 |
| Skeletal Muscle | 31.0 | 1.2 to 24 | 17 to 350 |
| Heart Muscle | 0.3 | 0.25 to 31 | 10 to 31 |
| Kidney | 0.3 | 1.25 | 6 |
| Skin | 3.6 | 0.4 to 2.8 | 4 to 30 |

* Mean values under physiologic conditions.

FIG. 12

| Patient Name: | Sex:F | Wt: 68 kg | Ht: 165cm | BP 130/80 | Resp:20 | | | | |
|---|---|---|---|---|---|---|---|---|---|
| TIME (min) | MEDICATION/PROCEDURE (type/dose/route) | *VO2 (ml/min) | *HEAT (Kcal/hr) | *TEMP (C) | *HR (BPM) | *VCO2 (ml/min) | *VE (L/min) | NOTES | |
| (-5 to 0) | Body Wet Suit | 240 | 70.2 | 37.1 | 88 | 210 | 7.1 | Base mean over 5 minutes | |
| 0 to 2 | *DNP-1mg/kg/IV | | | | | | | DNP infused over 2 minutes | |
| 10 | | 260 | 75.8 | 37.4 | 86 | 300 | 7.6 | All vital signs normal | |
| 20 | DNP-2mg/kg/IV | 340 | 99.1 | 37.2 | 86 | 398 | 8.8 | DNP infused over 2 minutes | |
| 40 | DNP-2mg/kg/IV | 600 | 175 | 37.3 | 82 | 490 | 16.9 | DNP infused over 2 minutes | |
| 60 | | 710 | 207 | 39.1 | 94 | 690 | 18 | | |
| 90 | | 780 | 227 | 39.8 | 90 | 710 | 16.2 | | |
| 120 | | 760 | 221 | 40.2 | 92 | 680 | 17.1 | | |
| 150 | Body Wet Suit Removed | 700 | 204.2 | 40.3 | 98 | 680 | 18.1 | Evaporative heat loss initiated | |
| 160 | | 680 | 198 | 40.1 | 105 | 670 | 16.9 | | |
| 240 | | 600 | 175 | 39.2 | 98 | 590 | 14.2 | | |
| 300 | | 500 | 145 | 38.4 | 96 | 490 | 14 | | |
| 360 | Final Reading | 340 | 99.1 | 37.6 | 88 | 300 | 11.4 | Vital signs stable | |
| | *DNP=2,4-dinitrophenol | | | | | | | | |
| | *VO2=oxygen consumption | | | | | | | | |
| | *Heat=VO2 x 4.862 Kcal* | | | | | | | | |
| | *Temp = degrees centigrade | | | | | | | | |
| | *HR = heart rate (beats/min) | | | | | | | | |
| | *VCO2=carbon dioxide produced | | | | | | | | |
| | *VE=expired air volume (liters/min) | | | | | | | | |
| | NOTE: 1 liter of oxygen consumed yields 4.862 kilocalories of heat at standard conditions | | | | | | | | |

FIG. 14

| Patient Name: | Sex:M | Wt: 90kg | Ht: 177.8cm | BP 140/80 | Resp:18 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| -60 | diazepam, 10mg/PO | | | | | | | Dressed in modified wet suit |
| -15 | IV fluids, D5W/.5NS+7meq K+ | | | | | | | Drip rate @ 12cc/kg/hr |
| | placement of monitors | | | | | | | |
| (-10 to 0) | baseline readings | 300 | 87.5 | 37 | 76 | 180 | 6.5 | mean recordings over 10 minutes |
| 0 to 3 | DNP, 1mg/kg/IV | 380 | 110 | 37.1 | 78 | 220 | 8.1 | DNP infused over 2 min period |
| 10 | | 410 | 119 | 37.3 | 76 | 380 | 12.4 | complained of some IV "burning" |
| 20 | DNP, 3mg/kg/IV | 420 | 123 | 37 | 82 | 330 | 11.8 | DNP infused over 2 min period |
| 40 | | 620 | 180 | 37.2 | 84 | 680 | 17.8 | stable 5 min post injection |
| 40 to 42 | Glucagon, 0.5mg/kg/Ivdrip/hr | 760 | 221 | 37.5 | 86 | 750 | 18.2 | readings stabilized at 15 minutes |
| 50 | | 800 | 236 | 37.8 | 90 | 790 | 18.9 | |
| 60 to 70 | Glucagon, 1.0mg/kg/Ivdrip/hr | 810 | 250 | 38 | 94 | 840 | 21 | complaints of mild nausea |
| 75 to 80 | Glucagon 2.0mg/kg/Ivdrip/hr | 860 | 260 | 38.5 | 100 | 890 | 21.7 | no complaints |
| 90 | | 910 | 265 | 39.1 | 110 | 920 | 26.2 | states skin is "very warm" |
| 100 | | 880 | 256 | 39.6 | 112 | 970 | 26.1 | |
| 110 | | 960 | 279 | 39.9 | 110 | 940 | 24.3 | |
| 120 | | 880 | 256 | 40.1 | 112 | 980 | 25.2 | |
| 130 | | 900 | 262 | 40.3 | 115 | 850 | 26.5 | |
| 140 | | 890 | 260 | 40.1 | 112 | 1,050 | 27.8 | lower extremity uncovered |
| 150 | | 880 | 256 | 40.2 | 100 | 950 | 25.8 | wet suit opened |
| 160 | Glucagon discontinued | 830 | 242 | 40.1 | 110 | 900 | 26.7 | Total dose: glucagon=3mg |
| 170 | IVs discontinued, monitors removed | 810 | 236 | 39.5 | 100 | 880 | 24.5 | |
| 420 | Oral tube for VO2 | 360 | 105 | 37.2 | 88 | 400 | 8.1 | All vital signs normal |

FIG. 15

| Patient Name: | Sex:M | Wt:60kg | Ht: 155cm | BP128/72 | Resp:20 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| (-5 to 0) | dressed in cold water dry suit Baseline | 300 | 87.5 | 38.1 | 85 | 275 | 5.9 | oral breathing tube used/room air |
| 0 to 2 | DNP, 2mg/kg/IV | 320 | 99 | 38.2 | 86 | 290 | 6.2 | DNP infused over a 2 min period |
| 20 | | 340 | 99.1 | 38.1 | 88 | 300 | 8.1 | |
| 30 | | 380 | 110 | 38.6 | 92 | 350 | 9.6 | |
| 40 to 42 | DNP, 2mg/kg/IV | 340 | 99 | 38.8 | 90 | 360 | 10 | DNP infused over a 2 min period |
| 60 | | 610 | 178 | 39.4 | 90 | 390 | 11.4 | BP: falls to 110/50 |
| 90 | | 630 | 183 | 39.5 | 92 | 610 | 15.2 | BP: 105/60 |
| 92 | Levophed, 1ugm/min/Ivdrip | 650 | 189.5 | 39.5 | 92 | 630 | 21 | BP: 100/60 |
| 96 | | 790 | 230 | 39.8 | 102 | 770 | 17.4 | BP: 110/60 |
| 100 | | 850 | 247 | 40.1 | 115 | 830 | 16.7 | BP: 130/80 |
| 115 | Levophed decreased to 0.5ugm/min | 1,000 | 291 | 41.5 | 110 | 1,200 | 25.8 | Stable BP @ 130/80 |
| 125 | | 980 | 285 | 41.6 | 108 | 1,040 | 26.6 | Rt. Lower extremity uncovered |
| 160 | | 880 | 256 | 41.1 | 110 | 990 | 27.2 | |
| 180 | | 960 | 279 | 41.5 | 112 | 1,000 | 29.8 | |
| 220 | | 1,000 | 291 | 41.3 | 110 | 1,100 | 28.3 | |
| 230 | | 800 | 233 | 41.1 | 105 | 920 | 27.8 | VO2 falling |
| 240 | | 760 | 221 | 41.3 | 108 | 830 | 21.1 | VO2 continues to fall |
| 242 to 244 | DNP, 1mg/kg/IV | 890 | 260 | 41.4 | 110 | 980 | 24.8 | DNP infused over a 2 min period |
| 280 | | 1,080 | 315 | 41.6 | 115 | 1,280 | 28.6 | Both lower extremities uncovered |
| 300 | | 1,000 | 291 | 41.3 | 110 | 1190 | 29.5 | |
| 320 | Levophed stopped | 1,100 | 320 | 41.1 | 108 | 1240 | 31.1 | |
| 360 | | 950 | 277 | 40.9 | 98 | 1,040 | 29.2 | cold water dry suit |
| 390 | | 910 | 265 | 39.2 | 94 | 990 | 28.5 | |
| 420 | Monitors removed | 830 | 242 | 38.6 | 92 | 920 | 16.8 | |
| 450 | oral breathing tube | 420 | 123 | 37.8 | 88 | 510 | 10.2 | |
| 480 | | 340 | 99.1 | 37.5 | 90 | 440 | 8.9 | Vital signs within normal limits |

FIG. 17

| Patient Name: | Sex:F | Wt:60kg | Ht: 160cm | BP130/70 | Resp:20 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| (-240) | alprazolam, 2mg/PO | | | | | | | to calm anxiety |
| (-20) | dressed in dry water immersion suit | | | | | | | dressed |
| (-15) | IV fluids, D5W1/2NS+7meq K+ | | | | | | | Monitors & Foley attached |
| (-10 to 0) | Baseline Readings | 220 | 64.2 | 37.3 | 86 | 190 | 5.2 | |
| 0 to 2 | DNP, 1mg/kg/IV | 230 | 67 | 37.3 | 90 | 200 | 5.5 | DNP infused over a 2min period |
| 20 | | 250 | 72.9 | 37.2 | 88 | 230 | 6.3 | |
| 20 to 22 | DNP, 2mg/kg/IV | 250 | 72.9 | 37.8 | 86 | 220 | 6.3 | DNP infused over a 2min period |
| 30 | DNP, 1mg/kg/IV | 310 | 90.4 | 38.4 | 86 | 290 | 10.4 | |
| 50 | | 380 | 110 | 38.9 | 90 | 350 | 14 | |
| 50 to 54 | DNP, 1.0mg/kg/IV | 400 | 116 | 39.5 | 90 | 390 | 14 | DNP infused over a 2min period |
| 70 | | 600 | 175 | 40.2 | 110 | 590 | 18 | Patient became briefly agitated |
| 80 | | 570 | 166 | 40.8 | 98 | 550 | 18 | |
| 90 | | 500 | 145 | 40.1 | 100 | 510 | 15 | 20 sec readings show fall in VO2 |
| 95 to 98 | Dopamine Drip/3mcg/kg/min | 520 | 151.6 | 40.2 | 115 | 500 | 15.8 | |
| 100 | | 630 | 183 | 40.3 | 115 | 610 | 18 | |
| 110 | | 680 | 198.2 | 40.2 | 110 | 690 | 20 | |
| 150 | | 710 | 207 | 40.5 | 110 | 700 | 21 | |
| 180 | | 680 | 198.2 | 40.6 | 115 | 690 | 19 | Dopamine discontinued |
| 250 | | 650 | 189 | 40.1 | 110 | 660 | 19 | |
| 255 | | 600 | 175 | 39.6 | 112 | 610 | 22 | patient complains of fatigue |
| 280 | Insulating Suit open | 430 | 125 | 39.1 | 115 | 410 | 14 | |
| 320 | | 340 | 99.1 | 37.8 | 92 | 330 | 12 | |
| 400 | chills & rigors | | | | | | | |
| 401 to 405 | IV fluids, dopamine 2mcg/kg/min | 380 | 110 | 38.7 | 100 | 270 | 15 | IV fluids & observation |
| 500 to 610 | Symptoms subside | 250 | 72.8 | 37.8 | 90 | 230 | 7 | Jarisch-Herxheimer? |

FIG. 18

| Patient Name: | Sex:F | Wt:55kg | Ht:154cm | BP100/50 | Resp:22 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| (-50 to -40) | covered in water soaked blanket | | | | | | | |
| (-40 to -30) | polyethylene wrap around blanket | | | | | | | |
| (-30 to -10) | Carboplatin-45mg/mitomycin-24mg (total dose given by IV infusion) | | | | | | | 3 units packed RBC-24 hr prior IV fluids, D5W1/2NS+10meq K+ |
| (-10 to 0) | | 230 | 67 | 37.6 | 90 | 200 | 5.9 | Mean values over 10 min period |
| 0 to 1 | mephenteramine sulfate/30mg/IM | 250 | 72.9 | 37.7 | 85 | 220 | 6.3 | BP increased to 140/88 |
| 10 | | 320 | 93.3 | 37.9 | 96 | 290 | 5.9 | BP stable at 140/90 |
| 15 | | 340 | 99.1 | 38.1 | 98 | 300 | 7.5 | |
| 20 to 22 | DNP, 1.0mg/kg/IV | 380 | 110 | 38.2 | 100 | 350 | 6.6 | DNP infused over a 2 min period |
| 23 | | 450 | 131.2 | 38.2 | 105 | 440 | 9.8 | |
| 28 | | 400 | 116.6 | 38.8 | 105 | 510 | 12.9 | |
| 30 | | 430 | 125.4 | 39 | 110 | 500 | 13.2 | |
| 40 to 42 | DNP, 0.5mg/kg/IV | 480 | 139.9 | 39.4 | 110 | 560 | 15.8 | DNP infused over a 2 min period |
| 50 | | 520 | 151.6 | 39.9 | 115 | 540 | 16.2 | |
| 60 | DNP, 0.5mg/kg/IV | 640 | 186.6 | 40.3 | 112 | 660 | 18.4 | DNP infused over a 2 min period |
| 70 | | 660 | 192.4 | 40.8 | 115 | 720 | 21.3 | |
| 80 | DNP, 0.5mg/kg/IV | 780 | 227.4 | 40.9 | 110 | 880 | 19.3 | DNP infused over a 2 min period |
| 90 | | 800 | 233 | 41.2 | 120 | 850 | 18.7 | |
| 100 | | 820 | 239 | 41.4 | 125 | 810 | 20.6 | |
| 120 | | 790 | 230.4 | 41.5 | 115 | 740 | 15.5 | |
| 130 | | 800 | 233 | 41.4 | 110 | 850 | 14.9 | |
| 131 to 133 | DNP, 0.5mg/kg/IV | 820 | 239 | 41.4 | 115 | 790 | 15.8 | DNP infused over a 2 min period |
| 150 | | 810 | 236 | 41.4 | 112 | 840 | 13.7 | |
| 160 | | 800 | 233 | 41.4 | 120 | 690 | 14.1 | |
| 170 | | 850 | 247 | 41.2 | 115 | 870 | 16.7 | |
| 180 | Doxifluridine, 600mg/PO | 820 | 239 | 41.3 | 110 | 890 | 13.7 | |
| 200 | | 820 | 239 | 41.4 | 115 | 850 | 15.3 | |
| 210 | | 790 | 230.4 | 41.2 | 102 | 770 | 17.4 | IV fluids discontinued |
| 240 | | 630 | 183 | 38.6 | 100 | 550 | 14.3 | |
| 260 | | 420 | 123 | 37.5 | 102 | 395 | 10.8 | Monitors removed |

FIG. 19

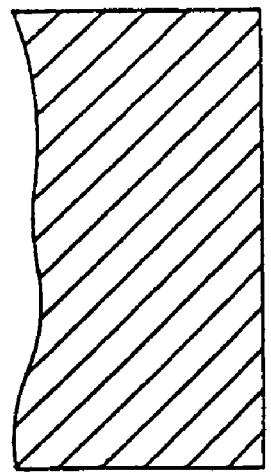
3.
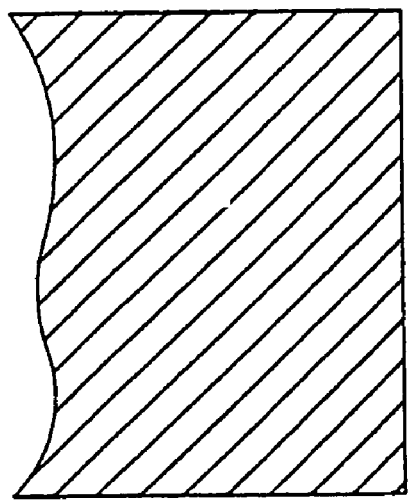
2.
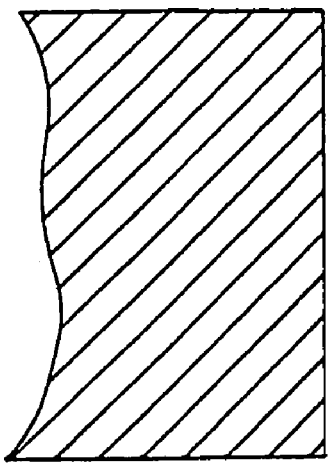
1.
Intimal Thickness
FIG. 21

| Patient Name: | Sex:M | Wt:65kg | Ht: 175cm | BP135/80 | Resp: 18 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| | Phenytoin, 200mg/TID/PO | | | | | | | Increased for 3 days |
| (-10 TO 0) | Baseline Readings | 230 | 67 | 37.5 | 86 | 210 | 4.9 | |
| 0 | DNP, 300mg/PO | 220 | 64 | 37.5 | 84 | 200 | 5.1 | DNP by mouth with H2O |
| 20 | | 230 | 67 | 37.4 | 88 | 210 | 5 | |
| 60 | | 250 | 73 | 37.3 | 88 | 220 | 5.5 | |
| 120 | FDG/Bolus/IV | 300 | 87 | 37.5 | 82 | 280 | 6.3 | |
| 140 | PET Scan initiated | 320 | 93 | 37.5 | 86 | 300 | 8 | |
| 180 | | | | | | | | |
| 210 | PET Scan completed | 340 | 99 | 37.5 | 86 | 310 | 10 | No complaints |
| 480 | | 260 | 76 | 37.4 | 84 | 250 | 7 | No complaints |

FIG. 24

| Patient Name: | Sex:F | Wt:60kg | Ht: 164cm | BP120/72 | Resp:18 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| (-10 to 0) | Baseline | 180 | 52 | 37.7 | 88 | 160 | 4.8 | |
| 1 to 2 | DNP/1mg/kg/IV | 180 | 52 | 37.6 | 86 | 165 | 4.6 | DNP infused over 2 min |
| 22 | | 210 | 61 | 37.7 | 86 | 190 | 4.8 | No complaints |
| 22 to 24 | DNP/2mg/kg/IV | 200 | | | 84 | 190 | 50 | DNP infused over 2 min |
| 60 | Thermal imaging | 300 | 93 | 37.2 | 84 | 300 | 5.8 | In isothermally controlled room |

FIG. 25

| Patient Name: | Sex:M | Wt:72kg | Ht: 175cm | BP140/86 | Resp:22 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| (-240) | 2 units packed RBCs | | | | | | | 48 hours prior to treatment |
| (-8 to 0) | Lactated Ringers/IV | | | | | | | 100cc/hour |
| (-8 to 0) | Baseline studies | 250 | 73 | 37.6 | 88 | 220 | 6.4 | |
| 0 to 2 | DNP, 1mg/kg/IV | 260 | 75.8 | 37.6 | 88 | 230 | 6.3 | |
| 20 | | 340 | 99 | 37.8 | 88 | 330 | 12 | |
| 30 | | 360 | 105 | 37.9 | 92 | 320 | 11 | |
| 45 to 47 | DNP, 1mg/kg/IV | 340 | 99 | 37.9 | 90 | 340 | 12 | DNP infused over a 2min period |
| 60 | | 420 | 122 | 37.9 | 94 | 400 | 14 | |
| 70 | Methylene blue, 2mg/kg/IV | | | 38 | 92 | | | administered in 35ml-20min infusion |
| 80 | | 430 | 125 | 37.9 | 96 | 410 | 15 | |
| 90 | | 500 | 145 | 38 | 96 | 490 | 16 | Patient feels "warm" |
| 110 | | 480 | 140 | 38.1 | 94 | 460 | 18 | |
| 130 | | 430 | 125 | 38.2 | 92 | 410 | 16 | |
| 150 | | 390 | 114 | 38.3 | 96 | 380 | 14 | |
| 180 | | 380 | 110 | 38.3 | 96 | 360 | 15 | |
| 200 | | 360 | 105 | 38.3 | 92 | 340 | 14 | |
| 200 to 202 | DNP, 1mg/kg/IV | 370 | 108 | 38.2 | 92 | 350 | 15 | DNP infused over a 2min period |
| 222 | | 450 | 131 | 38.4 | 92 | 430 | 16 | no complaints |
| 240 | | 490 | 143 | 38.5 | 94 | 470 | 15.7 | |
| 300 | | 520 | 151 | 38.8 | 96 | 490 | 16 | |
| 360 | Treatment terminated | 470 | 137 | 38.9 | 96 | 450 | 15.8 | |
| 540 | | 380 | 110 | 38.4 | 92 | 350 | 14 | no complaints |

FIG. 26

| Treatment Period* | Serum PSA level* (ng/ml) | Acid Phosphatase (U/L) | Biopsy* | Clinical Findings |
|---|---|---|---|---|
| 0 | 58 | 1.2 | High grade adeno-carcinoma, Gleason grade 8 | Bone pain, lack of appetite, Karnofsky score of 6. |
| Day 6 | 68 | 1.6 | — | Decrease in bone pain |
| Day 8 | 125 | 1.6 | — | Increased appetite, decrease bone pain. |
| Day 14 | 88 | 1.4 | — | Off all pain meds. Marked increase in appetite. |
| 6 weeks | 30 | 1 | — | Karnofsky score of 7. Remains pain free |
| 10 weeks | 18 | 0.6 | over 95% tumor necrosis, rare intact acini; cyst-like structures. | Karnofsky score 8. Pain free |
| 12 weeks | 12 | 0.6 | — | Gained 8.2kg weight. Pain free. |
| 4 months | 6.5 | 0.65 | Extensive fibrosis. Increase in stromal cells. Occasional tumor cells with reduced cytoplasm | Total of 9.3kg of weight gain. Pain free. Karnofsky score of 9 |

*Treatment period – DNP given IV every other day x 30, repeated after 2 weeks for additional 30 days; then, 250mg/orally/2 times daily for 5 days and, recycled after no DNP for 2 days for a total period of 4 months.

*PSA = Prostatic Specific Antigen

*Biopsy – Significant comments by pathologist.

FIG. 27

| Patient Name: | Sex:F | Wt:48kg | Ht: 150cm | BP128/82 | Resp:18 | | | |
|---|---|---|---|---|---|---|---|---|
| TIME (min) | MEDICATION/PROCEDURE (type/dose/route) | VO2 (ml/min) | HEAT (Kcal/hr) | TEMP (C) | HR (BPM) | VCO2 (ml/min) | VE (L/min) | NOTES |
| (-360) | Interferon alpha/1.5million units/SQ | | | | | | | |
| (-5 to 0) | Baseline readings | 160 | | 37.5 | 76 | | | |
| 0 to 2 | DNP, 1mg/kg/IV | 150 | 47 | 37.5 | 76 | 140 | 3.5 | DNP infused over 2min period |
| 20 | | 210 | 44 | 37.5 | 76 | 140 | 4 | |
| 20 to 22 | DNP, 1mg/kg/IV | | 61 | 37.7 | 80 | 190 | 4.2 | DNP infused over 2min period |
| 40 | | 250 | 73 | 38 | 84 | 220 | 5 | |
| 50 to 52 | DNP, 2mg/kg/IV | | | | | | | DNP infused over 2min period |
| 70 | | 360 | 105 | 38.3 | 86 | 330 | 9 | |
| 170 to 172 | DNP, 2mg/kg/IV | 280 | 82 | 38.8 | 88 | 260 | 8.5 | DNP infused over 2min period |
| 190 | | 420 | 122 | 38.8 | 88 | 400 | 12 | sweating profusely |
| 240 | | 400 | 116 | 38.7 | 86 | 370 | 14 | very thirsty |
| 300 | Treatment terminated | 380 | 110 | 38.7 | 90 | 350 | 14 | marked fatigue |
| 420 | | 340 | 99 | 38.5 | 90 | 330 | 13 | no complaints other than severe fatigue |

FIG. 28

| Treatment Period | HCV-RNA* (copies/ml) | AST* (IU/L) | ALT* (IU/L) |
|---|---|---|---|
| 0 | $5.8 \times 10^6$ | 78 | 85 |
| 48 hours | $4.6 \times 10^4$ | 400 | 610 |
| 14 days | non-detectable | 380 | 570 |
| 21 days | non-detectable | 100 | 78 |
| 18 months | non-detectable | 45 | 34 |

*HCV-RNA – Roche polymerase chain reaction methodology

*AST – aspartate aminotransferase

*ALT – alanine aminotransferase

FIG. 29

CHEMICAL INDUCED INTRACELLULAR HYPERTHERMIA

CROSS-REFERENCE TO RELATED APPLICATIONS

This application is the National Stage application of International Application No. PCT/US99/16940 filed Jul. 27, 1999 which claims benefit of priority to U.S. provisional patent application Ser. No. 60/094,286, filed Jul. 27, 1998, which is hereby incorporated by reference in its entirety.

FIELD OF INVENTION

This invention relates to therapeutic pharmacological agents and methods to chemically induce intracellular hyperthermia and/or free radicals for the diagnosis and treatment of infections, malignancy and other medical conditions. This invention further relates to a process and composition for the diagnosis or killing of cancer cells and inactivation of susceptible bacterial, parasitic, fungal, and viral pathogens by chemically generating heat, free radicals and hyperthermia-inducible immunogenic determinants. Such pathogens, infected or transformed cells are inactivated or killed without irreparable injury to non-transformed, uninfected, normal cells. More specifically, this invention relates to the diagnosis and treatment of cancer; treatment of AIDS; and, other diseases and conditions using mitochondrial uncoupling agents, especially 2,4 dinitrophenol and, their conjugates, either alone or in combination with other drugs, hormones, cytokines and radiation.

GENERAL BACKGROUND

Local heat, systemic hyperthermia and fever therapy have been empirically used as effective treatments for malignant, infectious and other diseases since antiquity. Therapeutic hyperthermia was first documented in the Edwin Smith surgical papyrus in the 17th century B.C. Coley's toxin extracts of *Streptococcus erysipelatis* (group A *streptococcus*) and *Bacillus prodigiosus* (*Serratia marcescens*) were used to induce fever for the treatment of patients with advanced cancer. The Nobel Prize was awarded for using fever therapy in the treatment of neurosyphilis with the injection of malarial blood. As late as 1955, the Mayo Clinic advocated using malariotherapy or heat therapy for cases of tertiary syphilis "resistant to penicillin". Long term remissions in patients with inoperable carcinomas that were treated with hot baths and local heat applications have also been reported. Published observations on the disappearance of malignancies such as a soft tissue sarcoma in a patient experiencing high fever due to erysipelas and tumor lysis of Burkitt's lymphomas following malignant hyperthermia during surgical anesthesia are known. A comprehensive historical review on anecdotal observations and intuitive rational for the empirical use of therapeutic hyperthermia has been published by Myer, J. L.

The temperature of a body can be intentionally increased either by pyrogens to produce fever (fever therapy) or, by the induction of hyperthermia (therapeutic hyperthermia). Fever raises body temperature by elevating the thermoregulatory "set point" located in the preoptic region of the anterior hypothalamus. In so doing, the body physiologically works to maintain the higher temperature setting. The elevated core body temperature increased by fever may or may not be raised above the higher set point value. In contrast, induced hyperthermia always raises the body temperature above the hypothalamic thermoregulatory set point and the physiologically intact body attempts to lower it's core temperature back to the set point baseline.

Renewed clinical interest in hyperthermia has occurred over the past 35 years due to continued failure of standard therapies to treat various forms of cancer and emerging infections. Except for a few exceedingly rare forms of cancer like childhood leukemias and testicular cancer or immune responsive infections, chemotherapy, radiation or drug therapy often do very little except briefly extend survival. One of the major obstacles to "cure" disseminated cancer and infections has been the innate or acquired resistance of tumor cells and emerging microbes to antibiotics, drugs and treatments given in tolerable doses. Escalation of treatments, or use of multiple drugs to overcome resistance is invariably prevented by concomitant toxicities or development of multi-drug resistance. Further, in contrast to drugs, which represent a single molecular species that biochemically interact with specific enzymes or receptors of viruses, prokaryotes and eukaryotes, the action of hyperthermia is biophysical and global. Hyperthermia has no specific heat receptors. Therefore, the possibility of a point mutation causing a functional change in a receptor and conferring resistance to hyperthermia is unlikely, and would be equivalent to the development of resistance to the in vitro process of Pasteurization. Among pathogenic bacteria, it has been reported that only one variant in $1 \times 10^6$ cells of an original population is resistant to hyperthermia.

Hyperthermia has been used alone or in conjunction with radiation and chemotherapy in the treatment of a variety of malignancies. Overgaard et al., reported that a combination of heat and radiation results in complete control of twice as many melanoma lesions compared to radiation alone. Maeda, M., Watanabe, N. et al., published in Gastroenterologia Japonica, that hyperthermia with tumor necrosis factor resulted in successful treatment of hepatocellular carcinoma. Prospective randomized studies of hyperthermia combined with chemoradiotherapy for esophageal carcinoma demonstrated the cumulative three year survival rates to be more than doubled with the addition of hyperthermia to chemoradiotherapy. Combination chemotherapy with hyperthermia in metastatic breast cancer refractory to common therapies, i.e., failed prior hormonal therapy and chemotherapy, resulted in 39% complete remissions and 23% partial remissions: relief of bone pain was striking. Fujimoto, S., Takahashi, M. et al., demonstrated that the 5 year survival rate of patients with peritoneal carcinomatosis from gastric carcinoma treated with intraperitoneal hyperthermic chemoperfusion was 41.6%, whereas the 50% survival duration of the group that did not receive intraperitoneal hyperthermia was 110 days. Preoperative hyperthermia with chemotherapy and radiation is also known to improve long-term results in patients with carcinoma of the rectum, especially those with advanced disease. It is clinically known that regional, i.e., limb, hyperthermic perfusions with chemotherapy is useful for the treatment of melanoma. Combination therapy with hyperthermia and radiation has been successful in the treatment of non-Hodgkins lymphomas. More recently, a survival benefit of hyperthermia was shown in a prospective randomized trial for patients with glioblastoma multiforme undergoing radiotherapy. However, rigorous clinical prospective randomized trials with hyperthermia alone or, in combination with agents outside its use with radiation therapy have not been performed.

The scientific rationale for therapeutic hyperthermia in cancer therapy rests on known data from pre-clinical, in vitro and animal studies. Tumor cells in tissue culture have been demonstrated to be directly more sensitive to heat as compared to their non-malignant counterparts. Cells undergoing mitosis, synthesizing DNA in the 'S-phase', are especially more sensitive to hyperthermia. Human leukemic progenitor cells have been shown to be selectively killed by hyperthermia and, such in vitro use has been shown to purge bone marrow of residual tumor cells before autologous bone marrow transplantation. Microcalorimetric measurements confirm that tumorous tissues produce more heat and are "hotter" than their non-tumorous counterparts. As a consequence, they are less able to tolerate additional heat loads.

Tumor cells are also killed by heat indirectly. Tumor angiogenesis is inhibited by heat. Hyperthermia causes tumors to have increased heat retention with increased cytoxicity due to tumor neovasculature lacking smooth muscle and vessel wall precursors needed for cooling by vasodilation. Increased hypoxia, acidity, Fos gene death signaling, decreased nutrient supply and enhanced immunologic cytotoxicity have also been reported to be caused by hyperthermia and contribute to enhanced tumor cell death. Further, the combination of hyperthermia with chemotherapy and/or radiation has been shown to be supraadditive or synergistic on killing of tumors. Human gastric carcinoma cells have been shown to be selectively killed by a combination of cisplatin, tumor necrosis factor and hyperthermia: a 40% increase in cisplatin DNA damage was noted in the presence of the three agent combination over cisplatin alone or either dual combination. Numerous animal studies, including the initial publication by Crile, show that neoplasms transplanted into mice regress when treated with hyperthermia without irreparable damage to adjacent tissues.

Body temperature is a critical factor in determining host susceptibility, location of lesions, and the natural history of many infectious diseases. Temperature has direct effects on the growth of all microorganisms, including those that are pathogenic. Almost all of the bacteria that cause disease in humans grow optimally within the range of 33-41° C. and, their temperature growth characteristics are not easily altered in vitro. By example, the lesions of Hansen's disease (leprosy) caused by *Mycobacterium leprae*, characteristically grow and destroy the most acral, coolest parts of the body such as fingers, toes, external ear, the air-stream cooled nasal alae and larynx. Leprosy organisms proliferate and follow the coolest temperature gradients in the body, 25-33° C. In animals, the leprae organisms can only be grown in the armadillo or foot pads of mice where the in situ lesion temperatures are 27-30° C. Spontaneous improvement in leprosy lesions have been reported in patients following febrile illness. Fever therapy, hot baths and local heat therapy were formerly utilized in treating this disease. Hyperthermia is also known to destroy *Treponema pallidum*, the causative agent of syphilis, by heating five hours at 39° C., three hours at 40° C., two hours at 41° C. or one hour at 41.5° C. The spirochetes responsible for yaws, bejel, pinta and Lyme disease show similar temperature sensitivity.

Other bacteria that predominately cause lesions at cool sites and are susceptible to heat inactivation include, *Neisseria gonorrhea, Hemophillus ducrei* (chancroid), *Mycobacterium ulcerans, Mycobacterium marinum* ("swimming pool" granuloma), Diphtheria, etc. Further, hyperthermia has been reported to be synergistic with antibiotic and chemotherapy in the treatment of various bacterial diseases. Elevated body temperature potentiates the effect of penicillin on staphylococci and syphilis. Hyperthermia makes sulfadiazene bactericidal for streptococci. Moreover, recent controlled studies show that when antipyretics are used in animals with severe experimentally induced infections, there is increased mortality. Nonetheless, systemic hyperthermia has generally been abandoned as a treatment for bacterial infections with the advent of antibiotics.

Hyperthermia has remained an effective treatment for many fungal infections. Superficial dermatophytosis flourish in cooler regions of the body and heat treatment is oftentimes the only viable therapy for their chronic granulomatus lesions. By example, *Sporothrix schenkii*, the causative agent of sporotrichosis, has a temperature growth optimum well below 37° C. and is successfully eliminated by local hyperthermia. Similarly, patients with pseudallescheriosis unresponsive to antifungal antibiotics are healed with hyperthermic treatments. In Japan, pocket warmers, hot water and infrared heating remain current and effective treatments for various fungal infections. Systemic hyperthermia, utilizing a Liebel-Flarsheim (Kettering) Hypertherm Fever Cabinet, dramatically treated a case of disseminated sporotrichosis with recurrent iridocyclitis, repeated post-treatment cultures from the patient remained negative.

The role of hyperthermia in modulating the clinical course of other fungal infections, including histoplasmosis, North American blastomycosis, chromomycosis, cryptococcosis, paracoccidioidomycosis, Lobos' disease and candidiasis has been described. Fungi, such as *Nocardia, Actinomyces* and *Aspergillus* also proliferate in cooler regions of the body causing mandible (lumpy jaw) and foot lesions (Madura foot) respectively. In vitro heat sensitivity data for many of the above and other pathogenic fungi have been reported by Mackinnon et al., Silva and others.

The effect of temperature and hyperthermia on the pathogenesis of parasitic disease is also well known. Leishmaniasis, a wide spread parasitic disease transmitted by the bite of a sandfly, clinically infects 12 million people worldwide. The cutaneous and mucocutaneous lesions, i.e., Oriental sore, Baghdad boil, Delhi boil, Chiclero's ulcer and espundia, are often very destructive and permanently disfiguring. Hyperthermia with moist heat of 39° to 41° C. applied for 20 hours over several days has proven to be an effective treatment. In vitro, human macrophages infected with *Leishmania mexicana* are completely destroyed by heating at 39° C. for 3 days. All muco-cutaneous *Leishmania* strains, regardless of subspecies, demonstrate a growth optimum of 35° C. with only the *L. tropica* and *L. donovani* strains surviving temperatures of 39° C. Clinical observations have shown that hyperthermic treatment of one *Leishmania* lesion often invokes an immune response and results in the healing of other lesions over a 5-6 week period. The effect of hyperthermia on other parasites, including *Trypanosoma cruzi*, malaria, microfilaria, *acanthamoeba*, trematodes and cestodes has been published.

Increased body temperature is also recognized as a major factor in recovery from viral infections. Many viruses multiply better at temperatures below 37° C. and their multiplication is inhibited or stopped if the body temperatures exceeds 39° C. In vitro Rhinovirus replication, for example, falls off by $10^6$ log units with an upward temperature shift of 2° C. (37° to 39° C.). Herpes virus replication, as well as the intracellular and extracellular herpes virus concentration, markedly decrease when the incubation temperature is elevated to 40° C. Varicella virus production in human fibroblastic cell culture is optimal at 37° C. and ceases at 39° C.

Beneficial effects of hyperthermia on the outcome of viral disease in laboratory animals infected with myxomatosis, encephalomyocarditis, herpes, gastroenteritis, rabies and the common cold in man have been documented. Influenza and viruses causing upper respiratory infections, such as the common cold, thrive in a cool body milieu of 30°-35° C. Temperature gradients in this range exist in the fall and winter within the oral, nasal, tracheal and laryngeal mucosa and lead to flu and influenza epidemics. Live respiratory-virus vaccines for influenza have been developed by use of heat-sensitive mutants that cannot reduplicate or cause clinical disease at 36°-37° C. It is known that even as little as a 0.5° C. difference in the ceiling replication temperature of a virus can have a dramatic effect on virulence and pathogenicity.

Other animal viruses such as Newcastle disease in chickens, rabbit papilloma, feline leukemia, rabbitpox, hoof-and-mouth disease in cattle, hand, foot, and mouth disease, human plantar warts, and the "grease" of horses, due to horsepox involvement of the colder acral extremities above the fetlocks, are known to be very sensitive to inhibition by heat. Heat treatment of cells infected with human immunodeficiency virus (HIV-1) at 39° C. for 2 days has been documented to significantly decrease viral production and reduce reverse transcriptase enzyme marker activity 30 fold. In vitro hyperthermia of 42.0° C. for 1 hour, 4 days apart selectively lowers HIV RNA loads in chronic (latent) infected T lymphocytes. Hyperthermia of 42° C. for 3 hours combined with tumor necrosis factor has been published to selectively kill all acute and chronically infected HIV cells in tissue culture.

Use of whole body hyperthermia has been reported to cause regression of Kaposi' sarcoma, clear oral candidiasis, eliminate hepatitis C, cause remission of Varicella-zoster, increase weight gain and improve CD4 lymphocytes counts in patients with acquired immunodeficiency syndrome (AIDS). Dramatic improvement with hyperthermia therapy has been documented in a patient infected with a debilitating Verruca vulgaris and HIV. The FDA has approved clinical trials involving hyperthermia for the treatment of AIDS with a patented extracorporeal blood heating machine to induce whole body hyperthermia. The FDA has recently expanded the extracorporeal heating machine trials to permit treatment of 40 HIV infected patients.

Hyperthermia can augment cytotoxicity and reverse drug resistance to many chemotherapeutic agents. Moreover, hyperthermia has also been shown to enhance the delivery of many novel cancer therapeutic agents, i.e., monoclonal antibodies to neoplasms with resultant improvement in antitumor effect; enhance the delivery of gene therapy with use of viral vectors; and, augment drug delivery and antitumor effects when using drug containing liposomes. In addition to increasing the rate of extravasation of liposomes from the vascular compartment by a factor of 40-50, hyperthermia can also be used to selectively release chemotherapeutic agents from liposomes designed to be thermosensitive. Thermosensitive liposomes are small vesicles composed of lipid phosphatidylcholine moieties constructed to contain and transport a variety of drugs. The liposomes are designed to remain stable in the blood and tissues at physiologic temperatures. When passing through an area of heated tissue however, they dissolve and effectively release their encapsulated contents. Thermosensitive liposomes are used to entrap and carry drugs whose systemic toxicity is desired to be limited to a particular heated tumor, organ or tissue. Examples of drugs that have been encapsulated into liposomes include methotrexate, doxorubicin, amphotericin B, cisplatin and others. Liposomes can be designed so as to release their contents at pre-determined temperatures.

Hyperthermia has also been an effective solution for the treatment of a variety of heat labile toxin or poisonous envenomations. For example, an easy treatment for Scorpaenidae and Siganidae envenomation is the local application of heat. The major poisonous component of this and many other venoms from lionfish, weever fish, bullrout, sculpin, surgeon fish, scorpion fish, stonefish, butterfly cod, etc., is a very heat labile, non-dialyzable protein. As opposed to the nuances of using specific anti-venom, immersing the envenomated area or patient in hot water, or applying other forms of hyperthermia, is a simple and prompt treatment.

Standard clinical methods of inducing hyperthermia are dependent on the deposition of exogenous heat to that normally produced by the metabolism. All current deliberate and controlled methods of heating require an external source of energy. Non-surgical methods of heating include: hot air, ultrasound, microwaves, paraffin wax baths, hot water blankets, radiant heat devices, high temperature hydrotherapy and combinations thereof. Invasive means of inducing hyperthermia include surgical insertion of various heating devices, infusion of heated solutions into the peritoneal cavity through catheters or heating the blood extracorporeally through a heat exchanger. The later method, developed by Parks et al., involves the surgical placement of a femoral arterio-venous shunt for the removal, heating and replacement of blood to induce whole body hyperthermia. A more recent experimental improvement on this method has been the induction of whole body hyperthermia with veno-venous shunt perfusions. Several machines have been patented for extracorporeal heating of blood to induce hyperthermia (see U.S. Pat. Nos. 5,391,142 and 5,674,190).

Endogenous heating by creating fevers induced with toxins, pyrogens and microorganisms have been used in the past and have recently been re-attempted. Heimlich has been reported to use Malaria therapy for the treatment of Lyme disease, AIDS and malignancy. Pontiggia et al, treated AIDS patients by combining fever, induced by parenteral injections of a streptococcal lysate preparations, with hyperthermia generated by an infrared heating bed.

Another way that the prior art has dealt with inducing hyperthermia has been by introducing micron size magnetic particles and subjecting them to either magnetic fields or hyperbaric oxygen (see U.S. Pat. No. 4,569,836). This method was designed for the treatment of cancer based on the belief that cancer cells would engulf the particles and concentrate them intracellularly. A magnetic field would then be applied to heat the particles and generate lethal hyperthermia within the cancer cells. A modification of this technology is the use of magnetic cationic liposomes to induce intracellular hyperthermia. This technology was based on the observation that glioma cells have a greater affinity for positively charged rather than 'neutral' magnetic liposomes. A more recent variation on this science has been developed in Germany using 'targeted' magnetoliposomes. This methodology has been developed in an attempt to treat AIDS by using magnetic nanoparticles coupled to either CD4 lymphocyte or anti-gp120 HIV antibodies. The magnetic nanoparticles are intended to selectively bind to either the HIV protein envelope or the HIV infected cells and then be heated by external high-frequency alternating magnetic fields.

Whether invasive or non-invasive, all current methods of inducing hyperthermia depend on an external energy source and cannot safely deliver adequate power to result in therapeutic heating. Delivery of heat to obtain the actual desired temperature to deep target tissues has not been possible because of the actual physics involved in the thermodynamic, conductive transfer of heat from the outside into the cell. Heating tissues deeper than five centimeters below the skin with microwave, radio frequency or ultrasound devices is difficult because energy absorption is not uniform or focused. Radiant heat, hot water, molten wax and other methods cause excessive heating of subcutaneous fat which acts as a barrier to body heat gain. Common adverse effects of such external heating methods include surface skin burns, blistering, ulcerations, secondary opportunistic infections and pain. Additionally, many tumors have high blood flow cooling which nullifies any potential therapeutic gain achievable through the use of such extracellular, systemic hyperthermia devices. Also, insufficient heating power prolongs the induction time required to reach the actual therapeutic temperature. This promotes resistance to heat treatment through the development of the heat shock response and thermotolerance.

High frequency electromagnetic devices used to heat intracellular magnetic particles invariably induce eddy currents within the body making it difficult to provide uniform, controlled and safe heating without toxic effects to normal cells. Further, not all tumors possess characteristics that cause them to selectively take up magnetic particles or have an affinity for positively charged magnetic liposomes. Also, magnetic cationic liposome particles are subject to various neutralizing interactions with anions, giving them a short charged half-life. Moreover, the complexity of using specific anti-HIV antibodies bound to electromagnetic particles also assumes a non-mutating HIV genome with stable antigenic determinants. To the contrary, a high mutation rate in the HIV genome and it's protein antigenic determinants is known to exist and is the main obstacle to the development of an effective vaccine. Such treatments therefore, do not selectively heat transformed cells without heating and injuring normal cells.

Extracorporeal blood heating methods require surgery and anesthesia. Further, as with all external heating methods, temperature variances and toxic conductive thermogradients from the point of initial heating to the target tissue cannot be avoided. By example, bone marrow temperatures are consistently known to be 1°-2° C. below the average body core temperature achieved by extracorporeal blood hyperthermia. This is a major problem in systemic hyperthermic therapy since the marrow is a common repository of metastatic cancer cells and infectious microorganisms. Therapeutic bone marrow temperatures are not achievable due to the fact that the intermediate tissues between the blood and the marrow create a temperature gradient cooling the blood before it reaches the bone marrow. Since efficacy and toxicity of hyperthermia depend on both the actual temperature and duration of heating, delivering the desired temperature-and-duration of heating (thermal dose) to the bone marrow would require the blood and intermediate tissues to be heated beyond that which is safe for normal, healthy cells. A multicentre European trial documented that only 14% of all protocols achieve required target temperatures. Further, current extracorporeal heating methodology and equipment is labor intensive, time-consuming and expensive.

Use of fever inducing agents such as live microorganisms, pyrogens and toxin lysates is clinically uncontrollable, unpredictable or insufficient as to both the degree and duration of temperature increase.

Further reasons why hyperthermia has not yet become more widely accepted as a mode of therapy is because current heating machines are not compatible with noninvasive temperature measurement technology. Measurement of the actual temperatures reached in target tissues is critical for heating efficacy, i.e., determining the thermal dose. Recently, noninvasive thermometry with Magnetic Resonance Imaging (MRI), ultrasound backscatter, electrical impedance, electromagnetic adaptive feedback and advanced, high-precision pixel infrared temperature imaging have been developed. To use MRI or other equipment to monitor real time hyperthermia device however, it is necessary to combine a hyperthermia device with an MRI unit. This has proven to be difficult and costly since each device is functionally disturbed, if not damaged, by the presence of the other.

The exact molecular and cellular mechanism by which heat kills or inactivates tumor cells and microorganisms is unknown. Heat is an entropic agent and acts globally on every molecule constituting the cell. Heating is known to cause conformational changes in proteins, denature enzymes and affect cell membrane fluidity. By example, herpes simplex virus (type 1) thymidine kinase has a shortened half-life at 40° C. of only 30 minutes. The transforming gene product-enzyme of Rous sarcoma virus (protein phosphatase), a critical protein for cellular regulation, is totally inactivated in 30 minutes at 41° C. Hyperthermia is known to increase the formation of oxygen free radicals, including superoxide, hydroxyl, hydroperoxyl, hydrogen peroxide and lipid peroxides. These reactive oxygen species react indiscriminately and oxidize many organic molecules causing DNA damage, protein denaturation, lipid peroxidation and other destructive chain reactions. Acid microenvironments, known to exist in tumors and microorganisms with high rates of glycolysis (Embden-Meyerhof Pathway) and lactic acid production, favor protonation of the superoxide radical to form the highly reactive and toxic hydroperoxyl radical. Thus, thermal sensitivity of many tumors increases with decreasing intracellular pH. As compared to normal cells, many malignant and virally transformed cells have a reduced total functional capacity to withstand the increase flux of oxygen free radicals produced by hyperthermia.

On the intracellular level, moderate heating is known to activate phospholipase $A_2$, which increases the formation of pro-inflammatory mediators such as the leukotrienes, prostaglandins and eicosanoids. Heat also increases release of intracellular calcium through the stimulation of phospholipase C. Calcium cycling across the mitochondrial membrane appears critical to the increased production of oxygen free radicals. Increased intracellular calcium also inhibits the mitochondrial, anti-apoptotic Bcl-2 protein and induces the production of heat shock proteins, mediating thermotolerance. Heat injury to the intracellular tubulin network, lysosomes, Golgi bodies, mitochondria, and control of RNA splicing are some of the many known subcellular systems affected by heat. While the initial primary event leading to cell death by hyperthermia is unknown, a decrease in mitochondrial membrane potential followed by uncoupling of oxidative phosphorylation and generation of reactive oxygen species on the uncoupled respiratory chain are the first biochemical alterations detectable in cells irreversibly committed to apoptosis. The cytotoxic effect of hyperthermia is thus believed to be caused by numerous changes and complex damage to multiple vital cell functions. Those biochemicals altered by heat and essential to the function or viability of the cell are the pivotal targets of therapeutic heating.

The mode of hyperthermic cell injury is dependent on the severity of the heat stress, temperature and duration of heating. Moderate heating of 39°-42° C. is used therapeutically and is known to promote programmed cell death through apoptosis, an active process of selectively eliminating heat sensitive cells without inflammation, bystander-cell death or subsequent tissue fibrosis. Malignant and other transformed cells undergo apoptosis by suppression or activation of one or more genes such as bcl-2, c-myc, p53, TRPM-2, RP-2, RP-8, raf, abl, APO-11FAS, ced-3, ced-4, ced-9, etc. Drugs (methotrexate, cisplatin, colchicine, etc.), hormones (glucocorticoids), cytokines (tumor necrosis factor-alpha), radiation (free radicals) and hyperthermia can all initiate apoptosis. Increasing the temperature or duration of heating, or both, leads to cell death via necrosis. This physical process of indiscriminate cell killing is associated with inflammation and causes significant injury to normal, healthy cells.

For purposes of systemic hyperthermia, apoptosis of target cells is the therapy of choice. In the clinical setting it must be controlled under conditions of moderate heating so as to selectively differentiate and eliminate target cells with minimum toxicity to normal cells. Such controlled conductive heating by external technologies is inherently not possible. The thermal physical and thermophysiologic properties of cells vary and are dependent on their thermal conductivity, specific heat, density and blood perfusion among the various organs and tissues. Based on these properties, the actual temperatures at some of these sites are often 'partitioned', independent of one another and do not represent the monitored, mean "core" temperature achieved during therapy. Additionally, it is well recognized that it is the actual intracellular temperature increase, with it's associated internal physical and chemical changes, that is critical to the successful use of hyperthermia in exploiting the fundamental biochemical differences between normal and heat susceptible cells. Unfortunately, the initial cellular targets of all extracorporeal heating methods are the cell membrane and it's integrated proteins. The cell's internal contents, including mitochondria, compartmentalized enzymes, other organelles and any intracellular pathogens, etc., are progressively heated in sequence by thermal conduction from the outside-in. Thus, to sufficiently heat the interior of the cell, the external temperature must overcome the cellular and mitochondrial membranes, each composed of a lipid bilayer that acts as an effective thermal barrier.

By necessity, therefore, prior art heating methods require high external temperatures to establish a sufficient gradient to overcome the nonisotropic and non-homogeneous conductive heat loss between internal tissues and the insulating barrier of the cellular and mitochondrial membranes. For example, the Organetics PSI® (perfusion system (now First Circle Medical Inc.) device has to heat blood externally to 480 C (118.40 F) before returning it directly into the vascular system of the patient. Other extracorporeal circuit perfusion devices need to achieve ex vivo temperatures of 490 C (120.20 F.). Animal studies require temperatures of 540 (129.10 F) during the induction phase to achieve adequate target tissue temperatures. Safety in such prior art is therefore limited by the incipient destruction of surrounding tissues at the sites of the high temperature phases of heating. When lesser temperatures are attempted, effectiveness is compromised by either inadequate temperatures or duration of beating or development of thermotolerance. As a result, only regional hyperthermia has been widely used clinically and only in combination with more traditional techniques such as radiation and chemotherapy. Presently, none of the known heating technologies provide clinically safe and effective hyperthermia to treat systemic or disseminated disease. In order for systemic hyperthermia to become more widely used clinically, current heating methods must also overcome the use of labor intensive, complex equipment including invasive extracorporeal infusion and it's related toxicity problems to interposed tissues. Further, new hyperthermic technology must be compatible with noninvasive, real time thermometry.

The present invention avoids the problems of heat toxicity, inadequate target tissue heating, excessive cost, surgery, anesthesia and incompatibility with noninvasive temperature measuring devices: problems that are inherent to all therapeutic methods that deliver heat extracellularly, from the outside-in. This invention is an intracellular, therefore, an intracorporeal heating system which has additional distinct advantages. First, the human body is biochemically and physiologically designed to tolerate higher temperatures when heated from the inside-out as opposed from the outside-in. By example, in comparison to extracorporeal heating, which can safely generate a maximum body core temperature of 42° C. (107.6° F.), intracorporeal hyperthermia caused by strenuous exercise induces physiologic temperatures of up to 45° C. (113.0° F.) in muscle and liver with body core temperatures of up to 44° C. (111.2° F.). Exertional heat stroke patients have survived rectal body temperatures as high as 46.5° C. (115.2° F.) without any permanent clinical sequela. While the critical maximum temperature humans can tolerate is unknown, physiologic hyperthermic temperature induced under controlled conditions with adequate hydration have not shown any permanent untoward effects. Liver biopsies from subjects with such temperatures have not shown any significant microscopic abnormalities. Second, since heating with the present invention is chemically induced from within the cell, the actual intracellular therapeutic temperature will be higher than the measured core temperatures. As a result, intracellular organelles, including mitochondria, are heated at higher temperatures, undergo greater uncoupling and generate an increased flux of reactive oxygen species. Since oxygen free radicals, including superoxide, enhance and probably mediate the effects of hyperthermia, an improved therapeutic gain will be obtained at lower body core temperatures. Further, it is known that for each 0.5 degree Celsius increase in body temperature the metabolic rate and oxygen consumption increase 7%. Such an increase will assist heating the body in itself. Third, safety and control of temperatures with the present invention is far superior to that of exogenous methods. The body is naturally designed to dissipate heat from the inside-out. This is evident from the fact that a temperature gradient of 3.5°-4.5° C. exists between the visceral core and the skin. This gradient represents the transfer of heat from regions of high temperature to regions of low temperature, with ultimate heat loss from the skin to the environment through conduction, convection, radiation and sweat induced evaporation. The margin of safety and control represented by the 'feedback gain' of this intact physiologic heat dissipating system is extremely high, approximating 27-33. This rate of cooling can balance an influx of heat in a naked human body in a dry room at about 120° C. (248.0° F.). Thus, the human heat flow system permits the body to rid itself of excess endogenous heat very quickly and effectively. As a result, there is a wide margin of safety in case the target temperature is exceeded. In contrast, exogenous heating contravenes the natural physiologic flow of heat and its dissipating mechanisms. The natural heat dissipating mechanisms are overwhelmed and compromised. Control and safety over hyperthermia induced by extracellular means is thus fragile, with little room for error.

SUMMARY OF THE INVENTION

The present invention encompasses a composition and method using mitochondrial uncoupling agents, especially DNP, DNP with free radical producing drugs, DNP with liposomes, DNP conjugated to free radical formers, and DNP with other therapeutic pharmaceutical agents which are activated intracellularly by heat or reaction with mitochondrial electrons or free radicals to cause release of active medications for the treatment of cancer, HIV, other viruses, parasites, bacteria, fungi and other diseases. While not being bound by theory, it is submitted that the use of mitochondrial uncoupling agents, to increase intracellular heat and free radicals, as treatment for non-related cancers, viruses and other pathogens presupposes that the mechanism of action is non-specific for enzymes and receptors but is specific for interference with cellular and pathogen viability and induction of programmed cell death. The degree of intracellular heating, free radical formation, whole body hyperthermia and release of active drug molecules is controlled by the dose of DNP. Based on the quantity of oxygen consumed, the dose of DNP is adjusted to achieve the desired degree of hyperthermia. Safety and effectiveness is further controlled by manipulating metabolic rates of target tissues, duration of treatment and permissiveness of body cooling. In accordance with the present invention, intracellular, mitochondrial heat is generated by the use of DNP, other uncouplers, their conjugates, either alone or in combination with other drugs for the treatment of thermosensitive cancers such as non-Hodgkins lymphoma, prostate carcinoma, glioblastoma multiforme, Kaposi's sarcoma, etc; bacteria such as *Borrelia burgdorferi, Mycobacterium leprae, Treponema pallidum*, etc.; viruses such as HIV, hepatitis C, herpes viruses, papillomavirus, etc.; fungi such as *Candida, Sporothrix schenkii, Histoplasma, Paracoccidiodes, Aspergillus*, etc.; and, parasites such as *Leishmania*, malaria, *acanthamoeba*, cestodes, etc. 2,4-dinitrophenol was selected as the uncoupler of choice because it can be used at relatively high concentrations, permitting uniform distribution in organs and tissues. This invention also encompasses the use of DNP to selectively augment energy metabolism and heat production in inchoate malignant tumors for the purpose of increasing sensitivity of diagnostic positron emission tomography, temperature-sensitive magnetic resonance, and high-precision pixel temperature infrared imaging in differentiating normal from aberrant cell metabolisms. An additional object of the invention is the use of DNP to increase transcription of heat shock proteins, especially HSP 72, as a form of cellular pre-conditioning to decrease post-angioplasty restenosis, increase successful outcome of other surgeries, and facilitate antigen processing and presentation of immunogenic determinants on infectious agents, virally transformed cells and tumors so as to increase the natural or biologically activated immunological response.

In accordance with another aspect of the present invention, controlled thermogenesis with DNP is combined with other agents used to treat infectious, malignancy and other diseases. Examples of other agents include antifungal, antiviral, antibacterial, antiparasitic and antineoplastic drugs. Such drugs, including angiogenesis inhibitors and radiation have increased synergistic or additive activity when combined with hyperthermia in the treatment of cancer.

The method can be used for enhancing the sensitivity of positron emission tomography, nuclear magnetic resonance spectroscopy and infrared thermography in the diagnosis and monitoring of treatment of various diseases, including cancer. Similarly, the method can be used for enhancing the identification of unstable "hot" coronary and carotid artery plaques predisposed to rupture or undergo thrombosis. Such diagnostic and treatment monitoring methodology is based on the fact that most tumors have higher metabolic rates and generate more heat than normal tissues. Likewise, unstable atherosclerotic plaques are presumed to rupture because they have a dense infiltration of macrophages which have high metabolic rates and generate excessive enzymes and heat, causing the plaque to degrade and loosen. In both instances, controlled doses of DNP or other uncouplers can further increase metabolic rates and heat production to increase diagnostic sensitivity. Controlled heating with DNP and fibrinolytic recombinant tissue-type plasminogen activators can also be used therapeutically to accelerate fibrinolysis of clotted arteries.

In another aspect of the invention, DNP is administered in controlled and timed dosages to provide physiologic stress, "chemical exercise", so as to induce synthesis of autologous heat shock proteins (HSPs). Intracellular heat exposure associated with autologous HSP induction has a significant cytoprotective effect against ischemia and cellular trauma and acts as a form of cellular thermal preconditioning in patients about to undergo surgery. Induction of HSPs by DNP in patients some 8 to 24 hours prior to angioplasty, coronary bypass surgery, organ transplantation and other forms of high risk surgery, would provide for improved clinical outcome with decreased post-angioplasty intimal thickening or restenosis, increased myocardial protection from infarction, improved musculocutaneous flap survival in plastic reconstruction and reduced ischemia/reperfusion injury in organ transplantation cases.

Another aspect of the invention provides for controlled dosages of DNP to induce long duration (6 to 8 hour), mild whole body hyperthermia (39.0 to 40.0° C.) to afford maximum expression of immunogenic HSPs or peptides associated with HSPs. The antigenic properties of HSPs and HSP-peptide complexes, induced by DNP in infectious agents, especially those located intracellularly, or on tumors can be exploited to enhance the immune response. This aspect of the present invention provides a process for modulating the immune system of a patient with other therapies, comprising the steps of: (1) increasing the expression of HSPs by the process described above, and (2) administering humanized monoclonal or polyclonal antibodies, or (3) administering recombinant cytokines, lymphokines, interferons, etc., or (4) administering standard anti-infectious or anti-neoplastic therapy.

Additional objects and advantages of the invention will be set forth in part in the description of drawings that follows, and in part, will be obvious from the description, or may be learned by practice of the invention. The objects and advantages can be realized and obtained by means of the uses and compositions particularly pointed out in the detailed description of the preferred embodiments and in the appended claims.

BRIEF DESCRIPTION OF DRAWINGS

FIG. 2 depicts the conversion of pyruvic acid into acetyl CoA and the 2 carbon fragments entering the TCA cycle.

FIG. 8 depicts the effects of heating on mitochondrial uncoupling and correlation of uncoupling to superoxide free radical formation.

FIG. 11(*a*) shows the effect of body temperature on metabolic rate.

FIG. 12 shows six of the Hottest organs in the human body and their relative blood flow.

FIG. 14 shows a typical DNP induced hyperthermia patient monitored flow chart.

FIG. 15 shows a monitored patient flow chart after successive infusions of DNP and glucagon for treatment of parasitic disease of the liver.

FIG. 17 shows a patient flow chart after infusion of norepinephrine and successive intravenous doses of DNP for treatment of HIV disease. FIG. 17(*a*) depicts surrogate parameters relating to HIV disease before and after DNP treatment.

FIG. 18 shows a monitored patient flow chart after successive infusion of DNP for treatment of Lyme disease.

FIG. 19 shows a monitored patient flow chart using an alpha-1 adrenergic agonist with DNP to induce hyperthermia in a patient with disseminated cancer.

FIG. 21 shows the protective effects of DNP pretreatment on arterial catheter balloon induced injury.

FIG. 24 shows the effects of oral DNP on oxygen consumption prior to a patient undergoing a PET scan.

FIG. 25 shows a monitored DNP flow chart with incremental increases in oxygen consumption prior to a patient undergoing diagnostic thermography.

FIG. 26 shows a monitored patient flow chart using dinitrophenol and methylene blue for the treatment of prostate carcinoma.

FIG. 27 shows biochemical and clinical response of androgen-independent prostatic carcinoma to dinitrophenol and methylene blue treatment.

FIG. 28 shows a monitored patient flow chart using interferon-alpha and dinitrophenol for the treatment of chronic hepatitis C infection.

FIG. 29 shows the effects of dinitrophenol and interferon-alpha treatment on liver enzymes and hepatitis C viral loads.

FIG. 31 shows synthesis of an expanded combinatorial library of uncoupling agents.

DETAILED DESCRIPTION OF THE INVENTION

Electron transferring, transporting and energy converting elements are ubiquitous and are necessary for life. All eukaryotic and prokaryotic organisms depend on electron transferring and transporting elements such as metal containing hemes and nonmetal moieties such as flavins and adenine nucleotides. These biochemical entities convert the energy stored in chemical bonds of foodstuffs into cellular and organelle membrane potentials, high energy containing molecules such as adenosine triphosphate (ATP), creatinine phosphate, and other forms of chemical energy needed to maintain the highly negative entropic state of life.

The most common form of biologic energy is adenosine triphosphate (ATP). ATP is produced either anaerobically through the Embden-Myerhoff Pathway (glycolysis) or through oxidative phosphorylation. The latter, an oxygen dependent chemical energy conversion process, is generally associated with the Tricarboxylic Acid Cycle [(TCA), Krebs Cycle or Citric Acid Cycle]. The TCA cycle links the products of glycolysis to a multi-enzyme coupled series of electron carriers called an electron transport chain (ETS). The electron transport chain is coupled to production of ATP. The entire TCA cycle and oxidative phosphorylation process is located in intracellular organelles known as mitochondria.

Figure 1:
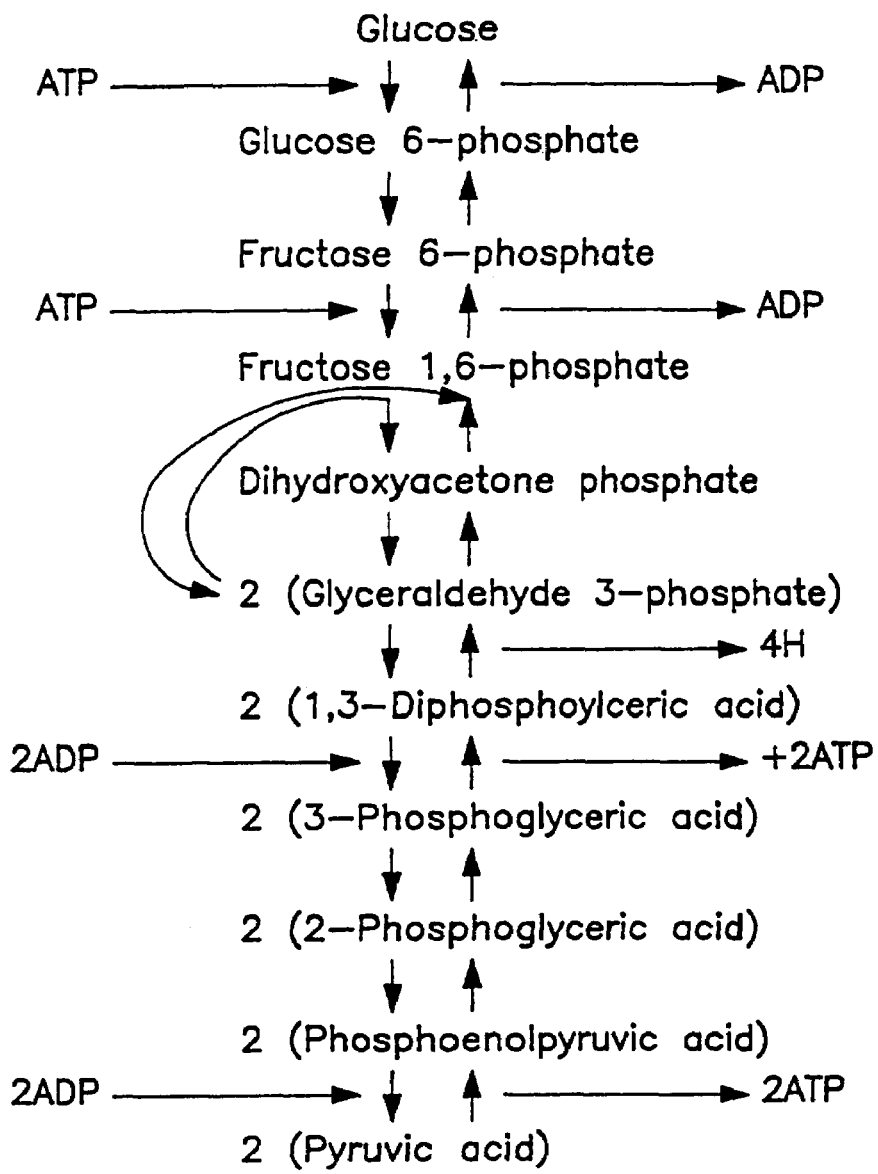
FIG. 1 shows features of glycolysis with formation of pyruvic acid and release of energy as heat.

While release of energy from foodstuffs can come about through a variety of biochemical means, the most important means by which energy release is initiated is by splitting glucose into two molecules of pyruvic acid. This occurs through the non-oxygen dependent process of glycolysis in a series of ten chemical steps depicted in FIG. 1. The overall efficiency of trapping energy in the form of ATP through this anaerobic process is 43%. The remaining released energy (57%) is discharged in the form of heat.

Pyruvic acid molecules derived from glucose, as well as end products of fat and protein breakdown, are transported into the mitochondrial matrix where they are converted into 2 carbon fragments of acetylcoenzyme A, FIG. 2. As depicted, these acetyl fragments enter the TCA cycle were their hydrogen atoms are removed and released as either hydrogen ions (H+) or combined with nicotinamide and flavin adenine dinucleotides (NAD+ and FADH) to produce large quantities of usable reducing equivalents (NADH and FADH2). The carbon skeleton is converted to carbon dioxide (CO2) which becomes dissolved in body fluids. Ultimately the dissolved CO2 is transported to the lungs and expired from the body. As noted in FIG. 2, the flux of reactants in the TCA cycle is always in the same direction because NADH and FADH2 is constantly removed as hydrogen is oxidized by the mitochondrial electron transport chain.

Figure 3:
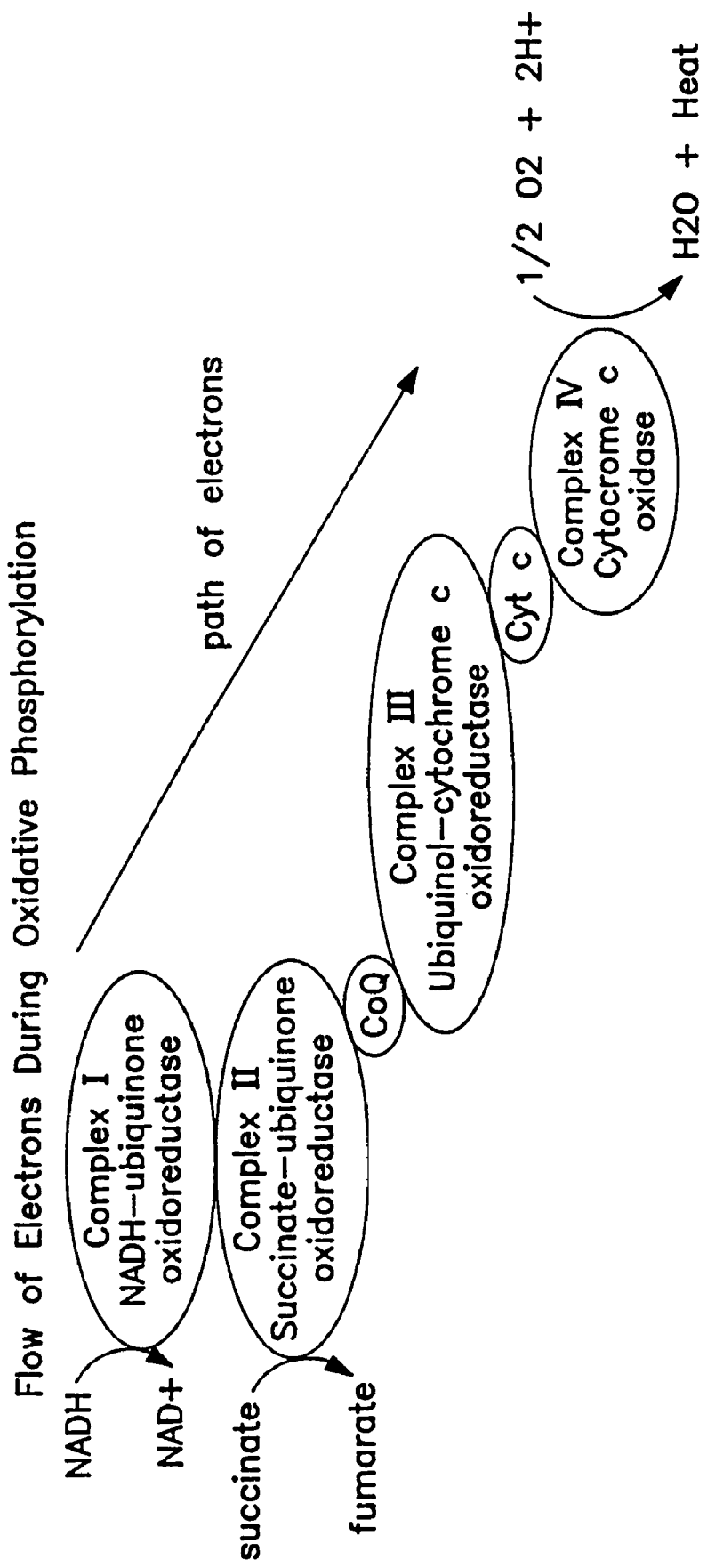
FIG. 3 shows the transfer of electrons down the electron transport chain during the process of oxidative phosphorylation
Figure 4:
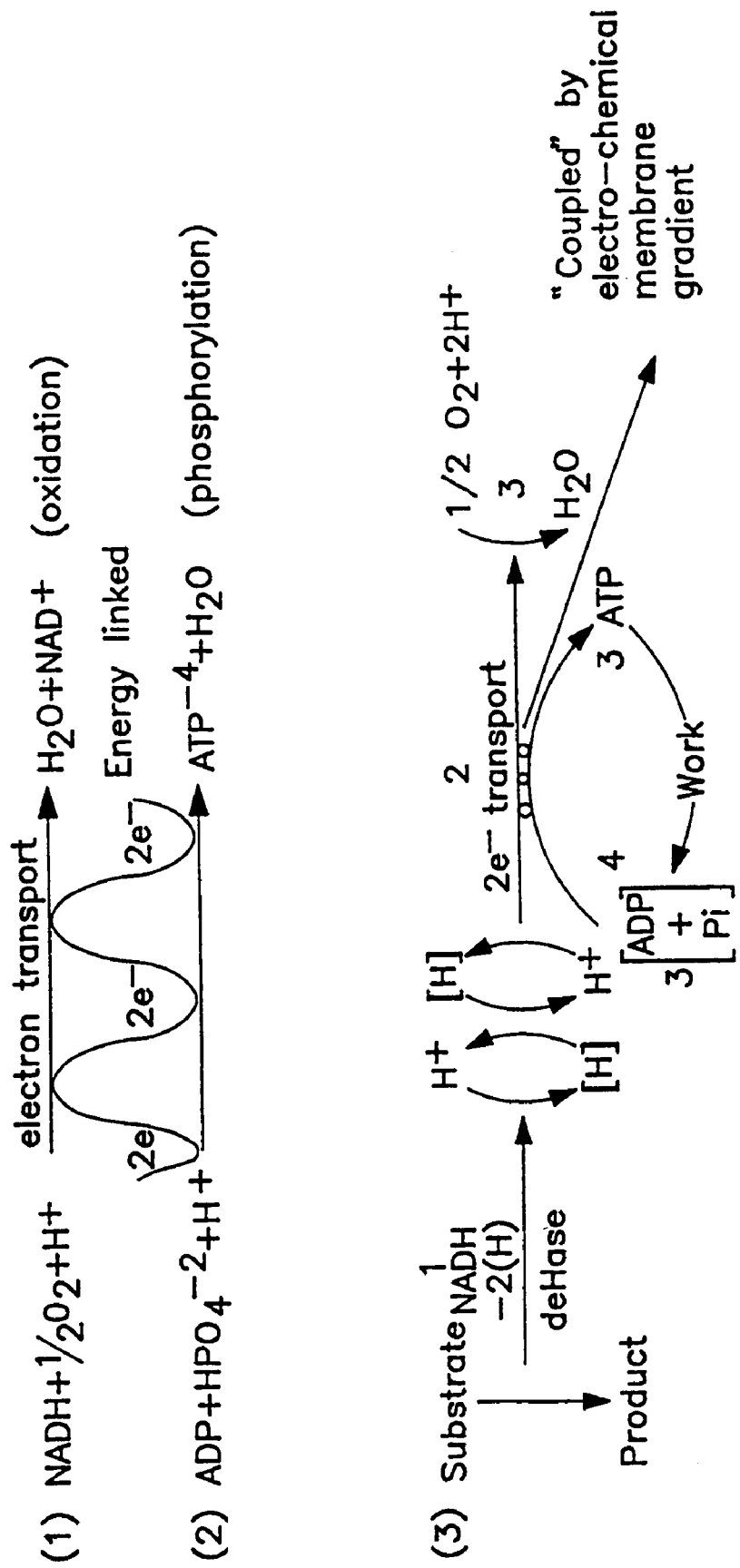
FIG. 4 shows oxidative phosphorylation as a coupling of two distinct processes, oxidation of reducing equivalents and formation of ATP. Both processes are "coupled" by an electro-chemical membrane potential created by electrons passing down the electron transport chain.
Figure 5:
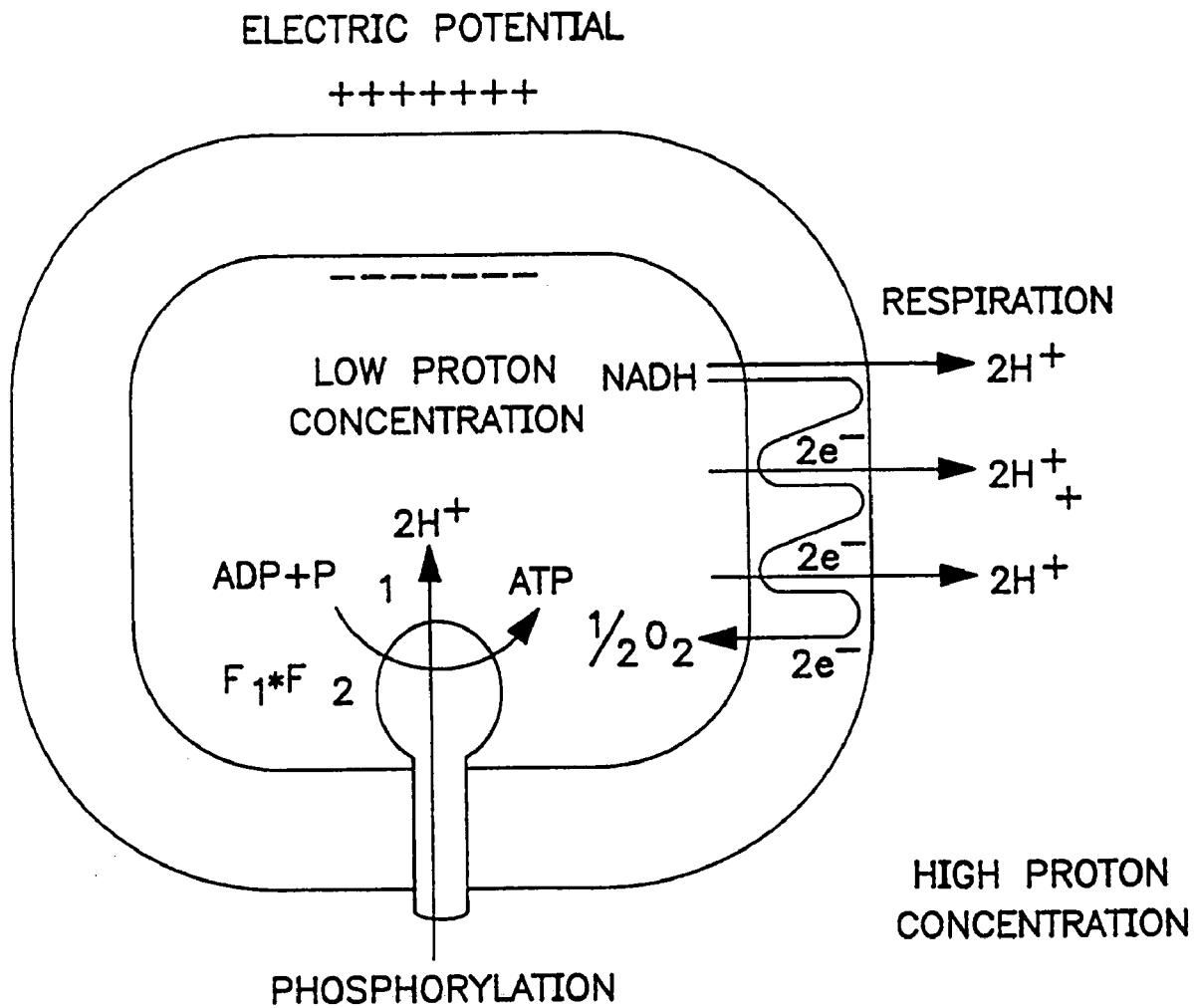
FIG. 5 shows the process of chemiosmosis. Electrons passing down the electron transport chain create energy to pump $H^+$ outside the inner mitochondrial membrane. This process creates a protonmotive force that causes formation of ATP by protons re-entering the membrane through ATP-synthase.

It is the electron transport chain that provides approximately 90% of the total ATP formed by glucose catabolism. During this process, known as oxidative phosphorylation, hydrogen atoms that were released during glycolysis, the TCA cycle, and converted to NADH and $FADH_2$, are oxidized by a series of enzymatic redox complexes (electron transport chain) located in the inner mitochondrial membrane, FIG. 3. Energy released in these steps is captured by a chemiosmotic mechanism that is dependent on the ultimate reduction of $O_2$ to form $H_2O$. As depicted in FIG. 4, oxidative phosphorylation is two distinct processes: (1) oxidation of NADH and $FADH_2$; and, (2) formation of ATP. Both processes are interdependent or "coupled" by a high energy linked proton ($H^+$, pH) gradient and membrane potential across the inner mitochondrial membrane provided by electrons as they pass through the electron transport chain. Energy released by the electrons pumps hydrogen ions ($H^+$) from the inner matrix of the mitochondrion into the outer inter-membrane space, FIG. 5. This process is known as chemiosmosis and creates a high concentration of $H^+$ outside the inner mitochondrial membrane and a powerful negative electrical potential in the inner matrix. This transmembrane proton gradient (protonmotive force) causes hydrogen ions to flow back into the mitochondrial matrix through an integral membrane protein (ATP synthase) to form ATP from ADP and free ionic phosphate. The efficiency of oxidative phosphorylation in capturing energy as ATP is about 69%. The remaining (31%) liberated energy is dissipated as heat. The overall efficiency of energy transfer to ATP from glucose via glycolysis, the TCA cycle and oxidative phosphorylation is 66% with about 34% of the energy being released as heat.

Heat is continually produced by the body as a byproduct of metabolism and eventually all energy expended by the body is converted to heat. On a thermodynamic basis, total body heat production is the algebraic sum of the enthalpy changes of all biologic processes in the body. The pathways are irrelevant, even though in the body oxidation involves numerous enzyme catalyzed reactions taking place at 37° C. Biochemically, approximately 95% of all the oxygen ($O_2$) consumed is used by mitochondria to stoichiometrically couple oxygen reduction to ATP and heat production via oxidative phosphorylation. The rate of $O_2$ consumption ($VO_2$) can be measured by indirect calorimetry and thus related to body heat production. Although this method does not include anaerobic processes such as glycolysis, indirect calorimetry is in close agreement with direct body heat measurements and it is generally accepted that 1 liter of $VO_2$ generates 4.825 Kcal (kilocalorie of energy), $5/6^{ths}$ of which can be detected as heat.

Figure 6:
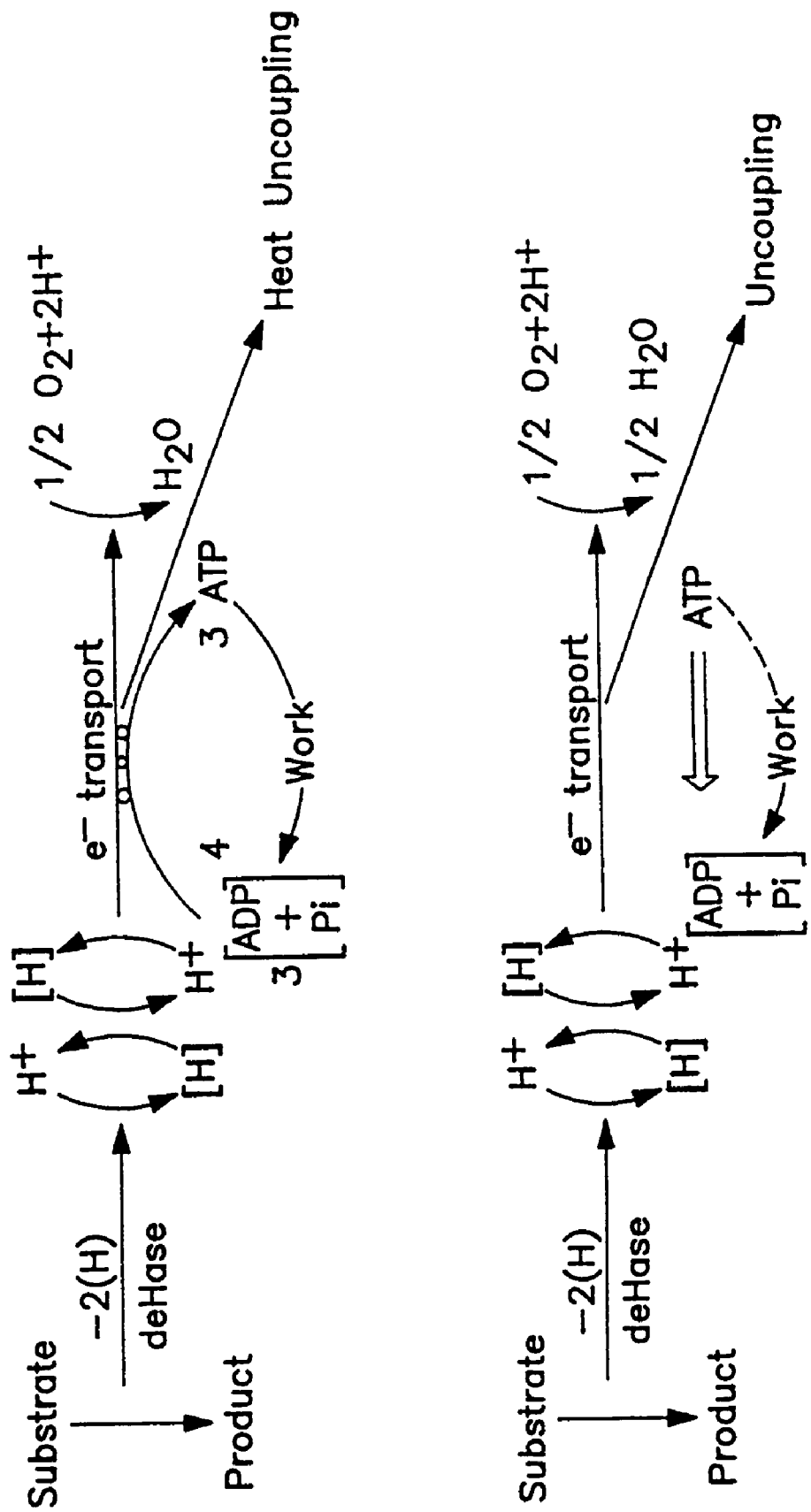
FIG. 6 depicts the uncoupling of oxidative phosphorylation through injury of the inner mitochondrial membrane.

In human adults, increased $VO_2$ and endogenous heat production can occur via muscular (work or shivering) and/or chemical [(cathecholamines, thyroid, etc.) non-shivering] thermogenesis. Whereas muscular activity can increase heat production 4-10 fold, non-shivering thermogenesis can only increase heat production by a maximum of 15%. However, oxygen consumption and non-shivering thermogenesis can dramatically increase when even mild injury to the inner mitochondrial membrane occurs so that it is no longer intact and protons leak or reenter the mitochondrion, uncoupled to ATP synthesis. Heating, endotoxin, osmotic imbalance, etc., can cause such injury, i.e., loss of coupling, with resulting respiration and ATP metabolism proceeding independently and maximally—respiration forward, phosphorylation in reverse. FIG. 6 compares normal coupled respiration and ATP formation to that which occurs when there has been injury to the inner mitochondrial membrane. The increased reduction of oxygen results in increased heat production.

Figure 6A:
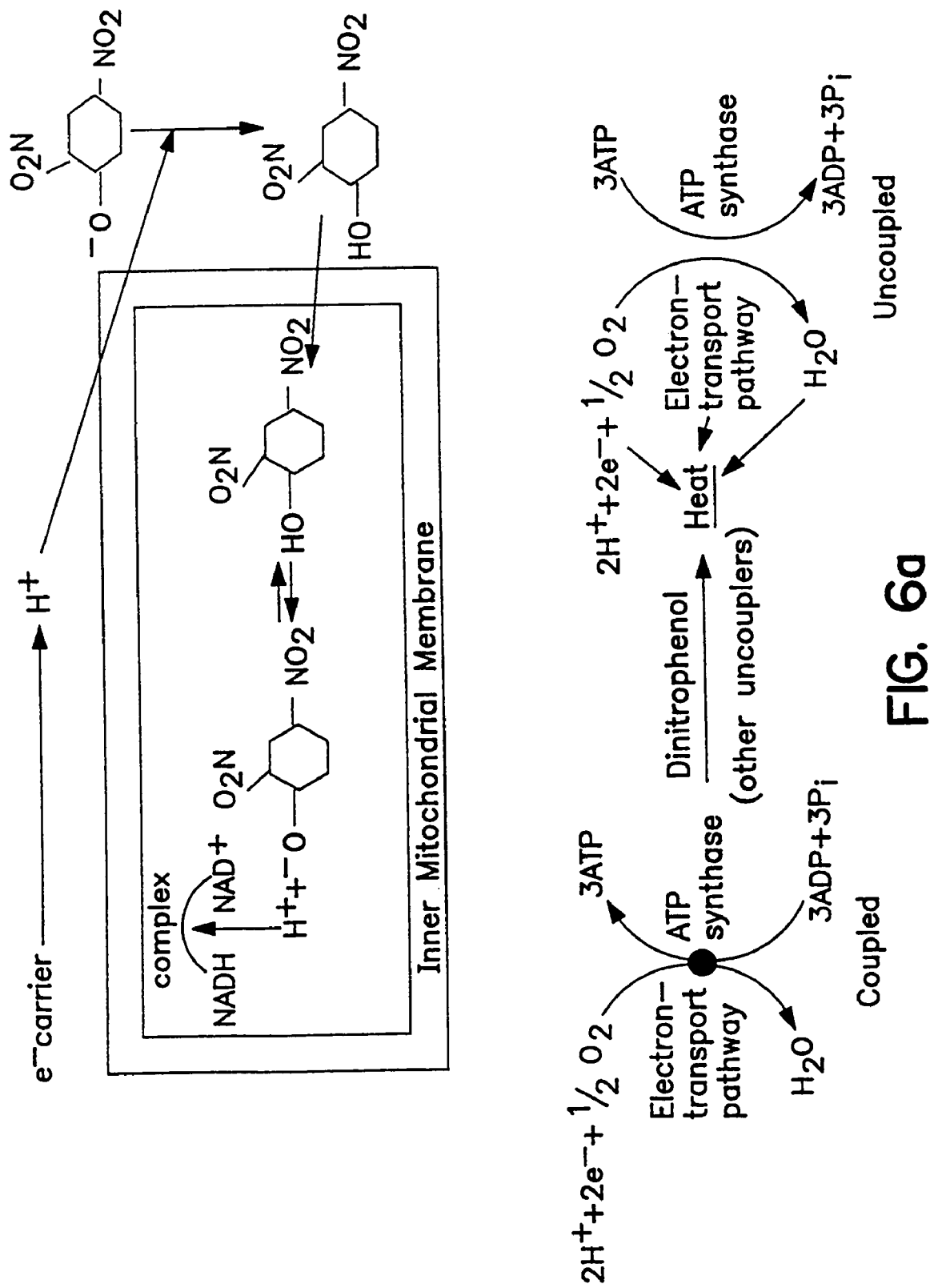
FIG. 6(a) shows how oxidative phosphorylation is uncoupled by DNP in intact and uninjured mitochondrial membranes.

Additionally, certain chemicals, including biologicals, can selectively increase the transport of protons across uninjured, intact inner mitochondrial membranes and dramatically increase $VO_2$ and heat production. These compounds dissipate the electrochemical-protonmotive transmembrane potential of mitochondria and uncouple the electron transport chain from ATP synthesis. FIG. 6(a) depicts one such uncoupling agent, DNP, cycling protons across an intact mitochondrial membrane. DNP and other uncouplers permit each of the two distinct processes involved in oxidative phosphorylation to "unlink" and increase their rates according to their own separate kinetic and thermodynamic signals, FIG. 6(b). Uncouplers increase respiratory rates, electron transport, $VO_2$, heat production and increased utilization of foodstuff substrates through glycolysis and the TCA cycle. Controlled doses of an uncoupler will increase $0_2$ consumption and heat production with minimal or no decrease in ATP levels because of intracellular equilibrium shifts in creatinine phosphate, oxidative phosphorylation reactants and increased production of ATP through the anaerobic, glycolytic pathway. Excess or toxic doses of virtually all uncouplers however, will produce secondary untoward effects, including decreased respiration, decreased heat production and eventual cellular death.

Figure 7:
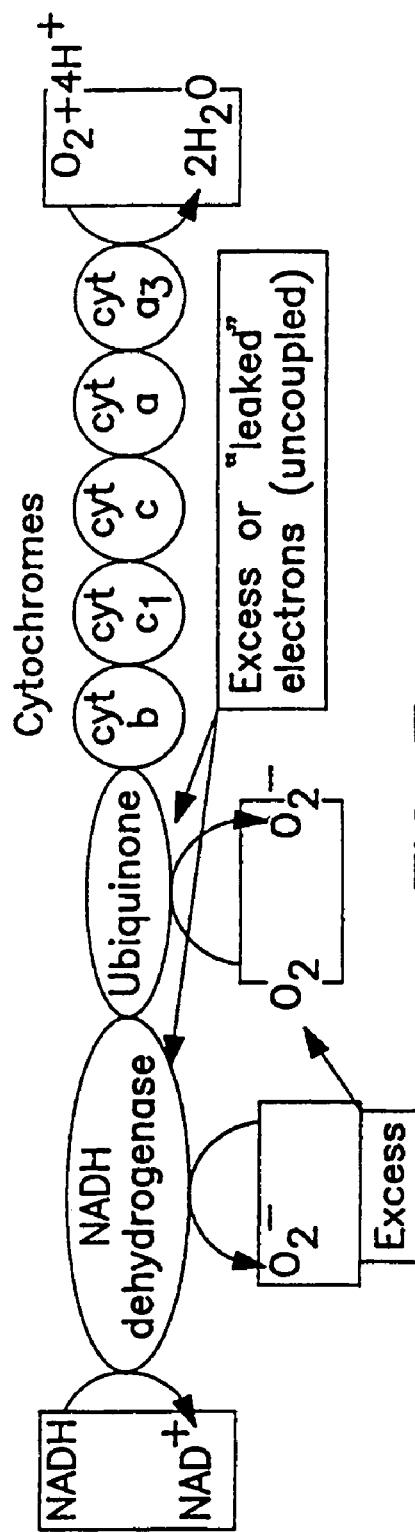
FIG. 7 shows the initial formation of superoxide radicals by the univalent reduction of oxygen in the electron transport chain.
Figure 7A:
FIG. 7(a) depicts the formation of hydrogen peroxide and hydroxyl radicals through the Haber-Weiss Reaction.
Figure 7B:
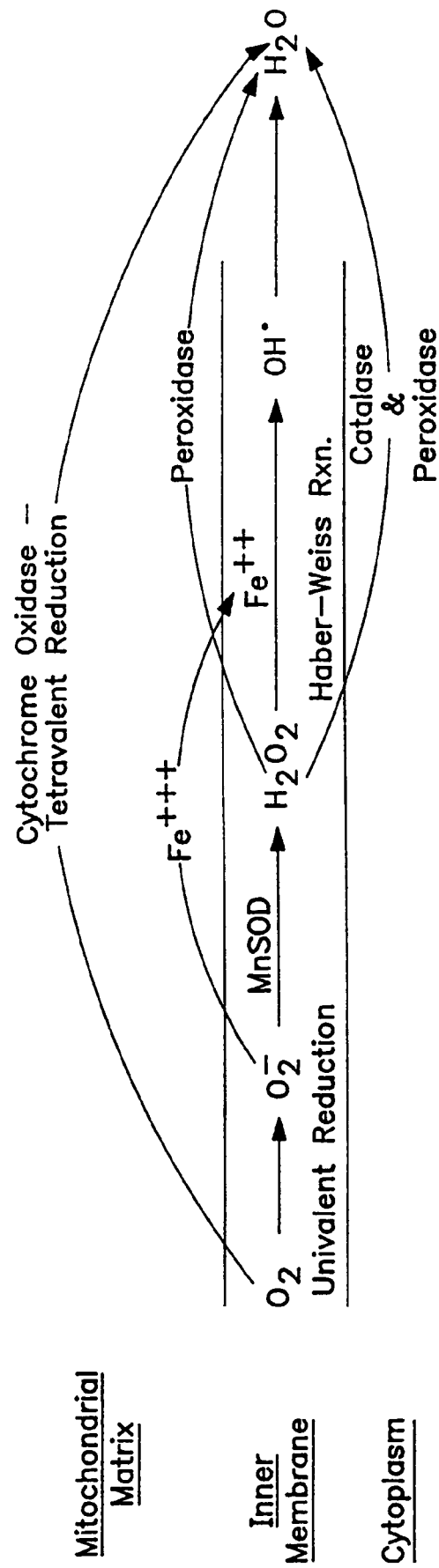
FIG. 7(b) shows an overview of mitochondrial oxygen utilization and free radical formation.

In addition to heat being a byproduct of oxidative phosphorylation, reactive oxygen species are also continuously produced by the mitochondrial electron transport chain. Free radicals of oxygen are produced during aerobic oxidation as electrons are transported by the electron carriers to ultimately reduce $O_2$ to $H_2O$. As depicted in FIG. 7, superoxide ($O_2^-$) radicals are generated by leaked electrons through the univalent reduction of oxygen. FIG. 7(a) shows that superoxide dismutase then converts the superoxide radical to hydrogen peroxide. Additional hydrogen peroxide ($H_2O_2$) and hydroxyl (OH.) radicals are formed through the Haber-Weiss Reaction, the hydroxyl radical being the most reactive species, reacting with any biologic moiety instantly. FIG. 7(b) depicts the overall scheme of oxygen metabolism and free radical formation at the level of the mitochondrion.

Figure 8A:
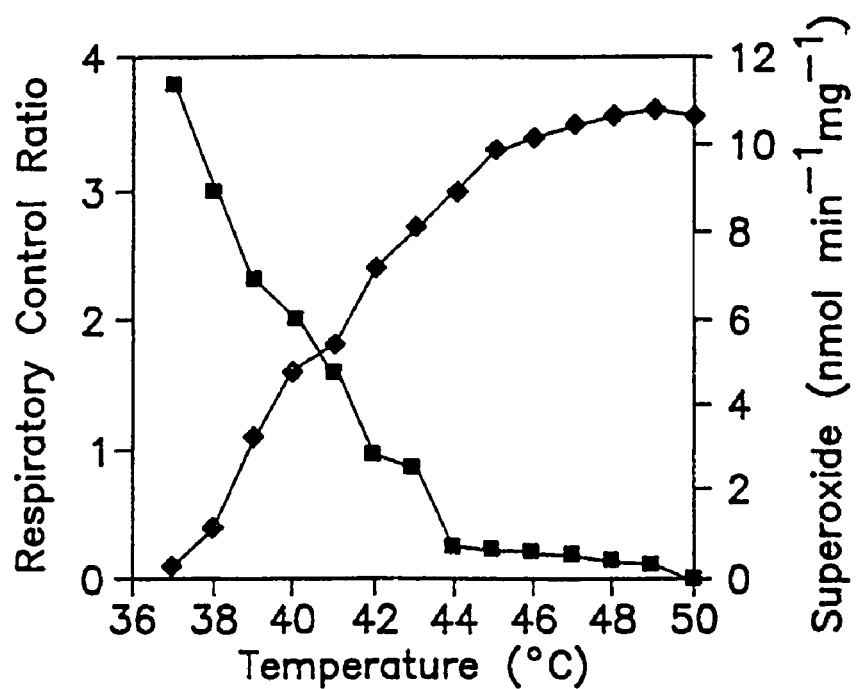
FIG. 8a shows the relationship between mitochondrial respiratory control ratio and superoxide production.
Figure 8B:
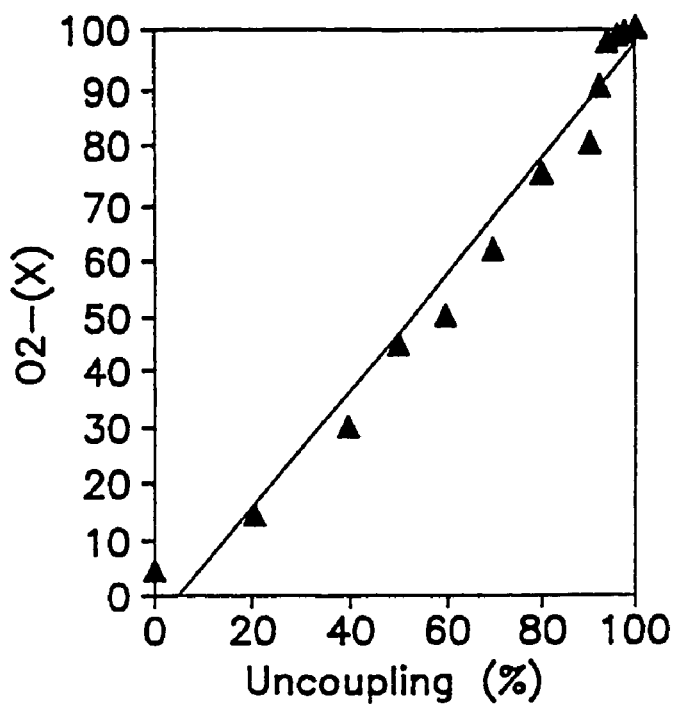
FIG. 8b shows the relationship between mitochondrial upcoupling and superoxide free radicals.
Figure 9:
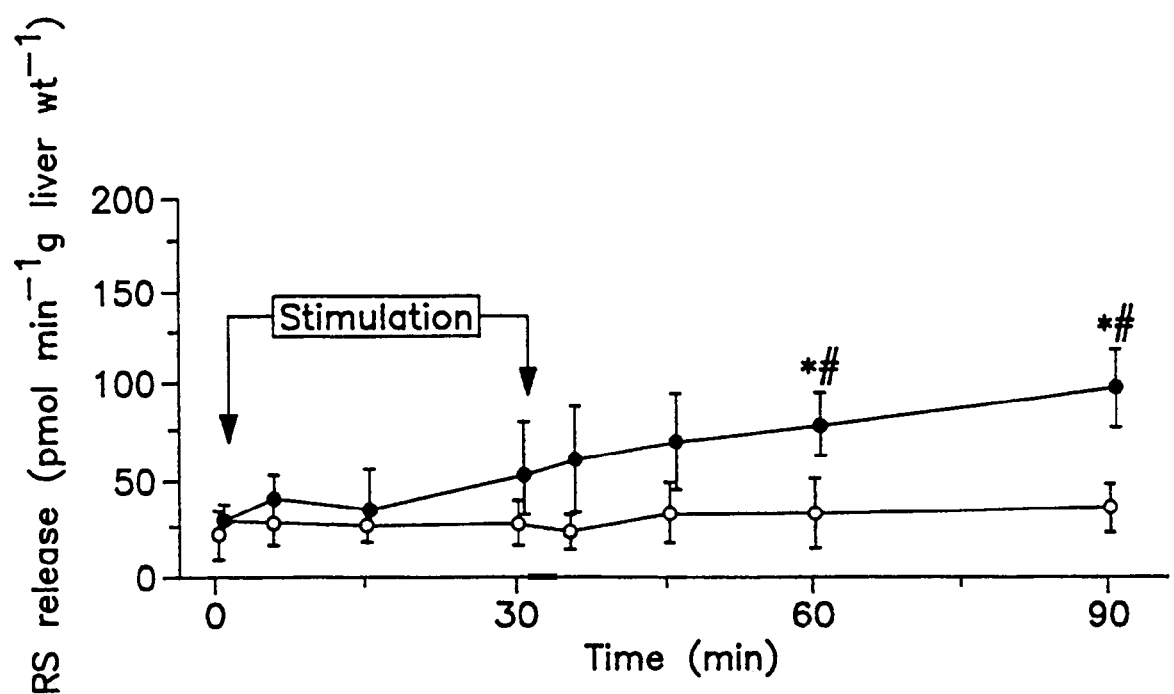
FIG. 9 depicts the increased formation of oxygen free radicals after cessation of DNP uncoupling and normalization of oxygen consumption.

As mitochondria become progressively heated, uncoupling occurs with increased flux of oxygen free radicals. The effects of heat on mitochondrial uncoupling and superoxide radical generation are depicted in FIG. 8. A linear correlation of 0.98 (P<0.01) is obtained for the relationship between percent uncoupling and percent superoxide generation. Similar to exercise increased body temperature and $VO_2$, hyperthermia induced by uncoupling agents appears to inhibit electron transport at the level of cytochrome c in the redox chain. Normal rat liver, infused with DNP, increases formation of reactive oxygen species threefold upon cessation of uncoupling, FIG. 9.

Generally, uncouplers are agents that are hydrophobic ionophores which bind protons and traverse biologic membranes to dissipate transmembrane proton (pH) and membrane potential gradients ($\Delta\Psi$, Delta Psim). In so doing, uncouplers increase the rate of metabolism (substrate utilization) in intact animals and isolated tissues by increasing the rate of oxygen reduction through increased availability of protons. $0_2$ consumption is increased and remains rapid as long as the mitochondrial respiratory (electron transport) chain attempts to overcome the effects of the uncoupler to maintain a pH gradient. Energy is still used to pump protons across the mitochondrial membrane, but the protons are carried back across the membrane by the uncoupler as depicted in FIG. 6(a). This creates a futile cycle and energy is released as heat. This chemical heat releasing process is comparable to heating that occurs when an electrical wire is "short circuited". Depending on the degree of external body heat dissipation, body temperature rises some 30 to 60 minutes after the increase in $0_2$ consumption. Onset of action is rapid after an intravenous injection of an uncoupler. Depending on the intravenous dosage, human oxygen consumption is increased in about 15-20 minutes and the intracellular heat production is increased proportionately. Metabolic rates as high as 10 times normal have been reported. Persistent increases in the metabolic rate can continue as long as 12 to 36 hours because of the long hydrophobic half-life of uncouplers in tissues. Temperature increases can be seen within 10 to 15 minutes in subjects whose heat dissipation mechanisms have been compromised. Heretofore, hyperthermia induced by uncoupling compounds has not been reported to have any therapeutic application.

While there are three general classes of uncoupling agents, each containing specific uncouplers of oxidative phosphorylation, the present invention utilizes 2,4-dinitrophenol (DNP) as the preferred embodiment. This is because DNP has been extensively studied. DNP was commonly used in food dyes in the late 1800's and in the munitions industry of World War I. Rapid increased respiration and hyperthermia, up to 49° C., was noted in man and animals that were accidentally intoxicated. Such dramatic physiologic effects by the dinitro-aromatic dyes, especially DNP, caused them to be inextricably tied to early and later modern studies of metabolism and bioenergetics. In the 1930's DNP was introduced into clinical medicine for the purpose weight loss. It was, however, sold as an over the counter secret nostrum and seriously misused. Had its long half-life in tissues been recognized and physician supervision implemented, it might have become an accepted drug. DNP has been reported in countless, different enzyme, cellular and metabolic studies. Review of such vast published studies have documented DNP's very specific mechanism of action as a proton ionophore, with all other effects a direct pharmacologic extension thereof. DNP is not mutagenic by the Ames and modified Ames tests; it has not been found to be carcinogenic or teratogenic; and, DNP blood plasma levels can easily be determined. DNP can be used at pharmacologic doses that achieve therapeutic concentrations in tissues. Further, DNP is stable, inexpensive and commercially available in reagent grade purity. It is understood however, that other uncouplers and combinations of other uncouplers with other drugs, hormones, cytokines and radiation can potentially be used under appropriate clinical settings and dosages to induce intracellular hyperthermia and promote additive or synergistic effects.

Figure 10:
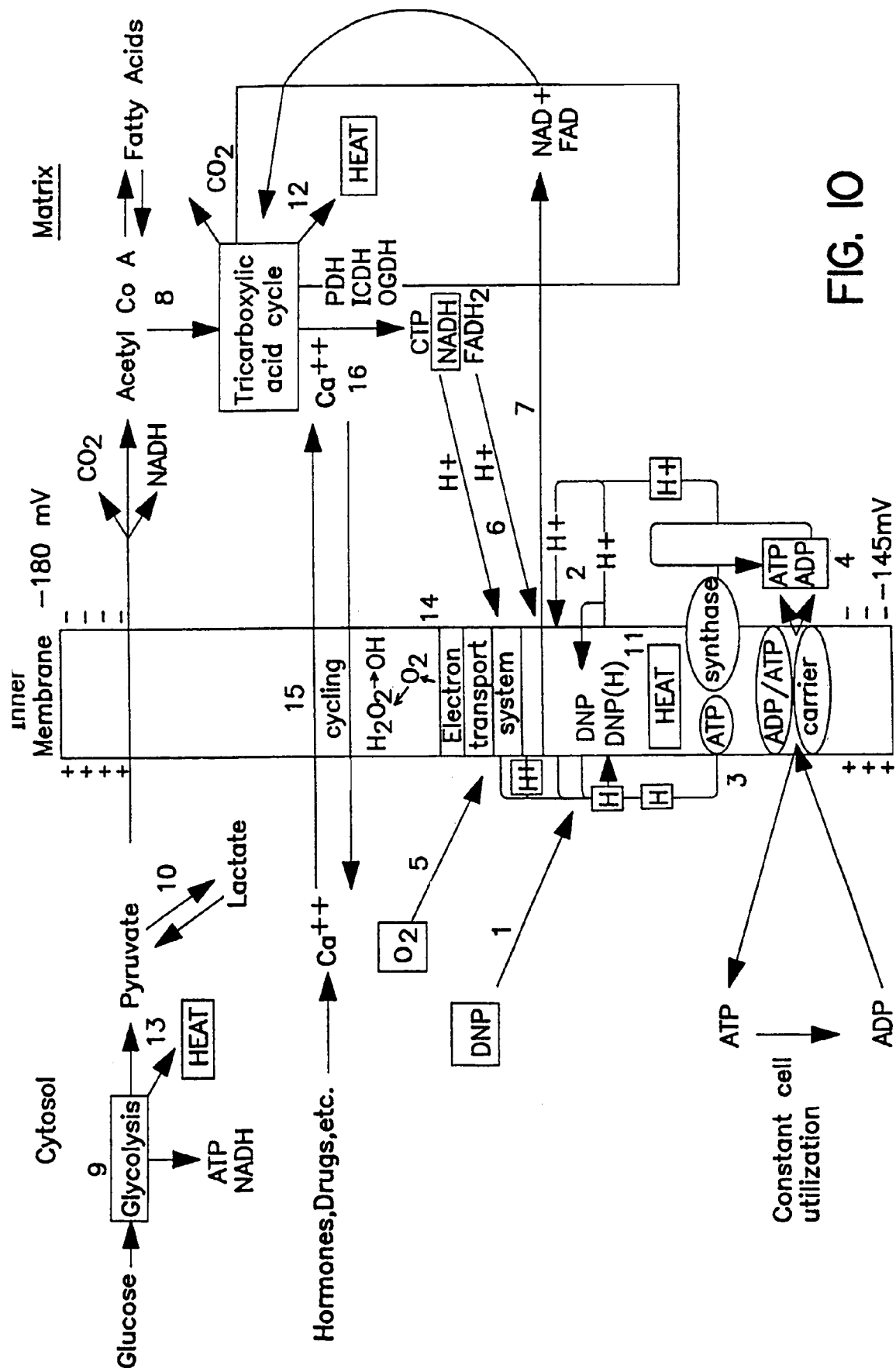
FIG. 10 shows the global intracellular effects of DNP, including the dominant foci of increased heat generation.

FIG. 10 shows the overall intracellular mechanism of action of DNP (and other uncouplers). Intracellular foci of increased heat and oxygen free radical flux are highlighted. Circled numbers in the figure indicate both direct and indirect effects of DNP: circled 1 and 2 effects shows that upon its intercalation into the inner mitochondrial membrane, DNP shuttles $H^+$ (hydrogen ions) across the membrane [see FIG. 6(*a*)]—this short circuits (de-energizes) the proton gradient established by the $H^+$ pumping action of the mitochondrial electron transport system (see FIG. 5). As a consequence, the inner mitochondrial membrane potential is lowered from −180 to −145 mV. Circled 3, 4, 5 and 6 effects shows that normal oxygen consumption and flux of NADH and $FADH_2$ (reducing equivalents) through the electron transport system is coupled to $H^+$ re-entry via mitochondrial availability of ADP for re-synthesis of ATP (see FIG. 4). By freely returning protons into the mitochondrial matrix without concomitant dependency on ADP to ATP reformation, DNP increases oxygen consumption proportionately to the degree of uncoupling. The rate of oxygen consumption remains linked however, to the flux of electrons provided by NADH and $FADH_2$ through the electron transport chain [see FIG. 6(*a*)]. NADH and $FADH_2$ utilization (re-oxidation) is concomitantly increased. Circled 7, 8, 9, and 10 effects show that oxygen use and electron transfer proceed at increasing rates to accelerate proton pumping against the added hydrogen ion load introduced by DNP. As a result, NADH and $FADH_2$ is continually depleted by re-oxidation to $NAD^+$ and $FAD^{++}$. The high "oxidation pressure" of $NAD^+$ and $FAD^{++}$ increases substrate oxidation and flux of 2 carbon segments through the tricarboxylic acid cycle (TCA). Augmented acetyl-CoA consumption in turn is maintained by an increased rate of glycolysis by depletion of pyruvate. If oxygen delivery is inadequate, or the dose of DNP excessive, the concentration of reduced NADH increases, pyruvate oxidation through acetyl-CoA and the TCA cycle is inhibited and lactic acid will accumulate. Lactate is also overproduced when cellular hypoxia is not present per se but glycolysis exceeds pyruvate oxidation. Such intracellular lactic acidosis exists in neoplastic cells, when there is lack of insulin, when fructose is infused and in other conditions or use of drugs which augment glycolysis and/or inhibit the mitochondrial electron transport system. While it is understood that the intracellular heat generated by DNP is the algebraic sum of the enthalpy changes from all the metabolic processes within the cell, effects circled as 11, 12 and 13 depict the most significant intracellular foci of heat generated by DNP. Intracellular and total body hyperthermia results when DNP releases energy at a rate faster than it can be dissipated. Heat is generated mainly at the inner mitochondrial membrane (electron transport system), the TCA cycle and sites of cytoplasmic glycolysis. Initially DNP generates heat at the inner mitochondrial membrane by discharging a portion of the energy stored in its electrochemical gradient. Operationally, such heat is from the "chemical short circuit" created by DNP shuttling protons to the negative (matrix) side of the polarized inner mitochondrial membrane [see FIG. 6(*a*)]. By usurping controlled proton re-entry and energy capture as ATP from availability of ADP through ATP-synthase, DNP causes NADH and $FADH_2$ (higher concentrations of $NAD^+$ and $FAD^{++}$) reoxidation to occur at rates much higher than necessary for oxidative phosphorylation. This causes an increased fall of electrons through the electron transport chain with rapid reduction of oxygen to water (see FIG. 3). The resultant energy is released as heat within the mitochondrial membrane. The rate of heat production from the TCA cycle is increased as it operates at a higher flux to maintain depleting amounts of reduced NADH and $FADH_2$ used to reduce molecular oxygen. Flux of acetyl-CoA and all metabolites through the TCA cycle (see FIG. 2) is increased by activation of enzymes which sequentially degrade the hydrogen containing two carbon fragments to $CO_2$, NADH, $FADH_2$ and heat.

Glycolysis and its associated heat production in the cytoplasm is also increased by DNP. Glycolytic activity is increased by reduced concentration ratios of ATP to ADP, activating pyruvate dehydrogenase and phosphofructokinase respectively (see FIG. 1). These enzymes increase the rate of glucose catabolism to pyruvate and its conversion to acetyl-CoA for entry into the TCA cycle. Glycolysis is very "energy inefficient" in making up the energy equilibrium shortfall created by DNP. Uncaptured energy from the glycolytic exergonic reactions accelerated by DNP is released as heat in the cytoplasm DNP stimulated anaerobic heat production through glycolysis can oftentimes be greater than that produced by the mitochondria. By example, many tumors and normal fibroblasts treated with DNP increase heat production by 83%, with only a 36% increase in oxygen consumption. Glycolysis is known to contribute greater than 62% of the total heat produced by human lymphocytes. Circled effect 14 shows that the mitochondrial electron transport chain normally produces reactive oxygen species through the univalent reduction of oxygen [see FIG. 7, 7(*a*) & 7(*b*)]. Under physiologic conditions, 2 to 4% of mitochondrial oxygen is converted to superoxide. DNP induced partial uncoupling and mitochondrial heating increases reactive oxygen species production manifold. Cytochrome oxidase and reductase is known to be inhibited by heating of the electron transport system. As a result, heated mitochondrial membranes produce increased amount of oxygen free radicals when DNP induced uncoupling is stopped and oxygen consumption is normalized (see FIG. 9). Reactive oxygen species act in synergy with heat to alter proteins, induce membrane changes and initiate apoptosis in susceptible cells. Circled effects 15 and 16 shows the effects of DNP on intracellular calcium homeostasis. Normally calcium is stored in the mitochondrial matrix, being pumped by the energized mitochondrial membrane. By DNP directly de-energizing mitochondria, and indirectly inducing membrane heating and prooxidant stress, inner mitochondrial membrane permeability is non-specifically increased with calcium efflux and cycling. This activates intramitochondrial dehydrogenases to produce more reducing equivalents in the form of NADH and FADH2 to match increased energy demands. Heat production is increased as a byproduct from the augmented TCA cycle.

Other known uncouplers that are considered to be "classic", in the same category and act as DNP include clofazimine, albendazole, cambendazole, oxibendazole, triclabendazole (TCZ), 6-chloro-5-[2,3-dichlorophenoxyl]-2-methylthio-benzimidazole and their sulfoxide and sulfone metabolites, thiobendazole, rafoxanide, bithionol, niclosamide, eutypine, various lichen acids (hydroxybenzoic acids) such as (+)usnic acid, vulpinic acid and atranorin, 2',5'-dichloro-3-t-butyl-4'-nitrosalicylanilide (S-13), 3,4',5-trichlorosalicylanilide (DCC), platanetin, 2-trifluoromethyl-4,5,6,7-tetrachlorobenzimidazole (TTFB), 1799, AU-1421, 3,4,5,6,9,10-hexahydro-14,16-dihydroxy-3-methyl-1H-2-benzoxacyclotetradecin-1,7(8H)-dione (zearalenone), N,N$^1$-bis-(4-trifluoromethylphenyl)-urea, resorcylic acid lactones and their derivatives, 3,5-di-t-butyl-hydroxybenzylidenemalononitrile (SF6847), 2,2-bis (hexafluoroacetonyl)acetone, triphenyl boron, carbonylcyanide 4-trifluoromethoxyphenylhydrazone (FCCP), tributylamine (TBA), carbonyl cyanide 3-chlorophenylhydrazone (CICCP), 1,3,6,8-tetranitrocarbazole, tetrachlorobenzotriazole, 4-iso-octyl-2,6-dinitrophenol (Octyl-DNP), 4-hydroxy-3,5-diiodobenzonitrile, mitoguazone (methylglyoxal bisguanylhydrazone), pentachlorophenol (PCP), 5-chloro-2-mercatobenzothiazole (BZT-SH), tribromoimidazole (TBI), N-(3-trifluoromethylphenyl)-anthranilic acid (Flufenamic acid), 4-nitrophenol, 4,6-dinitrocresol, 4-isobutyl-2,6-dinitrophenol, 2-azido-4-nitrophenol, 5-nitrobenzotriazole, 5-chloro-4-nitrobenzotriazole, tetrachlorobenzotriazole, methyl-o-phenylhydrazone, N-phenylanthranilic acid, N-(3-nitrophenyl)anthranilic acid, N-(2,3-dimethylphenyl) anthranilic acid, mefenamic acid, diflunisal, flufenamix acid, N-(3-chlorophenyl)anthranilic acid, carbonyl cyanide 4-trifluoromethoxyphenylhydrazone (FCCP), SR-4233 (Tirapazamine), atovaquone, carbonyl cyanide 4-(6'-methyl-2'-benzothiazyl)-phenylhydrazone (BT-CCP), ellipticine, olivacine, ellipticinium, isoellipticine and related isomers, methyl-0-phenylhydrazonocyanoacetic acid, methyl-0-(3-chlorophenylhydrazono) cyanoacetic acid, 2-(3'-chlorophenylhydrazono)-3-oxobutyronitrile, thiosalicylic acid, 2-(2',4-dinitrophenylhydrazono)-3-oxo-4,4-demethylvaleronitrile, relanium, melipramine, and other diverse chemical entities including unsaturated fatty acids (up to $C_{14}$ optimum), sulflaramid and its metabolite perfluorooctane sulfonamide (DESFA), perfluorooctanoate, clofibrate, Wy-14, 643, ciprofibrate, and fluoroalcohols. Additional unnamed classic uncouplers can include any analog which generally has a weakly acidic, removable proton and an electron withdrawing, lipophilic molecular body that is capable of charge delocalization. Hydrophobicity and capacity to exchange proton equivalents are integral features of classic DNP types of uncouplers.

A second class of uncouplers are ionophorous antibiotics. These molecules uncouple oxidative phosphorylation by inducing cation or anion influx across the mitochondrial membranes and diffusing back in a protonated form. As a result, chemical futile cycling ensues to reestablish the initial membrane potential. Liberated energy is dissipated as heat. Examples of ionophores that shuttle potassium ions ($K^+$) across membranes includes the antibiotics gramicidin, nigericin, tyrothricin, tyrocidin, and valinomycin. Nystatin shuttle sodium ions. The calcium ionophore, compound A23187, is a lipid soluble ionophore which mediates the electroneutral exchange of divalent cations for protons. Alamethicins, harzianin HA V, saturnisporin SA IV, zervamicins, magainin, cecropins, melittin, hypelcins, suzukacillins, monensins, trichotoxins, antiamoebins, crystal violet, cyanine dyes, cadmium ion, trichosporin-B and their derivatives are examples of uncoupling ionophores that depend on shuttling inorganic phosphate ($PO_4^=$) across the mitochondrial membrane.

Figure 11:
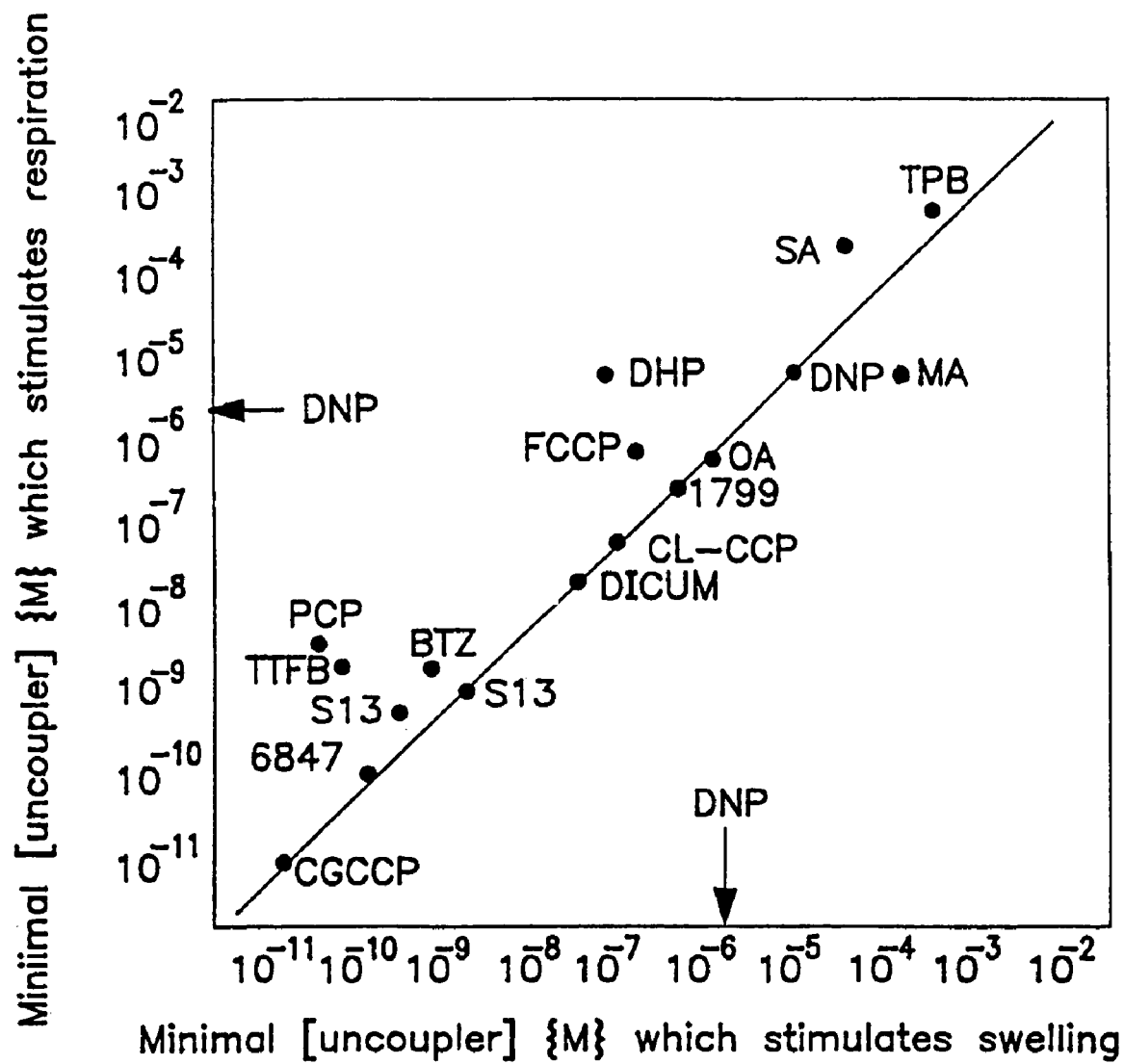
FIG. 11 shows the relative potencies of various uncouplers.

A third class of uncouplers is a group of heterogeneous compounds that dissipate the proton gradient by attaching or interacting with specific proteins in the inner mitchondrial membrane. Examples of such compounds include desaspidin, ionized calcium ($Ca^{++}$), uncoupling proteins such as UCPI-1, UCP-2, UCP-3, PUMP (Plant Uncoupling Mitochondrial Protein) histones, polylysines, and A206668-a protein antibiotic that ties up phosphoryl-transfer proteins. Examples and a potency comparison of a few uncouplers are depicted in FIG. 11.

Various conjugates, adducts, analogs and derivatives of the above mentioned agents can be formulated and synthesized to enhance intracellular uncoupling and heat production. Further, various covalent compounds of uncouplers may be synthesized as prodrugs, which upon, redox or reaction with free radicals within the cell will become activated to induce uncoupling, heat production and free radical cycling. Such derivatives and formulations may be desirable in the treatment of many tumors with higher mitochondrial membrane potentials and increased total bioreductive capacity. Uncoupling-free radical prodrug compounds may thus exert greater selective killing of transformed cells by undergoing a higher flux of reduction or electron acceptance in tumor cells. In this regard, the contents of U.S. Pat. No. 5,428,163 and the published methods of C-Alkylation of phenols and their derivatives by Hudgens, T. L. and Tumbull, K. D. are hereby incorporated by reference From a physico-chemical and thermodynamic standpoint, the amount of heat produced by uncoupling is proportional to the density and rate of flux of electrons through the mitochondrial electron transport chains. Such electron flux is initially reflected by the magnitude of the electrochemical proton gradient across the inner mitochondrial membrane. Those cells, tissues, organs and organisms that are metabolically more active will generally have an increased membrane potential and will respond with a greater amount of heat production for a given dose and type of uncoupler. FIG. 12 lists the six most "hottest" organs in the human body along with their rates of blood flow and rates of heat production. The actual amount of intracellular hyperthermia produced by an uncoupler is dependent on the uncoupler dose, its relative potency and availability of substrate such as glucose, glutamine, fatty acids or other substances that produce NADH or $FADH_2$. Oxygen and magnitude of the mitochondrial proton electrochemical gradient ($\Delta\mu H^+$) are additional factors that determine the amount of heat that can potentially be released by an uncoupler. Among all the constituents, $\Delta\mu H^+$ is the most clinically important. $\Delta\mu H^+$ is composed of the transmitochondrial membrane potential [$\Delta\Psi$ (charge difference)] and pH gradient [$\Delta$ pH ($H^+$ concentration difference)], $\Delta\mu H^+=F\Delta\Psi-2.3RT\Delta pH$, where, F=Faraday Constant, R=Gas Constant, and T=degrees Kelvin. Thus, $\Delta\mu H^+$ represents the potential amount of heat that can be liberated by an uncoupler when 1 mole of H⁺ is dissipated through the inner mitochondrial membrane. This potential heat energy is normally expressed in units of millivolts (mV) and is called the protonmotive force, $\Delta p = \Delta\mu H^+/F = \Delta\Psi - 2.3(RT/F)\Delta pH$. In vivo, $\Delta pH$ is generally 1 unit or less so that 75% or more of the total $\Delta p$ is comprised of $\Delta\Psi$. Consequently, the intracellular heat produced by an uncoupler can be estimated by the mitochondrial membrane potential ($\Delta\Psi$) alone.

Knowing the $\Delta\Psi$ is of practical importance because biopsy specimens may be incubated with cationic organic probes to estimate the $\Delta\Psi$ and the degree of differential heating that will occur between normal and transformed tissues. Dyes such as rhodamine 123, mitotracker green, calcein plus $Co^{++}$, $3,3^1$-dihexyloxacarbocyanine, triphenylmethylphosphonium, JC-1,$5,5^1,6,6^1$-tetrachloro-$1,1^1,3,3^1$-tetraethylbenzimidazolocarbocyanine, etc., all have an affinity for a negative mitochondrial $\Delta\Psi$. Based on the amount of cationic dye uptake, the membrane potential of specific tissue, tumors, and cells may be determined through the Nernst equation: $\Delta\Psi = -(RT/F)\ln(C_{in}/C_{out})$. Which at physiologic conditions and 37° C. is $=-61\log(C_{in}/C_{out})$, where $C_{in/out}$ is the concentration of the probe inside or outside the mitochondria and plasma membrane. By example, a 10 to 1 gradient=−60 mV, 100 to 1=−120 mV. Uncouplers dissipate the $\Delta\Psi$, generate heat and release or prevent uptake of cationic dyes. Six years of systematic measurement of mitochondrial membrane potentials have been performed on human and mammalian cells, including some 200 cell types derived from human malignant tumors of kidney, ovary, pancreas, lung, adrenal cortex, skin, breast, prostate, cervix, vulva, colon, liver, testis, esophagus, trachea and tongue. Based on this exhaustive study, a $\Delta\Psi$ difference of at least 60 mV is known to exist between normal epithelial cells and carcinoma cells. This is significant for the present invention in that uncoupling or "short circuiting" a 60 mV potential across a 5-nm mitochondrial membrane would be equivalent to the amount of heat generated by short circuiting 120,000 V across 1 centimeter. By exploiting or increasing the membrane potential between normal and transformed cells the rate of intracellular heat production by an uncoupler can be selectively increased in target tissues.

In order for uncoupler induced intracellular hyperthermia to be of therapeutic benefit, the development of thermotolerance is also taken into account in practicing this invention. Mammalian cells and prokaryotes acclimate and acquire transient resistance or thermotolerance to gradual or non-lethal hyperthermia. Such adaptation is believed to occur through increased synthesis of highly conserved groups of proteins known as heat shock proteins (HSP). The amount of HSP present in tissues, cells and organisms subjected to non-lethal heat, or other forms of prolonged metabolic stress, is proportional to their survival at higher temperatures. In general, thermotolerance develops after 3 to 4 hours of continuous hyperthermia, peaks in 1 to 2 days and decays back to normal thermosensitivity within 3 to 4 days. Thermotolerance is known to alter lethality of hyperthermia by as much as 2° C. increase or double the heating time required to achieve the same temperature-cytotoxic effect. Such adaptive thermoresistance by human tumors is problematic for continuous or fractionated cytotoxic treatment with hyperthermia. Induction heating times with the present invention are therefore kept to a minimum of 1 to 2 hours. Further, the uncoupler induced cytotoxic hyperthermia in the present invention induces relative tissue hypoxia, lowers intracellular pH and limits the production of ATP, all of which repress the development of thermotolerance. Low doses of uncoupler, which produce gradual heating can be used to induce HSP synthesis and promote thermotolerance.

Determining the amount of DNP in mg/kg of body weight required to produce the desired level of cytotoxic hyperthermia in a safe and efficacious manner is established from the thermal equivalents (Kcal) of oxygen consumed ($VO_2$), and the known average specific heat capacity of the human body. It is known that at standard temperature and barometric pressure, 1 liter of oxygen consumed per minute ($VO_2$) generates approximately 4.862 Kcal. It is also known that the average specific heat capacity of humans is about 0.83 of that required to raise 1 gm of $H_2O$ 1° K 4.184 J, a heat capacity of 3.47 J g $K^{-1}$. An initial estimate of the total energy required to be generated by DNP to induce 41.0° C. hyperthermia in 1 hour may be very simply determined from the above and customized for a specific patient as outlined below:

Patient Characteristics

Body weight 70 kg

Resting $VO_2$ 0.25 L/min

Basal energy expenditure 73.1 Kcal/hr (1754.4 Kcal/24 hrs.)

Basal core temperature 37.0° C.

Target temperature 41.0° C.

Required Energy to Raise Temperature to Target Level in 1 Hour (Weight in grams=$70\times10^3$) (human specific heat=3.47 J g $K^{-1}$) (Temperature increase=41.0°-37.0° C.)~$0.97\times10^6$ J. Since 1 J=$4.184\times10^{-4}$ Kcal, a total power input of about 232 Kcal would be required to raise the temperature of the patient to the objective level in 1 hour less that amount of heat generated by a heated metabolism outlined below.

Increase in Metabolic Rate/Heat Production with Increase in Body Temperature

Figure 11A:
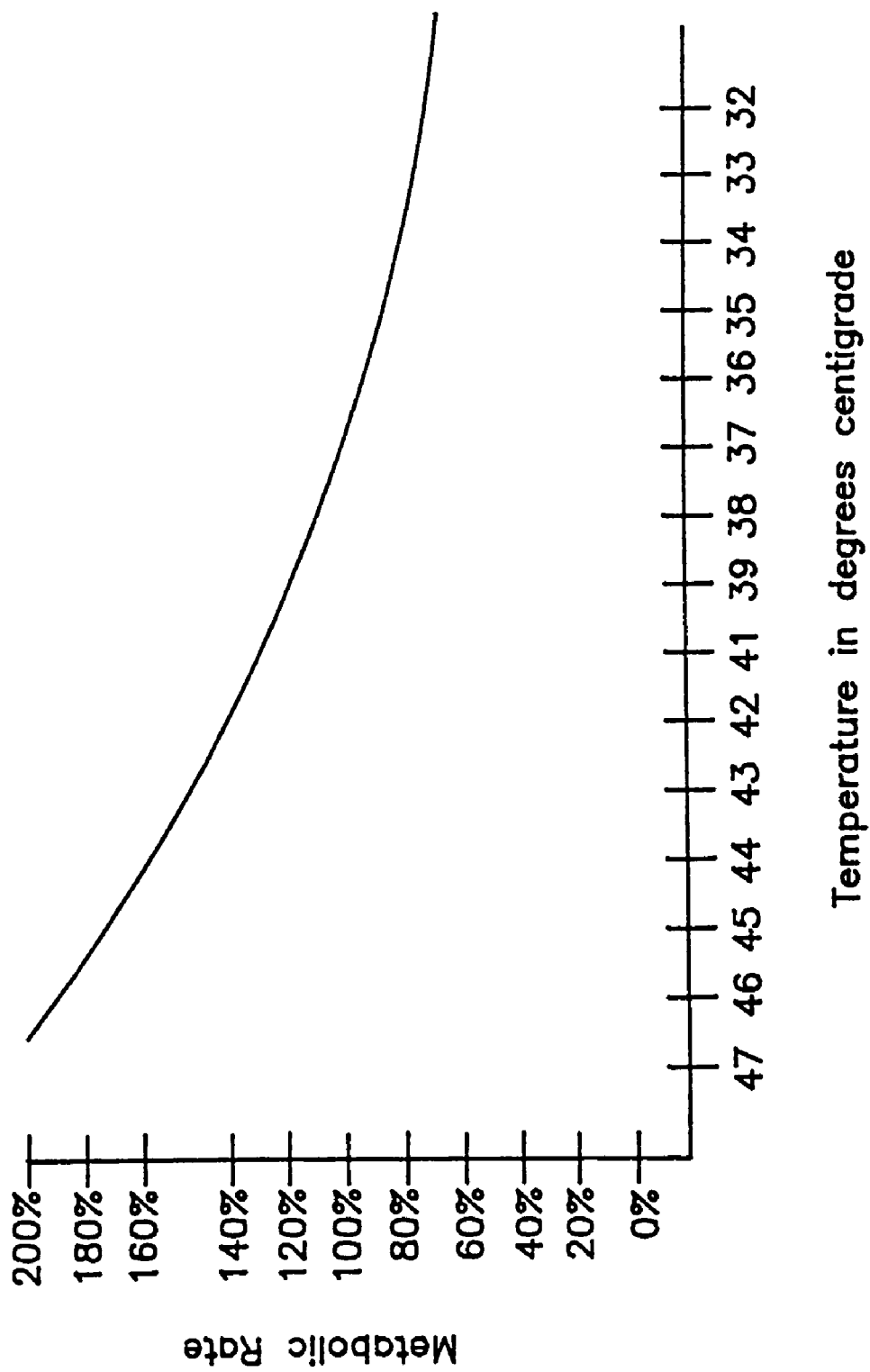

The basal metabolic rate (BMR) is known to increase in patients with endogenous fevers by approximately 7% for each 0.5° C. rise in temperature. This is graphically depicted in FIG. 11a. As a result, the increase in BMR relative to the temperature will in itself assist in achieving the objective level during the induction phase by the following equation:

$$BMR_{Tcore} = 73.1 \times 1.07^{(Tcore-37)/0.5}$$

Thus, at 41.0° C. the metabolic rate will be 134.4 Kcal/hr, 61.3 Kcal/hr above the basal energy expenditure level. This increase in metabolic rate will therefore reduce the initial energy required to heat the patient by approximately 61 Kcal over the 1 hour timeframe.

Initial Net Energy Input Required to Reach Target Temperature in 1 Hour

232 Kcal−61 Kcal (by increased BMR)=171 Kcal

Required Increase in Initial $VO_2$ to Obtain 171 Kcal Heat Input

Since the Kcal equivalent for 1 liter of oxygen consumed per minute is 4.862, then the initial increase in $VO_2$ required to generate 171 Kcal can be calculated as follows: Heat in Kcal/min=$VO_2 \times 4.862$. Since the individual patient has a resting $VO_2$ of 0.25 l/min which =73.1 Kcal/hour BMR, then $$X(VO_2) = 171 \text{ Kcal, or}$$

$$X = 0.25 \times 171/73.1$$

An initial minimal increase in $VO_2$ to approximately 0.60 l/min is required.

DNP Dosage Required to Increase $VO_2$ to 0.60 l/min

Figure 13:
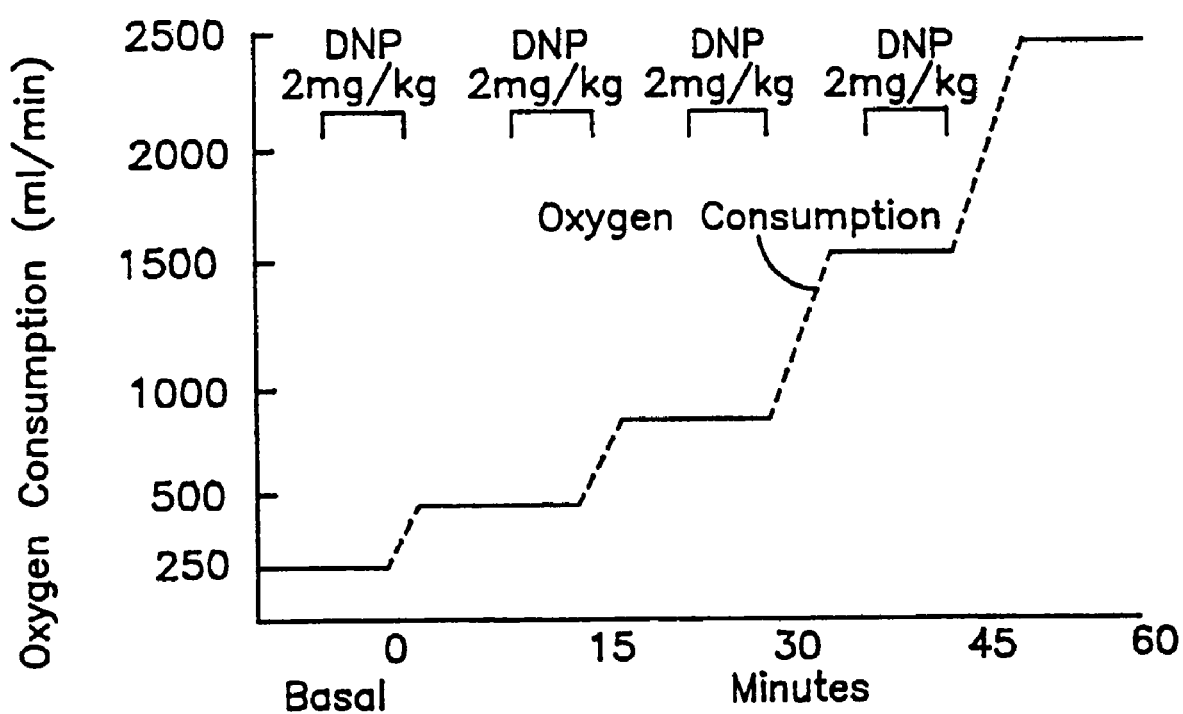
FIG. 13 shows the effect of successive doses of 2,4-DNP on oxygen consumption.

The individual DNP dosage (mg/kg) required to produce an increase in oxygen consumption to 0.60 l/min so as to achieve a 171 K/cal heat output is accomplished in the following fashion: (1) DNP is prepared in a 200 mg/100 ml sterile aqueous solution. If not fully dissolved, it can be brought into solution by buffering with 1% $NaHCO_3$, the pH must be kept below 8 to avoid hydrolysis; (2) the dose of DNP for each intravenous infusion can vary from 0.5 to 4 mg/kg and will depend on the clinical situation, as well as the initial and subsequent increases in the metabolic rate ($VO_2$). In an especially preferred embodiment, the patient is given an initial dose of DNP no greater than 1 mg/kg intravenously, infused over no less than a 2 minute period. Within approximately 10-15 minutes, a minimum of a 15% increase in $VO_2$ will occur. The $VO_2$ will continue to increase until a plateau is reached within an additional 5 to 10 minutes. After a 5 minute plateau in $VO_2$, a subsequent dose of either 0.5, 1, 2, 2.5, or 3.0 mg/kg DNP is administered and $VO_2$ is again increased until a desired plateau is reached. Additional infusions of DNP or other medications are administered under clinical parameters of $VO_2$, respiratory rate, pulse rate, blood pressure, urine output, cardiac output, core temperature, and clinical status of the patient so as to maintain safe and effective control of heating. If heat dissipating mechanisms are neutralized, measurable increases in core temperature will occur approximately 20 to 30 minutes after an increase in the $VO_2$. FIG. 13 illustrates the increases in $VO_2$ associated with repeated infusions of DNP.

Medications which increase the overall metabolic rate, or that of specific target tissues, and have short half-lifes can be utilized to increase the relative activity of DNP or other uncouplers to further adjust $VO_2$ and heat production. Examples of such medications are almost limitless because any drug, hormone or biologic response modifier that causes changes in enthalpy (heat content) during the course of its intracellular chemical and biophysical activity and interaction in the life cycle of biological cells can be utilized. A few illustrative examples include glucagon (half-life of 9 minutes in plasma), arbutamine (half-life 10 minutes), dobutamine (half-life 2 minutes), and vasopressin (half-life 5 minutes). Various amino acids and fatty acids, e.g., glutamine, proline, octanoate, etc., increase $VO_2$ by translocating reducing equivalents into the mitochondrial matrix via the malate-aspartate shuttle, B-oxidation or proline metabolism. Agents such as methylene blue (tetramethylthionine), ubiquinone, menadione, hematoporphyrin, phenazine methosulfate, 2,6-dichlorophenolindophenol, coenzyme Q1, CoQ2, or their analogs duroquinone and decylubiquinone, etc., can increase heat and/or free radical production by acting as artificial electron acceptors. Such agents, and numerous others, can be co-administered with DNP or other uncouplers to effectively increase the enthalpy changes in the entire organism or specific targeted tissues.

Minimizing Heat Loss and Temperature Control

Increased radiative and evaporative heat loss from man are the two most dominant thermoregulatory mechanisms for cooling the body. The body's methods of adjusting heat loss are vasoconstriction and vasodilation in the skins blood vessels. Radiation can account for 60% of the heat loss generated by the body, while evaporation by sweating at 1.0 liter/hour can represent a potential heat loss of about 1,000 Kcal/hour. By far, sweating and evaporation is the principal mechanism that dissipates heat under conditions that induce large heat gains. Depending on the clinical circumstances, heat loss due to evaporation, as well as radiation, can be managed and controlled by a variety of methods including, but not limited to, using vasoconstricting agents, placing the patient in a scuba diving wet suit, humidified survival suit, or enveloping the patient in a water soaked blanket covered or containing a polyethylene lining to prevent evaporative heat losses. Use of room ultrasonic nebulizers to induce continuous mist and high humidity is also known to prevent evaporative heat losses. Evaporative and radiant heat loss from the cranium is controlled by appropriate head gear, shower caps and/or wet towels. Control of local air velocities and management of surroundings as to temperature, emissivity, drafts, and convection currents are important to avoid large heat losses. In those clinical circumstances where total body hyperthermia is required, failure to adequately control body heat loss will necessitate using higher doses of DNP and induce a greater metabolic stress upon the patient.

If the core target temperature is exceeded or continues to rise after the target temperature is achieved, exposure of an extremity or body surface for a brief interval will permit sufficient heat loss to lower the core temperature to the target range. At target temperatures of 39-41° C., residual uncoupling by DNP will continue for approximately 3 hours. Heat production as a byproduct of glycolysis, and heated metabolism further maintains body heat content and compensates for any heat loss. Therefore, target plateau temperatures can be regulated with a large margin of safety and with little to no additional use of uncoupler. Therapy is terminated by removing the vapor barrier from the patient. Evaporative and radiant heat loss from the patient generally produces a fall in core temperature of about 2-2.5° C. in about 20-30 minutes. Obese patients and those with compromised thermoregulatory systems experience a slower falloff in temperatures.

Patient Monitoring, Fluid Support and Evaluation During Treatment

Placement of physiologic monitoring sensors, intravenous fluids, supplemental oxygen (4 l/min) and optional oral diazepam sedation (5-10 mg) is initiated prior to treatment. Patients receive 0.85 to 1.0 liter of intravenous (IV) 5% dextrose in 0.25 normal saline per hour alternated with 5% dextrose in 0.5 normal saline plus 7.5 to 10 meq of KCl per liter to insure a urinary output of no less than 1 ml/kg/hr. Oxygen consumption, caloric expenditure, rectal core temperature, cardiac rhythm, blood pressure, heart rate and respiratory rate are continuously displayed, monitored by a trained member of the treatment staff. The data is automatically downloaded into a computer every 20 seconds to 3 minutes for the entire procedure and immediately re-displayed on computerized graphs and charts. Two hours after treatment and 48 hours post-treatment, serum chemistries and hematologic profiles are repeated. A typical patient flow chart is depicted in FIG. 14.

Treatment of Excessive Heating and Antidotes

In those rare instances when too much uncoupler is administered or the metabolic rate of the patient unexpectedly increases and $VO_2$, hyperthermia, pulse rate and patient fatigue ensue, appropriate supportive measures of cooling, intravenous hydration and administration of specific medication should be instituted. Cooling should be instituted by uncovering the patient, spraying with tepid water and fanning with an industrial grade fan. If cooling is inadequate, surface, axillary and groin ice packs and intravenous cold glucose solutions should immediately be considered. Bicarbonate, 1-2 mEq/kg should be administered in the absence of blood gas analysis. Urine output of >1 ml/kg/hour should always be maintained to avoid pre-renal azotemia and oliguria secondary to possible rhabdomyolysis and myoglobinuria. Mannitol should be administered if urine output is inadequate. Hypoglycemia should immediately be corrected with 50% saturated intravenous glucose. If severe or persistent hypermetabolism ensues, rectal propylthiouracil-1,000 mg, hydrocortisone (100 mg q 6 h) or dexamethasone 2 mg q 6 h intravenously and/or sodium iodide as 1 g sodium ipodate (contrast agent) should be administered intravenously to induce iatrogenic hypothyroidism. The decreased metabolic rate will dramatically reduce the physiologic response to DNP. Patient agitation and restlessness can be avoided by appropriate IV or IM dose of diazepam. Salicylates are of no value and may contribute to further uncoupling. Medications that reduce sweating, e.g., tricyclic antidepressants, antihistamines, anticholinergics, phenothiazines, or decrease vasodilation, e.g., sympathomimetics, $\alpha$-agonists, or decrease cardiac output, e.g., diuretics, beta-blockers or induce hypothalamic depression, e.g., neuroleptics, $\alpha$-blockers, opioids, etc., should be avoided prior, during and immediately after treatment with uncouplers.

The hypermetabolic and hyperthermic activity of DNP can further specifically be reduced by using calcium channel blockers such as nifedipine, verapamil and others, in intravenous doses that do not cause a drop in blood pressure or induce cardiac arrhythmias. Dihydrobenzperidol (a neuroleptic drug with $\alpha_1$-adrenergic properties) can also be used to cause similar, significant reductions in DNP induced hypermetabolism and hyperthermia. Dosages of these anti-DNP agents are titrated in 5 mg to 30 mg increments and can be given either by mouth or intravenously. In those cases where DNP appears to decrease electrical conduction or cause EKG conduction abnormalities, Coenzyme Q10, in doses of 50 mg/kg, can be used to restore normal electrical activity.

Patient Selection and Pretreatment Evaluation

It is imperative that in the practice of this invention, patients be selected and evaluated prior to treatment. Recommended patient inclusion and exclusion criteria includes: (1) patients have a definitive histopathologic or other laboratory confirmed diagnosis of their disease; (2) the disease or condition should be responsive to intracellular hyperthermia treatment; (3) patients should have a Karnofsky score of 70% or greater; (4) not be pregnant; (5) weight should be within 45% (+/−) of ideal body weight and patients must weigh at least 35 kg; (6) there should be no history or findings of anhidrosis, scleroderma, ectodermal dysplasia, Riley-Day Syndrome, arthrogryposis multiplex, extensive psoriasis, serious dysrhythmias, malignant hyperthermia or neuroleptic malignant syndrome, pheochromocytoma, hypocalcemia, repeated episodes of hypoglycemia, chronic or recurrent venous thrombosis, alcoholism, renal failure, cirrhosis, untreated hyperthyroidism, anaphylaxis associated with heat or exercise-induced cholinergic type urticaria, exercise or heat induced angioedema, schizophrenia, catatonia, seizure disorders, emotional instability, Parkinson's disease, brain irradiation, cystic fibrosis, unstable angina pectoris, congestive heart failure, patients with cardiac pacemakers, severe cerebrovascular disease, spinal cord injury, severe pulmonary impairment, hereditary muscle disease such as Duchenne type muscular disease, central core disease of muscle, myotonia congenita, King-Denborough syndrome, Scwanry-Jampol syndrome, or osteogenesis imperfecta; (6) no immediate use of drugs that impair the body's heat dissipation mechanisms such as phenothiazines, anticholinergics, antihistamines, antiparkinsonians, glutethimide, hallucinogens, lithium, cocaine or other illicit drug use, monamine oxidase inhibitors, sympathomimetics, phencyclidine, opioids, phenylephrine, INH, tricyclic antidepressants, withdrawal from dopamine agonists, or cardiovascular drugs that clinically impair cardiac output or thermoregulatory vasodilation such as high doses of $\beta$-blockers, vasodilators, or calcium channel blockers; and, (7) the patient should not be anemic or otherwise have a reduced oxygen absorbing, carrying or utilizing capacity.

Pretreatment evaluation should include a complete medical history and physical examination focused on the selection criteria listed above. Laboratory evaluation should include pulmonary function tests-if indicated, full hematological survey with hemostatic profile, EKG, liver function tests, serum biochemical profile, thyroid panel, serum creatinine, calcium, phosphate, and stress-EKG or exercise-multigated radionucleotide ejection scan on patients whose cardiac ejection fraction is suspect not to be greater than 45% with probable deterioration on exercise. While clinical exceptions to entry laboratory values may exist, the following laboratory data should be a benchmark guide for initiation of treatment: hemoglobin$>=11.0$ g/dl for men and $>=10.0$ g/dl for women, platelet count$>=75.00$ platelets/mm$^3$, bilirubin$<=2\times$ULN (ULN=upper limit of normal), ALT (SGPT)$<=2\times$ULN, AST (SGOT)$<=2\times$ULN, pancreatic amylase$<1.5\times$ULN, neutrophil count$>=1,000$ cells/mm$^3$. Serum electrolytes and K$^+$ should be well within normal limits, as hypokalemia decreases muscle blood flow, cardiovascular performance, and sweat gland function.

More generally, the method outlined above is to be tailored to an individual patient. As set forth above, the DNP may be administered by intravenous infusion. Alternatively, the route of administration may also be orally, rectally or topically. The frequency and optimal time interval between administrations is individualized and determined by measuring V0$_2$, as well as other parameters. For example, various laboratory, x-ray, CAT scan, MRI, PET scan, HIV load, CD4+ lymphocyte counts, HSP expression, prostatic specific antigen (PSA) and other surrogate markers of clinical outcome can establish the VO$_2$, frequency and duration of therapy. One treatment, or treatments as frequent as every day, or every other day, as far apart as 1 year or longer may be required for sustained beneficial results.

The optimal VO$_2$, temperature, duration, and frequency between treatments will probably vary from patient to patient and the specific disease or condition being treated. One skilled in the art would be able to modify a protocol within the present invention, in accordance with standard clinical practice, to obtain optimal results. For example, the HIV relationships between viral load, CD4$^+$ lymphocyte counts, presence of opportunistic infections and clinical status of the patient can be used to develop more optimal regimes of DNP administration. Applicants' studies have revealed that the methods of the present invention can be effective in the diagnosis and treatment of a wide range of disease states and conditions in which uncoupler induced hypermetabolism, hyperthermia, oxidative stress and their sequela, play a beneficial role. To those skilled in the art, it is also encompassed that a variety of different veterinary, as well as medical, applications for treatment and diagnosis can be practiced with the present invention.

It is envisioned that DNP, or other uncouplers, may also be administered with other compounds used to treat infectious, malignant or other diseases. Examples of other agents include antifungal, antibacterial, antiviral or anti-neoplastic drugs, cell differentiating agents, and, various biologic response modifiers. Examples of anti-fungal agents include Amphotericin B, Griseofulvin, Fluconazole (Diflucan), Intraconazole, 5 fluoro-cytosine (Flutocytosine, 5-FC), Ketoconazole and Miconazole. Examples of anti-bacterial agents include antibiotics, such as those represented from the following classifications: beta lactam rings (penicillins), macrocyclic lactone rings (macrolides), polycyclic derivatives of naphthacenecarboxamide (tetracyclines), amino sugars in glycosidic linkages (aminoglycosides), peptides (bacitracin, gramicedin, polymixins, etc.), nitrobenzene derivatives of dichloroacedic acid, large ring compounds with conjugated double bond systems (polyenes), various sulfa drugs including those derived from sulfanilamide (sulfonamides, 5-nitro-2-furanyl compounds (nitrofurans), quinolone carboxylic acids (nalidixic acid), fluorinated quinilones (ciprofloxan, enoxacin, ofloxacin, etc.), nitroimidazoles (metroindazole) and numerous others. These antibiotic groups are examples of preferred antibiotics, and examples within such groups include: peptide antibiotics, such as bacitracin, bleomycin, cactinomycin, capreomycin, colistin, dactinomycin, gramicidin A, enduracitin, amphomycin, gramicidin J, mikamycins, polymyxins, stendomycin, actinomycin; aminoglycosides represented by streptomycin, neomycin, paromycin, gentamycin ribostamycin, tobramycin, amikacin; lividomycin beta lactams represented by benzylpenicillin, methicillin, oxacillin, hetacillin, piperacillin, amoxicillin and carbenacillin; lincosaminides represented by clindamycin, lincomycin, celesticetin, desalicetin; chloramphenicol; macrolides represented by erythromycins, lankamycin, leucomycin, picromycin; nucleosides such as 5-azacytidine, puromycin, septacidin and amicetin; phenazines represented by myxin, lomofungin, iodin; oligosaccharides represented by curamycin and everninomycin; sulfonamides represented by sulfathiazole, sulfadiazine, sulfanilimide, sulfapyrazine; polyenes represented by amphotericins, candicidin and nystatin; polyethers; tetracyclines represented by doxycyclines, minocyclines, methacylcines, chlortetracyclines, oxytetracylcines, demeclocylcines; nitrofurans represented by nitrofurazone, furazolidone, nitrofurantoin, furium, nitrovin and nifuroxime; quinolone carboxylic acids represented by nalidixic acid, piromidic acid, pipemidic acid and oxolinic acid. The Encyclopedia of Chemical Technology, 3rd Edition, Kirk-Othmer, editors, Volume 2 (1978), which is hereby incorporated by reference in its entirety.

Antiviral agents that can be used with DNP include: interferons α, β and γ, amantadine, rimantadine, arildone, ribaviran, acyclovir, abacavir, vidarabine (ARA-A) 9-1,3-dihydroxy-2-propoxy methylguanine (DHPG), ganciclovir, enviroxime, foscarnet, ampligen, podophyllotoxin, 2,3-dideoxytidine (ddC), iododeoxyuridine (IDU), trifluorothymidine (TFT), dideoxyinosine (ddi), d4T, 3TC, zidovudine, efavirenz, protease inhibitors such as indinavir, saquinavir, ritonavir, nelfinavir, amprenavir, etc., and specific antiviral antibodies.

Anti-cancer drugs that can be used with DNP include, but are not limited to, various cell cycle-specific agents represented by structural analogs or antimetabolites of methotrexate, mercaptopurine, fluorouracil, cytarabine, thioguanine, azacitidine; bleomycin peptide antibiotics, such as podophyllin alkaloids including etoposide (VP-16) and teniposide (VM-26); and various plant alkaloids such as vincristine, vinblastine, and paclitaxel. Anti-neoplastic cell cycle-non-specific agents such as various alkylating compounds such as busulfan, cyclophosphamide, mechlorethamine, melphalan, altretamine, ifosfamide, cisplatin, dacarbazine, procarbazine, lomustine, carmustine, lomustine, semustine, chlorambucil, thiotepa and carboplatin. Anticancer antibiotics and various natural products and miscellaneous agents that can be used with DNP include: dactinomycin, daunorubicin, doxorubicin, plicamycin, mitomycin, idarubicin, amsacrine, asparaginase, quinacrine, retinoic acid derivatives (etretinate), phenylacetate, suramin, taxotere, tenizolamide, gencytabine, amonafide, streptozocin, mitoxanthrone, mitotane, fludarabine, cytarabine, cladribine, paclitaxel (taxol), tamoxifen, and hydroxyurea, etc.

DNP can also be administered with various hormones, hormone agonists and biologic response modifying agents which include, but are not limited to: flutamide, prednisone, ethinyl estradiol, diethylstilbestrol, hydroxyprogesterone caproate, medroxyprogesterone, megestrolacetate, testosterone, fluoxymesterone and thyroid hormones such as di-, tri- and tetraiodothyroidine. The aromatase inhibitor, amino glutethimide, the peptide hormone inhibitor octreotide and gonadotropin-releasing hormone agonists such as goserilin acetate and leuprolide can also be used with DNP. Biologic response modifiers such as various cytokines, interferon alpha-2a, interferon alpha-2b, interferon-gamma, interferon-beta, interleukin-1, interleukin-2, interleukin-4, interleukin-10, monoclonal antibodies (anti-HER-2/neu humanized antibody), tumor necrosis factor, granulocyte-macrophage colony-stimulating factor, macrophage-colony-stimulating factor, various prostaglandins, phenylacetates, retinoic acids, leukotrines, thromboxanes and other fatty acid derivatives can also be used with DNP.

The use of this invention should be under the strict direction of a qualified and specialized treatment team to insure safety and effectiveness. The treatment team remains with the patient throughout the procedure to insure that safe and controlled dosages of an uncoupler are administered by monitoring real time changes in $VO_2$, metabolic rate, temperature, respiratory rate, heart rate, urine output and clinical status of the patient. This invention is practiced in controlled steps so as to attain a predetermined $VO_2$ and plateau of heating time for a particular disease or condition. For example, in cases were heat dissipation mechanisms do not have to be blocked, the specialized team will periodically recheck $VO_2$, heart rate, blood pressure, CAT scan, MRI, etc., and other laboratory and clinical parameters to insure continued safety and efficacy of DNP therapy. It is preferred that the specialized team undergo a training period in the use of this invention prior its administration to human patients.

The present invention is further illustrated by reference to the following examples, which illustrate specific elements of the invention but should not be construed as limiting the scope of the invention.

EXAMPLE 1

Method of Using DNP with Glucagon to Treat Parasitic Infections, Hydatid Disease of the Liver History: A 52 year old white Swiss male, European fox hunting dog trainer, presented with right upper quadrant pain and vomiting. Past history revealed he had hepatic "cyst" surgery 2 years ago. Preoperatively, he was treated with albendazole. Only one dose of albendozale was given because of a "near death" anaphylactic reaction. He denied history of weight loss, pulmonary, cardiac, neurologic or thermoregulatory problems. There was no history of alcohol abuse or medication use. The patient was adamantly opposed to any further surgery or treatment with albendazole or mebendazole.

Physical Examination Weight=90 Kg; height=177.8 cm; BP=140/80; HR=76 & reg; Resp.=18 min; T=37.0

An old well healed scar consistent with prior hepatic surgery was present. Physical exam otherwise was unremarkable.

Laboratory studies: EKG, chest X-ray, blood panel, including serum electrolytes, thyroid studies and liver function tests were within normal limits (WNL). A complete blood count was unremarkable except for 20% eosinophilia. Ultrasound and nuclear magnetic resonance revealed 4, 2 to 3 cm. in diameter, cysts in the right middle lobe of the liver and a solitary 2 cm semi-solid medullary cyst in the neck of the right humerus. ELISA serology showed a diagnostic titer for hydatid disease. Review of previous surgical liver pathology reports revealed a cestode compatible with *Echinococcus multilocularis*.

Clinical assessment and treatment evaluation: The patient had no historical or physical contraindications to DNP induced hyperthermia. Conventional therapy of hydatid disease is either surgical resection or medical therapy with albendazole for 4 weeks. Hydatid bone cysts are not amenable to surgery and respond poorly to standard medical therapy. *Echinococcus multilocularis* protoscoleces and the germinal membranes of hydatid cysts are known to be irreversibly destroyed by heating at 41° C. for 15 minutes. Human liver and hepatocytes can withstand artificial temperatures of 42° C. for as long as 20 hours without irreversible damage. Acute glucagon treatment is known to preferentially stimulate hepatocyte mitochondrial $VO_2$. Rates of hepatocyte uncoupled $VO_2$ are also know to be stimulated up to 100% in less than 6 minutes after the hormonal action of glucagon. Acute glucagon treatment has been shown to selectively increase the pH gradient across hepatocyte mitochondrial membranes. Thus, it can be empirically presumed that any increase in $VO_2$ from glucagon administration causes increased thermogenesis, predominantly in the liver.

Pretreatment protocol: the patient was given 10 mg diazepam by mouth and dressed into a modified wet suit. The wet suit was cut lengthwise at the arms and legs. Velcro strappings were attached at the cuttings for closure, rapid removal or exposure of the limb(s). After placement of monitoring sensors, he was started on IV fluids of 5% dextrose, 0.5 normal saline with 7 meq $K^+$, infused at an initial rate of 12 cc/kg/hr. Evaporative heat loss from the head was minimized by a plastic shower cap and towels. A 401AC temperature probe (YSI Incorporated, Yellow Springs, Ohio) was inserted 11 cm. into the rectum. The probe was connected to a Model 4600 telethermometer (YSI 4600 Precision Thermometer) and readings within 0.1° C. were continuously displayed and recorded at baseline and during treatment on Hewlett-Packard (HP) computer systems with customized software developed by MR&S (Manalapan, N.J.). A TEEM 100 Metabolic Analysis System (AeroSport Inc., Ann Arbor, Mich.), with a modified face mask and oxygen delivery system (38-40% $O_2$ saturation) for patient comfort and increased accuracy, was attached to the patient. Oxygen consumption ($VO_2$), carbon dioxide production ($VCO_2$), expired air volume ($V_E$), heart rate (HR), and Kcal of heat produced were measured in 20 second intervals and extrapolated to minute or hourly rates. All patient data was monitored in real time, continuously displayed at baseline and during treatment and recorded on HP computer systems with customized software from MR&S (Manalapan, N.J.).

Treatment procedure: After baseline recordings of 10 minutes, the required amount of DNP to raise the initial $VO_2$ to achieve a temperature in the patient of 40° C. was calculated as described under "DNP dosage required to increase $VO_2$". The patient was given an initial dose of 1 mg/kg of DNP, infused intravenously over a 3 minute period. After the $VO_2$ stabilized at 40% above baseline, an additional DNP infusion of 3 mg/kg was given. Upon attaining a stable $VO_2$, 0.5 mg of glucagon was administered intravenously. After this stabilization of $VO_2$, a glucagon drip was variably infused from 0.5 to 5 mg/kg/hour to additionally control $VO_2$ and selectively augment heat production in the liver. The treatment procedure was discontinued after the patient was maintained at a rectal body temperature of 40° C. for about 1 hour; The wet suit was opened and head covering removed. After the patient's body temperature reached 38° C., the Foley catheter was removed and intravenous fluids were discontinued. Evaporative and radiant heat loss lowered the body temperature to a normothermic level within 30 minutes. No immediate or delayed post-treatment toxicity was encountered. Monitored patient parameters are shown in FIG. 15.

Treatment outcome: Serial imaging studies revealed hepatic and bone cyst shrinkage with increased density at 2 and 4 weeks post treatment. Repeat magnetic resonance imaging at 4 months showed complete cyst disappearance in the liver and bone.

EXAMPLE 2

Method of Using DNP to Treat Viral Infections, HIV Disease

History: A 38 year old white male, past intravenous heroin addict, was diagnosed approximately 8 years ago with HIV by ELISA and positive Western blot for HIV p24 and gp41 antigens after presenting with weight loss and thrush. His history included repeated treatment for candidiasis, *pneumocystis carinii*, and various subcutaneous abscesses. Past medications included sulfamethoxazole, ketoconazole, fluconazole, zidovudine, didanosine and various other antibiotics. For the past year and a half he has been on highly active antiretroviral therapy (HAART) with various HIV protease inhibitors combined with thymidine, purine or cytosine nucleoside and nonnucleoside inhibitors. He was unable to tolerate nelfinavir because of diarrhea. Ritonavir caused intractable vomiting and abdominal pain. Current medications include indinavir, zidovudine and lamivudine. Review of the most recent viral load (VL) and CD4+ lymphocyte counts showed an initial drop in plasma HIV RNA (copies/ml) from 200,000 to 2,000 over a 12 week period with the VL rebounding back to 200,000 at week 16. CD4+ lymphocyte counts have remained between 100 to 200 cells/$mm^3$. Approximately 5 months ago he was treated for oral and endobronchial Kaposi's sarcoma (KS) with liposomal daunorubicin followed by liposomal doxorubicin. He denied treatment with vincristine or bleomycin. There is no history of recent diarrhea, recent weight loss, hemoptysis, shortness of breath on moderate exertion, or cardiac problems. There has been no illicit drug use over the past 2 years. The patient stated no combination of HAART has been able to lower his viral load and multiple side effects from the drugs are limiting his compliance to take the medications. There was no history of thermoregulatory problems.

Physical examination: weight=60 Kg; height=155 cm; BP=128/72; Resp=20; T=38.2° C.; and, the pulse was 92 & reg. Exam revealed asthenia and generalized enlargement of lymph nodes, some 2 to 3 cm in diameter in the axillary and inguinal regions. There was diffuse oropharyngeal thrush. Beneath the thrush, the oral cavity also contained several dark red plaque to nodular like lesions on the hard palate and gingiva. The lesions did not blanch on compression with the tongue blade. A crusted strawberry like mass, 1 by 2 cm, was present at the anus. There were no neurologic deficits or ocular lesions.

Laboratory studies: EKG, serum electrolytes, renal and liver function tests were normal. Hematocrit was 35.5%, WBC was 9,900 with 81% neutrophils, 4 bands, 11 lymphocytes and 4 monocytes. Platelets were 314,000/mm$^3$. Viral load was 400,000 copies/ml (Amplicor HIV Monitor test, Roche). A CD4$^+$ T cell count was quantified by flow cytometry at 250/mm$^3$. He was antibody positive for hepatitis C. Chest radiograph showed some bilateral apical patchy opacities. Pulmonary function tests showed all parameters, including forced expired volume, greater than 80% of predicted. Karnofsky score was greater than 70. Normal and tumor tissue biopsies, 3 to 6 mm in diameter, from the oral cavity and anus were obtained. The tissues were equally divided, weighed and placed in 4° C. Ringers lactate solution. Histologically confirmed normal and KS tissues were then subjected to microcalorimetric measurements in a thermal activity monitor (ThermoMetric, Jarfalla, Sweden). Recorded heat output (µW/min) was 8.2-8.5 times greater for the KS sarcoma lesions than nontumorous oral mucosa tissues. Repeat measurements with biopsies specimens in 30 uM DNP increased heat production in tumorous tissues 20.5 times more than nontumorous specimens.

Figure 16:
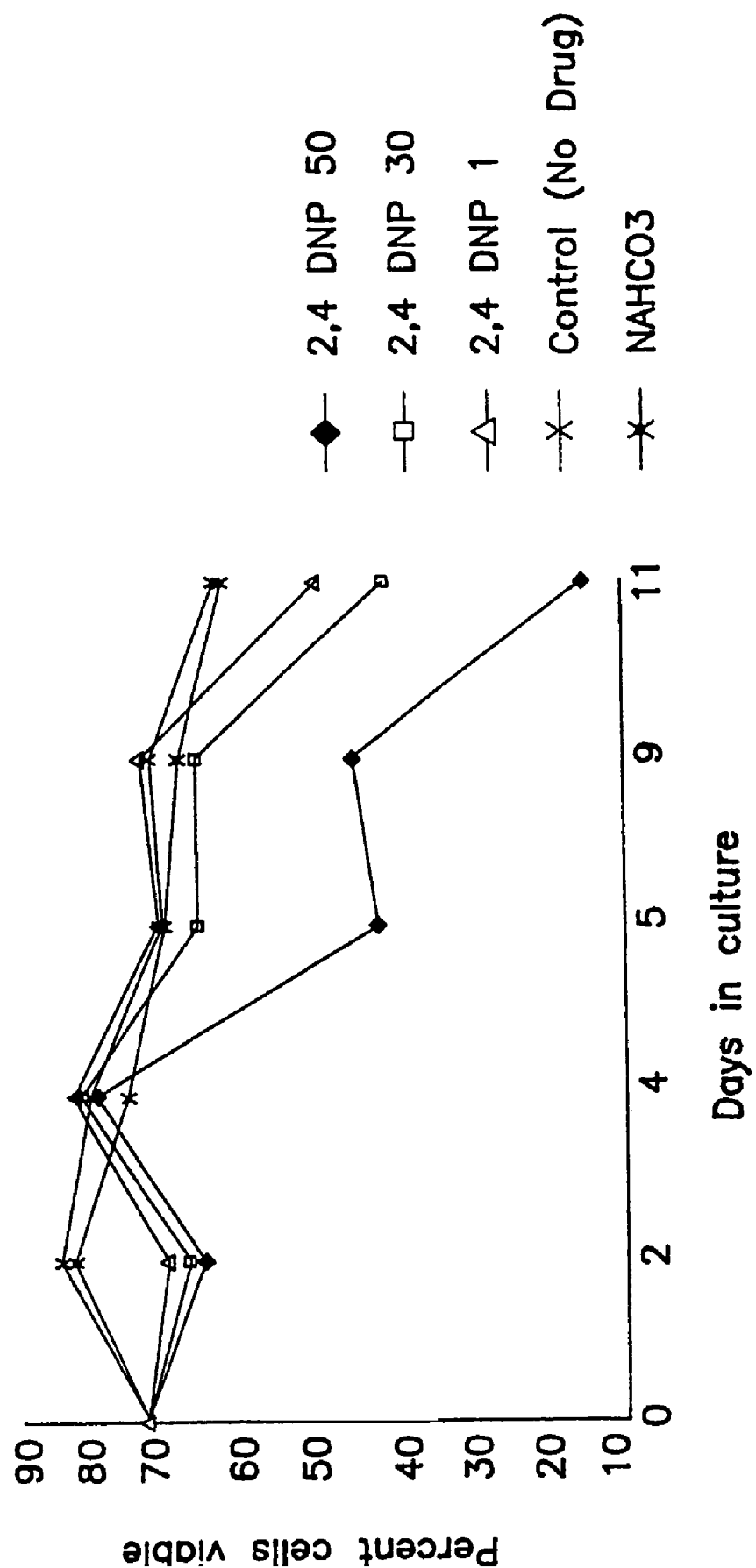
FIG. 16 shows killing of chronically HIV infected HUT-78 cells with varying concentrations of DNP.

Clinical assessment and treatment evaluation: HIV and HIV-infected T cells are known to be more sensitive to killing by heat than uninfected lymphocytes. Susceptibility to heat killing is enhanced with increased oxygen free radical production. Acute and chronically infected cells have decreased levels of manganous superoxide dismutase (MnSOD) activity. MnSOD is located exclusively in mitochondria. Mathematical modeling of human HIV production and CD4+ T cell turnover predicts that reducing both free virus and actively infected cells by a minimum of 40% with 1 hour of 42° C. therapeutic hyperthermia every third day will promote recovery of the uninfected T-cell population. Human HIV studies with extracorporeal hyperthermia of 41-42° C. have reported isolated cases of extended patient survival, elimination of detectable virus, and improvement of Kaposi's sarcoma lesions. DNP is known to generate intracellular hyperthermia and oxygen free radicals from the level of the inner mitochondrial membrane. Studies on in vitro inactivation of chronically HIV infected HUT-78 cells by various concentrations of DNP are graphically represented in FIG. 16.

The patient has been and remains resistant to treatment with HAART. Opportunistic infections with candida and Kaposi's sarcoma herpes virus (KSHV, human herpesvirus type 8) causing his thrush and Kaposi's sarcoma are comorbid conditions indicative of a worsening prognosis. In spite of having AIDS with candidiasis and Kaposi's sarcoma, the patient maintains good cardiac and pulmonary function. There was no history of thermoregulatory problems. It was discussed and agreed that hyperthermia treatments with core body temperatures of 41° C. would be administered on a daily or every other day basis, as tolerated, for a minimum of 3 hours, not to exceed 5 hours.

Pretreatment protocol: all medications were stopped 2 weeks prior to treatment. The patient refused taking diazepam, placement of a Foley catheter and oxygen face mask. He dressed himself into a dry cold water immersion suit (Stearns, ISS-590I, Universal Adult) designed to prevent heat loss and modified for easy placement of physiologic monitors. Equipment for measurement of heart rate, temperature, carbon dioxide production and Kcal of heat produced were conducted as outlined in Example 1. An oral breathing tube was used to measure VO$_2$ from room air. Urine output was measured when the patient voluntarily urinated through a "Texas" catheter (superficial condom tightly fitted around the head of the penis with tubing connected to urine collection bag). The patient was informed that hyperthermia would be administered as tolerated by his stamina and monitored clinical parameters, not to exceed 5 hours, on a daily or every other day basis, for a total of 5 sessions.

Treatment procedure: Baseline reading for 5 minutes established an average VO$_2$ of 300 cc/min. An initial dose of 2 mg/kg of DNP was administered over a 2 minute period. VO$_2$ increased and stabilized at 15 minutes at 340-380 cc/min. An additional 2 mg/kg DNP infusion was given, the VO$_2$ increased and stabilized at 610-630 cc/min. Body core temperature increased to 39.4° C. within 60 minutes. A gradual fall in blood pressure was noted at 90 minutes to 100/60 mm/Hg. Norepinephrine bitartrate (Levophed) was given IV drip at a dose of 1 microgram/min. and adjusted to maintain blood pressure at 130/80. Approximately 1 minute after initiating the vasopressor, heart rate increased from 90 to 100 and VO$_2$ to 0.85 liters/min. Core body temperature increased within 20 minutes to 41.5° C. VO$_2$ was maintained at 1.0 liters/min. by lowering or increasing the dose of norepinephrine. An additional infusion of 1 mg/kg DNP was given at hour 4 to correct a dropping VO$_2$. On occasions when the core temperature increased above 41.6° C., a lower extremity was exposed for evaporative heat loss. The patient withstood the procedure without any untoward effects for a period of 7 hours. The protocol was repeated consecutively for 5 days without the additional use of vasopressors.

Treatment outcome: Immediately after the first treatment oral candidiasis improved by 50%. The oral and anal Kaposi's lesions exhibited marked erythema with circumferential areas of blanching. On the second day of treatment the KS erythema diminished. There was no evidence of oral candidiasis on the 3$^{rd}$ day of therapy. The anal tumor was crusted and approximately 60% diminished in size on the 5$^{th}$ and last day of therapy. Lymphadenopathy progressively decreased and was resolved at 2 weeks post-treatment. At 30 days post-treatment, there was complete regression of both oral and anal KS lesions. Repeat blood work on days of treatment showed no significant hematologic, electrolyte, liver or kidney changes from baseline. Viral load immediately after treatment day 5 showed 50,000 HIV-RNA copies/ml. HIV RNA was non-detectable at 4, 6 and 12 weeks post-treatment. CD4+ T cell lymphocyte counts increased to 380-420 cells/mm$^3$ by week 4 and remained stable at week 6 and 12. FIG. 17 shows monitored patient parameters on treatment day 1. FIG. 17a) shows changes in surrogate markers immediately after treatment, weeks 4, 6 and 12.

EXAMPLE 3

Use of DNP to Treat Bacterial Infections, Lyme Disease

History: A 33 year old white female with a textbook case of Lyme borreliosis related being bitten by a tick and developing a pathognomonic erythema migrans on her right anterior thigh. The rash resolved within two weeks but 3 months later she developed verbal memory impairment, migratory arthritis of the knees, ankles and tibias. Fibromyalgias, tachycardias and a left sided Bell's palsy ensued. Constitutional symptoms of fatigue, malaise and severe depression caused her to undergo psychiatric care for 1½ years before she was definitively diagnosed with chronic *Borrelia burgdorferi* infection. She was treated with ceftriaxone, 2 g intravenously every 12 hours for 14 days. Four months after apparent improvement she developed photophobia, headaches, pronounced memory loss, depression, dysesthesias and a painful, swollen left knee joint. Repeat ELISA, Western blot and DNA-PCR were all positive for *B. burgdorferi*. Spinal tap showed pleocytosis with positive antibody and PCR tests for neuroborreliosis.

Over the next year the patient received prolonged ceftriaxone, 2 g per day intravenously for 3 months, and 3 individual short courses of oral ciprofloxacin, minocycline, and azithromycin. Symptoms failed to resolve. Two months after her last regimen of antibiotics a new annular erythematosus eruption, suggestive of erythema migrans, reoccurred on the right thigh and developed under her left axilla. Doxycycline was instituted and the rash subsided. The patient refused further antibiotic therapy because of associated intractable diarrhea and has made tentative plans to undergo "malariotherapy" in China.

Physical examination: weight=60 Kg; height=160 cm; BP=130/70; HR=86 & reg; resp=18; T=37.3° C. Physical exam revealed a swollen and tender left knee. A thin, atrophic hypopigmented area of skin over the right thigh, typical of acrodermatitis chronica atrophicans was present. Neurologic exam showed some verbal memory deficit. There were bilateral, lower distal extremity paresthesias.

Laboratory studies: EKG demonstrated a first-degree atrioventricular block (PR internal>0.2 sec), some widening of the QRS complex and Wenckebach periodicity. There were no dropped beats. Left knee arthroscopy showed synovial hypertrophy with early erosive arthritis. Synovial fluid analysis revealed a WBC of 50,000 cells/ml with 70% neutrophils and a positive DNA-PCR for *Borrelia burgdorferi*. Biopsy sections of synovial tissue showed chronic nonspecific synovitis. Warthin-Starry and silver staining histology revealed spirochetal organisms consistent with *Borrelia burgdorferi*. Lumbar puncture spinal fluid analysis showed pleocytosis, elevated gamma globulin and positive PCR for *B. burgdorferi*. Spinal fluid cultured for 2 months in Barbour-Stoenner-Kelly medium was reported positive for *B. burgdorferi*. Serum electrolytes, kidney, liver function and hematologic studies were all within normal limits. The patient underwent a stress EKG, attaining a maximum heart rate of 165 with no evidence of arrhythmia or S-T segment depression.

Clinical assessment and treatment evaluation: Lyme disease is a zoonosis caused by a slow growing pathogenic spirochete, *Borrelia burgdorferi*. In various mammalian species, including man, these organisms are known to invade heart, kidneys bladder, spleen and brain. *Borrelia* spirochetes are very resistant to treatment with antibiotics, especially if there is evidence of central nervous system or joint involvement. Viable *B. burgdorferi* have been isolated from antibiotic treated monolayers of fibroblasts. *Borrelia* spirochetes are known to be facultative intracellular pathogens in fibroblasts by laser scanning confocal microscopy. Central nervous system tissue, joints, front chamber of the eye and intracellular location can provide the Lyme spirochete with a protective environment against antibiotic therapy and *Borrelia burgdorferi* have been reliably cultured from patients with chronic disease, even from those previously aggressively treated. This patient has confirmed chronic CNS and joint Lyme disease in spite of extensive antibiotic therapy.

The Lyme spirochete is irreversibly inactivated by heating at 40° C. for 3 hours, 41° C. for 2 hours or 41.5° C. for 1 hour. Susceptibility of all strains of *Borrelia burgdorferi* to penicillin and ceftriaxone is increased up to 16-fold by elevation of temperature from 36° C. to 38° C. At 40° C. *Borrelia burgdorferi* increases expression of at least 12 heat shock proteins (HSP), most of which are strongly immunogenic. The patient had no history of thermoregulatory problems. She was informed that her body temperature would be raised between 4° to 41° C. for a period of 3 hours, the actual level and time under hyperthermia would depend on her monitored clinical parameters.

Pretreatment protocol: the evening prior treatment the patient was instructed not to eat and dress in cotton undergarments. Approximately 4 hours prior to treatment 2 mg alprazolam was administered by mouth. The patient dressed herself into a dry cold water immersion suit (Stearns, previously described) with headgear. Monitoring sensors, including EKG display, IV fluids and Foley catheter were attached and the suit was zipped closed. The patient opted for oxygen supplementation. The modified face mask was connected to the TEEM 100 metabolic Analysis System for $VO_2$ measurements. Data was recorded as previously described.

Treatment procedure: baseline recordings of 10 minutes showed a $VO_2$ of 220 cc/min., 3.7 cc $O_2$/kg/min. The patient was infused with 1 mg/kg DNP over a 2 minute period. $VO_2$ increased and stabilized at 250 cc/min, 5.3 cc/kg/min. A second dose of 2.0 mg/kg was infused over a 2 minute period and the $VO_2$ peaked at 400 cc/min, 8.8 cc $O_2$/kg/min. An additional dose of 1.0 mg/kg DNP was given 30 minutes after the second dose. The $VO_2$ increased and reached a stable plateau at 600 cc/min, 10.8 cc/kg/min. Rectal temperature continued to climb until a range of 40.2 to 40.6° C. was reached at 70 minutes after the initial dose. A fall in $VO_2$ was noted at 90 minutes, a dopamine drip at 2-3 mcg/kg/min was initiated. $VO_2$ increased back to 680-710 cc/min. The temperature remained stable between 40.1° C. and 40.6° C. throughout the 3 hour plateau treatment period. The patient periodically requested the $VO_2$ monitoring mask be removed during the hyperthermia treatment period. She was accommodated with removal of the mask on two occasions for periods not exceeding 10 minutes. The patient experienced no problems during the procedure but was noticeably fatigued by hour 3. The treatment was terminated 4 hours and 10 minutes after the initial dose of DNP. Twenty five minutes after the patient was removed from the neoprene survival suit, the rectal core temperature dropped to 38.5° C. Normothermia was achieved approximately 60 minutes after cessation of therapy and removal from the survival suit. Approximately 6.5 to 7 hours after treatment the patient experienced chills, an increase in oral temperature to 38.7 degrees centigrade and malaise. IV fluids and the dopamine drip at 2 mcg/kg/min were restarted and the patient was closely observed. Her symptoms subsided over 3 hours and by the next day she felt active and hungry. It was surmised she may have experienced a delayed Jarisch-Herxheimer reaction. The patients monitored treatment flow chart is FIG. 18.

Treatment outcome: at two months follow-up the patient stated her arthralgias, myalgias, malaise, fatigue and memory deficits have disappeared. Lower extremity dysesthesias were no longer present. EKG showed resolution of her first degree A-V block. The patient was informed of her past positive cerebrospinal fluid positive culture for the Lyme disease spirochete. It was suggested a repeat spinal tap be performed for *B. burgdorferi* by PCR and culture. If positive, the patient agreed she would be re-treated with both DNP induced hyperthermia and intravenous ceftriaxone for maximum synergism. Repeat spinal fluid analysis was normal, i.e., no elevated protein, no detectable *Borrelia* DNA by PCR and no pleocytosis. Three months later, spinal fluid culture on Barbour-Stoenner-Kelly II medium was reported negative.

EXAMPLE 4

Method of Using DNP with Vasopressors and Chemotherapy to Treat Neoplasia, Peritoneal Carcinomatosis History: A 55 year old female presented with a distended abdomen due to ascites. Laparotomy revealed peritoneal dissemination of a malignancy with histological findings of an undifferentiated adenocarcinoma, origin unknown.

Physical examination: weight=55 kg; height=154 cm; BP=140/90; HR=88 & reg; Resp=22; T=37.6° C. The patient was a well developed and well nourished Muslim female with a healing midline laparotomy scar. Ballotable ascites was detected in the abdomen. There was no lymphadenopathy.

Laboratory studies: laboratory examination of the ascitic fluid showed high levels of amylase. She had a hemoglobin of 9.2. High levels of amylase and tumor markers, including CA15-3, CA 125 and CA72-4 were present in the serum. Blood chemistry, liver and kidney function tests were within normal limits. Chest X-ray and EKG was normal. MRI and ultrasound of the abdomen showed normal pancreas, liver and atrophic ovaries, there were widespread nodular lesions consistent with peritoneal carcinomatosis.

Clinical assessment and treatment evaluation: the patient had an inoperable malignancy of unknown origin. Chemotherapy in such cases is only of marginal survival benefit. Hyperthermia, combined with chemotherapy has been shown to be synergistic with increased tumor response and survival benefit. Tumor antigen markers are known to be increased by the heat shock response and may further enhance immunologic surveillance. The patient had no history of thermoregulatory problems but refused to be placed in wet suit or survival suit because of a "phobia of enclosed tight garments".

It was elected to treat the patient with hyperthermochemotherapy. Treatment consisted of DNP, and combination chemotherapy with carboplatin, mitomycin, and doxifluridine. An α-1 adrenergic receptor agonist was used to minimize peripheral vascular dilation and heat loss.

Pretreatment protocol: the patient was transfused with three units of packed red blood cells. A Foley catheter was inserted on each day of treatment. She was covered in a water soaked blanket containing a polyethylene lining. A shower cap with towels was used to prevent heat loss from the head. Intravenous lines were placed into both arms with 19 gauge intracaths. EKG, heart rate, rectal thermistor, and $VO_2$ monitors were attached. Oxygen supplemented facemask and equipment was attached and data monitored as previously described under Example 1.

Treatment protocol: the patient was given chemotherapy by mouth. The total doses of carboplatin, and mitomycin were 450 mg and 24 mg IV respectively on day 1 and last day of week 6. Doxifluridine, 600 mg, was orally administered every day for 5 days and repeated the last 5 days of week 6. On the day of DNP infusion, baseline recordings were established for 10 minutes. Mephenteramine sulfate, 30 mg, was given by intramuscular injection. Ten minutes later her heart rate increased to 96 and her $VO_2$ increased from 250 to 320 cc/min. $VO_2$, heart rate and blood pressure stabilized after 20 minutes and she was given an initial dose of 1 mg/kg DNP. Additional 0.5 mg/kg infusions of DNP were administered in 3 successive infusions spaced 20 minutes apart. The patients $VO_2$ stabilized between 780-820 cc/min. and her core temperature increased to a maximum of 41.4° C. After a plateau temperature of 41.5° C.∓0.5° C. was reached, her level of $VO_2$ and temperature was maintained for a period of 2 hours and 30 minutes with an additional infusion of 0.5 mg/kg DNP given 50 minutes after the last dose. The DNP treatment protocol was repeated every fourth day for a period of 6 weeks. A representative monitored flow chart is shown in FIG. 19.

Treatment outcome: By the combined treatments outlined above, ascites resolved by the end of the sixth week. Serum levels of amylase and all tumor markers decreased after the third week of treatment and were normal at week 6. Repeat magnetic resonance imaging and echo re-examination of the abdomen showed complete resolution of peritoneal metastasis. Nine and a half months after treatment, the patient is alive without any evidence of tumor reoccurrence.

EXAMPLE 5

Use of DNP with Thermosensitive Liposomes

To overcome the toxicity to normal tissues of many anti-cancer agents such as doxorubicin and anti-infectious drugs such as amphotericin B, liposomal formulations have been developed. Liposomal doxorubicin is known to have reduced cardiotoxicity and increased antineoplastic efficacy. Thermosensitive liposomes can further enhance tumor targeting and decrease toxicity by release of their water soluble drug contents in response to tumor hyperthermia. Various synthetic and natural lipids such as dipalmitoyl phosphatidyl choline and distearoyl phosphatidyl choline or egg phosphatidyl choline and cholesterol can be combined in different molar ratios with ethanol, or other agents that have a biphasic effect on gel-to-liquid phase transition of phosphatidyl choline bilayers, to produce liposomes that melt (undergo gel-to-liquid crystalline phase transitions) at a predetermined hyperthermic temperature.

Thermosensitive liposomes were prepared form phosphatidyl choline (PC) and cholesterol (Ch) using the ethanol method of Tamura et al. A combination of PC:Ch in a 8:1 molar ratio in the presence of 6% (v/v) ethanol resulted in formation of liposomes having a transition temperature between 40.2 and 40.8° C. The anticancer drug dacarbazine [5-(3,3'-dimethyl-1-triazino) imidazole-4-carboxamide] was encapsulated in these heat-sensitive liposomes at a concentration of 3 mg/ml. The in vivo efficacy of the thermosensitive, liposome encapsulated dacarbazine was tested on Swiss albino mice transplanted with a dimethyl benzo-dithionaphthene derived ascites fibrosarcoma subjected to DNP induced hyperthermia.

Male, 10-12-week-old, Swiss albino mice were injected with $3\times10^6$ viable fibrosarcoma cells into the peritoneum. After 15 days the animals were divided into various treatment and control groups receiving intraperitoneal injections of free dacarbazine, DNP alone, DNP+empty liposomes and DNP+liposome encapsulated dacarbazine. DNP induced hyperthermia was recorded with neonatal rectal and 22 ga. hypodermic YSI probes. Temperatures were recorded 30 minutes after a 20 mg/kg intraperitoneal dose of DNP. DNP was administered every day for a total of 5 doses. In all cases the hypodermic, intraperitoneal temperatures were 1° C. higher than the rectal.

Figure 20:
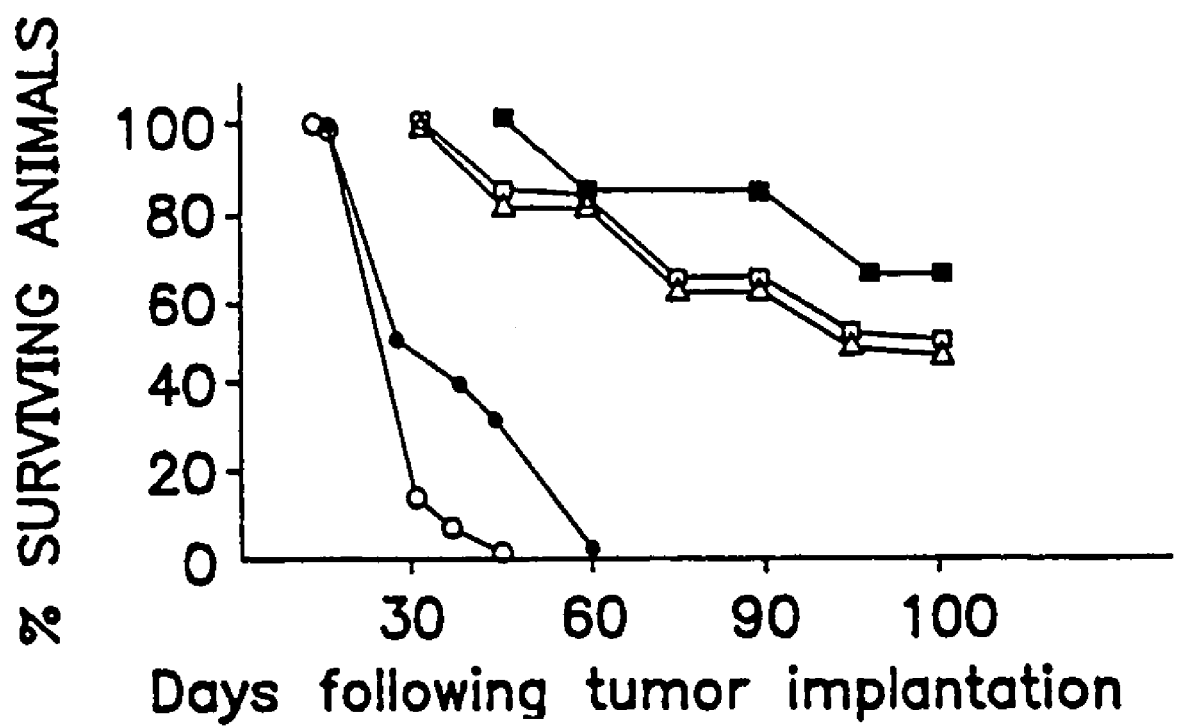
FIG. 20 shows survival studies of tumor growth-regressed animals treated with DNP and a thermosensitive liposome encapsulated drug.

As shown in FIG. 20, survival curves of animals treated with DNP alone and DNP+drug containing liposomes were significantly improved in comparison to controls. DNP-hyperthermia treated animals remained alive at day 100 whereas sham treated animals all died by 60.

EXAMPLE 6

Use of DNP to Induce Autologous Heat Shock Proteins as a Form of Thermal Preconditioning Prior to Arterial Balloon Catheterization or Ischemic Surgical Injury DNP would be given orally at doses to increase the $VO_2$ from 1.5 to 5 times above normal per day for a period of 2-6 days or, as an infusion at doses that would increase $VO_2$ and core body temperatures no greater than 39° C. for periods of 5 to 6 hours or, intravenous doses of DNP alone, with vasopressors, or other short acting metabolic stimulators, that would increase $VO2$ to equivalent core temperatures of 40-41° C. for periods of 15-30 minutes. Within 8-48 hours after cessation of DNP, the patient would have maximum heat shock protein production. Such DNP induced stress would improve clinical outcome by induction of cellular heat shock protein synthesis with protection of the patient's, organs, tissues and cells from subsequent ischemic surgical or traumatic procedures.

Figure 23:
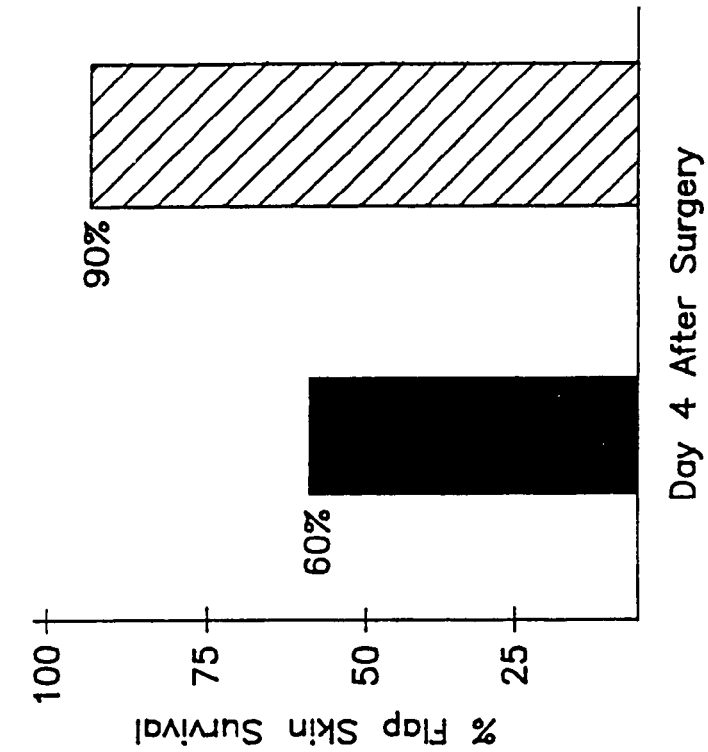
FIG. 23 shows the improved effect of musculocutaneous flap skin survival after DNP pretreatment.
Figure 22:
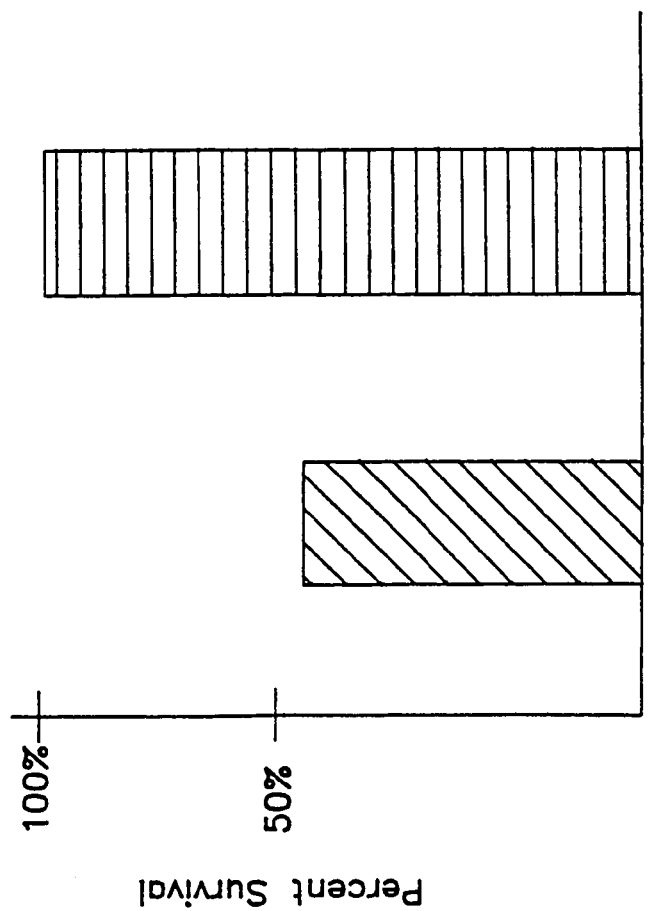
FIG. 22 shows the protective effects of DNP pretreatment on survival after prolonged hepatic eschemic induced by Pringle's maneuver.

This method of DNP induced preconditioning could be used to decrease intimal thickening and restenosis after angioplasty, improve ischemia/reperfusion injury in organ and tissue transplantation, and improve surgical outcome of procedures that require temporary or prolonged occlusion of arterial blood flow. Examples of such DNP induced autologous thermotolerance used as a form of preconditioning are depicted in FIG. 21, which shows limitation of proliferative arterial catheter balloon injury in Sprague-Dawley rats pretreated with DNP induced hyperthermia; FIG. 22 shows the protective effect of DNP pretreatment before hepatic ischemic injury cased by Pringle's maneuver; and, FIG. 23 depicts improved musculocutaneous flap skin survival after induction of heat shock proteins by DNP.

EXAMPLE 7

Method of Using DNP to Enhance Proton Emission Tomography (Pet) in the Diagnosis of Malignancy and/or Malignant Transformation (Glioma)

History: A 24 year old white male with neurofibromatosis presented with a six month history of left sided loss of body sensation, emotional changes, sensory seizures, inattention to conversations and sensations of jamais vu.

Physical examination: weight=65 kg; height=175 cm; BP=135/80; HR=86 & reg; Resp=18; T=37.9° C. The patient was a well developed well nourished white male with left upper and lower extremity sensory loss, postural instability and loss of tactile discrimination. There was a frank left handed astereognosis. Eye examination was normal, without papilledema.

Laboratory studies: Complete hemogram, blood chemistry and endocrine examination were normal. EEG was within normal limits. MRI with gadolinium enhancement showed a decreased signal in the right temporoparietal region with no evidence of contrast enhancement. PET examination with [$^{18}$F]fluoro-2-deoxy-D-glucose (FDG) revealed a homogeneous hypometabolic area (metabolic Grade 1) consistent with a Low grade glioma in the right temporoparietal region. There were no zones of high FDG uptake. Differentiation of displaced noninvaded gray matter from the tumor was not discernible on PET imaging.

Clinical assessment and diagnostic evaluation: although Low grade gliomas generally present histological features of benign tumor, it is known that the presence of zones of high FDG uptake by PET scan in such gliomas is associated with a higher percentage of malignant transformation. PET-FDG with evidence of tumor hypermetabolism is believed to be an early biochemical marker of cellular malignant transformation and is of prognostic value in High grade gliomas. Biochemically, high glucose (uptake of FDG) utilization in the presence of oxygen, known as aerobic glycolysis, is believed to be the result of a hyperactive hexokinase attached to tumor mitochondria. Increased FDG uptake therefore, represents increased hexokinase activity and is associated with increased aggressiveness in gliomas, meningiomas and other neoplasms. Since DNP uncouples oxidative phosphorylation, any shortfall in mitochondrial ATP production must come from increased glycolysis. As a result, FDG uptake will be proportionately increased in DNP treated malignant cells over those that are normal in contralateral brain white and gray matter. Since no abnormal FDG uptake was detected in the tumor by standard PET methodology and the PET scan was unable to clearly delineate the borders of the tumor, it was elected to give the patient a low dose of DNP to enhance FDG uptake and repeat the PET scan. Hypermetabolic components of the tumor would thus permit a more focused PET-guided stereotactic biopsy.

Pretreatment protocol: three days prior to DNP dosing and repeat PET-FDG scan, the patient's dosage of phenyloin was increased from 100-mg three times daily to 200-mg three times a day. The same positron emission tomogram, a CTI-Siemens 933/08-12 which provides a 6.75-mm adjacent slices and in-plane spatial resolution (full-width at half maximum) of ~5 mm, was to be used. The highest level of non to DNP stimulated FDG uptake in the tumor area was to be compared and qualitatively graded by two radiologists. Independently, each investigator was to visually evaluate the positron emission tomogram and use the following metabolic grading scale: I, FDG uptake less than contralateral white matter; II, uptake between the levels in contralateral white and gray matter; III, FDG uptake equal to or greater than in contralateral gray matter.

Diagnostic—treatment protocol: the patient was given a 300 mg capsule of DNP (approximately 4 mg/kg body weight) three hours prior to undergoing a PET-FDG scan. Forty minutes prior to the emission scan he was intravenously injected with a bolus of FDG according to standard methodology. Immediately prior to the 20-minute emission scan the patients VO$_2$ uptake was 40% above that at baseline. The patients DNP/VO$_2$ flow chart is FIG. 24.

Diagnostic outcome: DNP enhanced PET-FDG scan revealed two areas of hypermetabolism. One of the areas surpassed the limits of the lesion on CT images and consequently only one of the targets (graded as a III on FDG uptake) was selected in the "abnormal PET-normal CT" area.

The plane that best displayed the abnormal FDG hypermetabolic uptake area was selected and a pixel located in the center of the zone was interactively pointed at on visual inspection. The coordinates of that DNP induced hypermetabolic pixel were then calculated and set as a target for biopsy. A PET-guided stereotactic biopsy was performed under the procedure described by Levivier et al., i.e., the target from the PET image was projected onto the corresponding stereotactic computed tomographic (CT) slice to control the reliability and precision of target selection and the trajectory. Serial stereotactic biopsies were performed along the trajectory by the method described by Kelly et al.

On pathologic examination, including analysis of nuclear polymorphism and cell density, 2 foci of anaplasia consistent with glioblastoma (Grade III astrocytoma) were noted.

Treatment outcome: based on the DNP enhanced PET-FDG scan diagnostics outline above, this patient was found to have a malignant transformation in his otherwise Low grade glioma. This diagnostic treatment protocol procedure of detecting foci of hypermetabolism caused him to undergo systematic radiation therapy with chemotherapy (dibromodulcitol-procarbazine-carmustine) early in the course of his malignant process. One year after diagnosis and therapy the patient again underwent PET scanning. DNP enhancement (repeated as outlined under "Diagnostic" above) revealed a single hypermetabolic component (metabolic Grade II) in the tumor area. Repeat PET-guided biopsy revealed the area to be a zone of radionecrosis. The remaining viable tumor, even with DNP enhancement, continued to be a metabolic Grade I. The patient remains alive one and a half years after his diagnosis, albeit with left-sided hemiparesis.

EXAMPLE 8

Method of Using DNP to Enhance Detection of Malignant Tumors by High Resolution Digital Infrared Imaging (Breast Carcinoma)

History: a 34 year old white female with existing fibrocystic disease of the breast underwent yearly mammography and was found to have an equivocal opacity in the right breast, medial to the aereola. Two past breast biopsies were negative for malignancy and consistent with fibroadenomatous disease of the breast. The patient was opposed to another breast biopsy (would be third), unless there was a definitive indication of a lesion over that of her known fibrocystic disease of the breasts.

Physical examination: WT=60 kg; HT=164 cm; BP=120/72; HR=88 & reg; R=18/min; T=37.7 C. The patient was a normal appearing white female with scattered to diffuse nodularities in both breasts. A palpable 3×2 cm, non-tender, lump was located 3 cm medial to the right aereola.

There was absence of nipple discharge, retraction, skin dimpling, rash or discoloration of either breast. There were no palpable axillary lymphadenopathy.

Laboratory studies: chest x-ray, EKG, blood chemistry, and hemogram examination was normal. Mammography, Doppler ultrasound, MRI, and scintinammography failed to indicate or eliminate a possible occult carcinoma in this young patient with dense, fibroadenomatous breast disease. A diffuse, non-cystic, opacity on the right breast was the only definitive finding from these breast studies.

Clinical assessment and diagnostic evaluation: this patient has had two previous open breast biopsies without evidence of malignancy. Early detection of breast carcinoma is of crucial importance to survival. False negative results of mammography (and other complimentary studies) range between 5-30%. The ability of infrared imaging technology to detect changes related to increased metabolism (tumor) and angiogenesis has greatly improved from that of 30 years ago. High resolution digital computerized infrared equipment can now detect focal increases in tumor temperature from as little as 0.05° C., and increases in focal breast temperatures may be as high as 1-2° C. in malignant tumors versus normal, contralateral breast sites.

Since it is known that infrared imaging has at least a 19% rate of false positives and 17% of false negatives, and equivocal mammography and abnormal infrared imaging is not uncommon in young women with dense breast tissue and diffuse fibrocystic disease, the use of DNP to enhance tumor metabolism (infrared imaging) over that of normal tissue, could be of substantial diagnostic benefit. Specifically, DNP would greatly enhance tumor metabolism (infrared imaging), in comparison to non-DNP enhanced infrared imaging and would greatly increase tumor detection when there is either insufficient production or detection of metabolic heat or vascular changes. Further, the heat differential between DNP enhanced and non-DNP infrared tumor imaging may also decrease the false positive rate seen with this procedure, especially in benign conditions such as fibrocystic disease of the breast. Since non-DNP infrared imaging is capable of detecting as great as 1-3° C. changes in focal temperature between normal and malignant tissue, DNP enhancement would increase the temperature difference several fold and enhance both the sensitivity and precision of currently available infrared imaging technology. The patient agreed to have both of her breasts examined non-invasively with infrared imaging, before and after intravenous DNP administration to ascertain if there was increased infrared signaling from the worrisome, palpable lump in her right breast.

Prediagnostic protocol: the patient was disrobed to the waist and sat with her hands interlocked over her head for a five minute equilibration period in a draft free, thermally controlled room—kept between 18° C. and 20° C. She did not take any oral medication, alcohol, coffee, and did not smoke, exercise or use deodorant three hours prior to testing. A baseline of 4 images consisting of an anterior, undersurface and 2 lateral views of each breast were generated by an integrated infrared imaging station consisting of a scanning mirror optical system containing a mercury-cadmium-telluride detector (Bales Scientific, CA). The infrared system had a spatial resolution of 600 optical lines, a central computerized software processor providing multi-tasking capabilities and a high-resolution color monitor capable of displaying 1024×768 resolution points with 110 colors or shades of gray per image. Images were stored on retrievable laser discs.

Diagnostic treatment protocol: after the above baseline studies were performed, the patient was given an initial intravenous dose of 1 mg/kg DNP and observed for a period of 20 minutes. An additional 2 mg/kg of DNP was then administered and 30 minutes thereafter, she was taken to the thermally controlled room for repeat DNP-enhanced infrared imaging. Immediately prior to transferring the patient to the thermally controlled room, the patients $VO_2$ was incrementally increased to 50% above her $VO_2$ baseline, see FIG. 25. Repeat infrared images were then obtained under the exact protocol used for obtaining baseline studies.

Diagnostic—treatment outcome: baseline (non-DNP enhanced) infrared imaging revealed insignificant vascular asymmetry and no significant temperature changes when the results were reviewed and compared to the rest of the ipsilateral or contralateral breast sites.

DNP enhanced infrared imaging resulted in a bilateral global breast temperature increase of approximately 0.5° C. An abnormal, 2.5° C. increase in temperature was noted in the palpable, right breast lesion discovered by clinical exam. Since no non-cancer causes for such a dramatic temperature increase could be identified, i.e. abcess, trauma, or recent surgery, this 5 fold increase in heat production (above the DNP baseline increase of 0.5° C.) was highly suspect to be caused by an early malignancy.

The patient was admitted to the hospital and under general anesthesia underwent an open breast biopsy. Frozen section (and later permanent tissue mounts) revealed a well-differentiated intraductal carcinoma. Progesterone and estrogen receptors, as determined by immunocytochemical methods, were negative. A simple, right mastectomy with axillary lymph node dissection was performed. A total of twelve lymph nodes were identified: there was no evidence of tumor. The patient refused chemotherapy and radiotherapy. She was placed on long-term oral tamoxifen (10 mg twice a day).

EXAMPLE 9

The Use of Dinitrophenol with Artificial Electron Receptors (or Other Free Radical Forming Agents) in the Treatment of Hormone and Chemotherapy Resistant Malignancy (Prostate Cancer)

History: a 68 year old Mexican male, developed a gradual increase in low back pain, right hip pain and several episodes of hematuria over a 10 month period. He was referred to a urologist and diagnostic work-up revealed a carcinoma of the prostate with the extension of the tumor into the bladder. Bony metastasis were present to the right pelvis, fourth and fifth lumbar vertebra, right femur, left humerus, right sixth and seventh ribs and right scapula. He refused any form of surgery but underwent radiation therapy to the pelvis and symptomatic bony lesions. Treatment was initiated with megestrol acetate (640 mg/day), prednisone (20 mg/day) and leuprolide (7.5 mg/month). After three months of therapy the patient continued to have progression of his disease manifested by increasing bone pain, rising prostatic specific antigen levels (PSA) and increasing serum acid phosphatase.

Physical examination: WT=72 kg; HT=175 cm; BP=140/86; R=22; T=37.6 C; HR=88 & reg; Exam revealed mild emaciation with some scrotal and +1 pitting bilateral lower extremity edema. There were scattered bilateral, basilar rales on examination of the chest.

Laboratory studies: EKG demonstrated a right partial bundle branch block. Chest x-ray showed mild chronic obstructive pulmonary disease with minimal fibrosis. There was some patchy, interstitial edema in both lower lung fields. There were no pulmonary metastasis. Complete blood count showed a mild anemia with a hemoglobin of 10.5 and a hematocrit of 34%. Liver function tests were normal. White blood cell count, differential and platelet count, was within normal limits. PSA level was 58 ng/ml. Serum acid phosphatase was 2× above normal. Blood electrolytes including calcium were within normal limits. The acid phosphatase, AST, ALT and bilirubin levels were normal. Radionucleotide bone scan revealed multiple metastasis in the axial skeleton and ribs. Review of past prostatic biopsy slides showed a high grade adenocarcinoma of the prostate with a Gleason Grade of 8. Pulmonary function studies showed moderate airflow obstruction with mild hypoxemia and hypercarbia. Stress EKG was not performed because of his severe exercise intolerance.

Clinical assessment and treatment evaluation: the patient has a metastatic, hormone-refractory prostate carcinoma with clinical progression documented by increasing bone pain and rising serial PSA values. Under the TNM classification of the American Joint Cancer Committee for prostate cancer (T=degree of primary tumor extension; N=regional lymph node involvement; and, M=presence of distant metastasis), he has the highest stage (T4 N3 M1). Histologically, the tumor is aggressive by the Gleason Grading System. Since death due to prostatic carcinoma is almost invariably a result of failure to control metastatic disease, and since prostatic cancers are well-known to be sensitive to heat stress, the present DNP therapy was undertaken as a last resort effort to stop tumor progression and/or improve the patients quality of life.

In view of the patients age, pulmonary problems and poor performance status (Karnofsky Score of 6) it was decided to treat the patient with moderate doses of DNP and a free radical cycling agent, methylene blue (MB), to induce synergistic tumor killing. The effect of methylene blue on cellular reduction-oxidation status (redox) is well known. Methylene blue readily traverses cell membranes and acts as an electron acceptor from the major coenzymes. Unlike other oxidizing drugs, it cycles futilely, transferring electrons from endogenous substrates to oxygen. Depending on the redox status of a cell, MB can act as either an intracellular electron acceptor or donor. MB directly catalyzes the reaction of intracellular reductants, NADPH, NADH and GSH (reduced glutathione) with oxygen causing the production of hydrogen peroxide, superoxide anions, and the formation of the potent cytotoxic oxidant species, peroxynitrite. In DNP partially uncoupled mitochondria, MB further stimulates respiration due to its dual action of providing reducing equivalents necessary for beta-oxidation of fats and electron donating/shuttling capacity, with respect to the mitochondrial respiratory chain. It is an effective drug, at doses of 1-3 mg/kg, in treating nitrate-induced methemoglobinemia. MB is also used as an antidote given as a 100 mg IV bolus for encephalopathy associated with alkylating chemotherapy.

Since uncoupling, heat and MB increase the flux of cellular free radicals and malignant cells possess a high bioreductive capacity, the synergistic effects of DNP with MB would allow for maximum tumor killing with minimum to moderate levels of induced total body hyperthermia. Additional free radical cycling agents that can be used in lieu of MB include, but are not limited to: phenazine methosulfate, xenobiotics such as quinones (e.g., menadione, semiquinone, naphthoquinone, duroquinone, indigo carmine), nitrocompounds (e.g., metronidazole, niridazole, nitrofurazone, flunitrazepam), eminium ions (e.g., methyl viologen, benzyl viologen, etc.), and others. In this patient, DNP-MB therapy was to be administered so as not to exceed the baseline $VO_2$ level by 50-75%.

Pretreatment protocol: the patient was transfused with 2 units of packed red blood cells 48 hours prior to undergoing treatment. Intravenous fluids (Lactated Ringer's solution) were administered at a rate of 100 cc/hour. The patient was dressed in comfortable cotton clothing and placed in an air-conditioned room. Equipment for monitoring heart rate and rhythm, temperature and oxygen consumption was utilized as outlined in Example 1. An oral breathing tube was used to conduct TEEM $VO_2$ measurements. Oxygen supplementation and "crash cart" was available at bedside.

Treatment protocol: baseline $VO_2$ measurements for 8 minutes established an average $VO_2$ of 250 cc/minute. DNP, at a dose of 2 mg/kg, was infused intravenously over a 2 minute period. Repeat $VO_2$ at 20 minutes was stabilized at 340-360 cc/minute. An additional 1 mg/kg DNP infusion was administered, and 15 minutes thereafter the $VO_2$ increased and stabilized at 420 cc/minute. Ten minutes thereafter, an infusion of methylene blue, 2 mg/kg (dissolved in a 0.4% pyrogen-free isotonic saline solution-35 ml) was administered over 20 minutes. Repeat $VO_2$ measurement at 20 minute intervals showed it to rise to and stabilize at 450-500 cc/minute.

By hour 3, $VO_2$ declined to the 360-380 cc/minute range. An additional 1 mg/kg dose of DNP was infused over a 2 minute period. Repeat $VO_2$ measurements 20 minutes after this infusion showed an increase in $VO_2$ back to the 450-500 cc/minute. Rectal probe temperature increased to a maximum of 1.3° C. over baseline. Blood pressure and cardiac rates remained within normal limits. The patient withstood the procedure without any adverse effects and therapy was terminated 6 hours after the initial DNP dose. The protocol was repeated every other day for a total of 15 treatments (30 days). Therapy was discontinued for 2 weeks and the cycle was again repeated for an additional 30 days, treatment being administered every other day.

Treatment outcome: there was no evidence of general toxicity at any time during treatment. The patient noted a decrease in his low back, hip and other areas of bone pain on the $6^{th}$ day following therapy. By 2 weeks, the patient was off all narcotic (morphine) analgesics and had a markedly increased appetite. On day 8, repeat PSA levels were increased by approximately 120% to 125 ng/ml. Acid phosphatase remained unchanged. All other blood chemistries, including CBC, showed no significant alterations.

At 6 weeks after treatment, repeat PSA values showed a significant decline to 30 ng/ml with a concomitant fall in serum acid phosphatase levels. At the final stage, 10 weeks after initiation of treatment, a prostatic biopsy was performed. Histologic examination revealed 95% of the tumor to be necrotic with only scattered or scarred acini containing an occasional malignant cell. There was a significant increase in stromal cells above that seen in his initial biopsy. One of the most striking changes noted by the pathologist was the formation of cyst-like structures within the epithelial cells. The patient was seen three months after initiation of therapy, at which time he had gained 8.2 kg of weight, remained pain free and stated that he felt "normal". FIG. 26 shows monitored treatment parameters. FIG. 27 shows biochemical, biopsy and clinical responses.

Oral DNP therapy (250 mg twice a day, daily for 5 days and recycled after no medication for 2 days) was initiated after his IV therapy and continued up to 4 months. A repeat prostate biopsy at the end of month 4 was obtained. Pathologic examination revealed disintegration of remaining tumor acini along with the formation of with many epithelial cysts. Occasional residual tumor cells were fractured and disrupted with markedly reduced cytoplasm. There was extensive fibrosis with an apparent increase in the number of stromal cells. Cytoplasm volume was significantly diminished in both the residual tumor and normal cells. Overall, there were very few intact acini or viable acinar cells.

EXAMPLE 10

Method of Using Dinitrophenol with Biologic Response Modifiers (in the Treatment of Hepatitis C Infection)

History: a 32 year old Investment Banker was evaluated for chronic Hepatitis C infection. She gave a past history of intermittent jaundice, dark urine, mild anorexia, nausea and vomiting. This episode occurred 10 years ago, approximately 3 months after a transfusion (3 units of packed red blood cells) for a cesarean section. She was currently asymptomatic, but on routine health insurance exam she was found to have elevations in her ALT and AST (alanine and aspartate aminotransferase) levels: 140 IU/L and 90 IU/L, respectively. She drank 5-8 glasses of wine, per week. Additional laboratory tests identified anti-HCV antibodies with an HCV-RNA level of $5 \times 10^6$/ml. The patient refused to undergo liver biopsy but agreed to treatment with interferon alpha-2b (3 million units injected subcutaneously 3 times per week) and ribavirin (500 mg orally—twice a day). After 12 weeks of treatment she developed lethargy, severe headaches, fever, nausea and depression. Anemia was detected with a hemoglobin concentration of 9.2 g/deciliter. As a result, her dosage of interferon was reduced to 1.5 million units 3 times a week and the dose of ribavirin was reduced to a total of 600 mg/daily. After 6 months of treatment her ALT and AST levels became normal and HCV-RNA became undetectable.

An additional six months of therapy however, failed to sustain her clinical improvement and she was found to have a relapse. Serum HCV-RNA levels rose to 5.2 million copies/ml and liver enzymes increased to 2.5-3 times that of the normal range. She was unable to tolerate any additional ribavirin because of severe anemia. She persistently refused to undergo a percutaneous liver biopsy.

Physical examination: WT=48 kg; HT=150 cm; BP=128/82; HR=76 & reg; R=18; T=37.5° C. Physical examination failed to reveal any signs of chronic liver disease. She was noted to have several scattered areas of scalp alopecia which she attributed to her anti-hepatitis C therapy.

Laboratory studies: EKG and chest x-ray were normal. CBC revealed a mild anemia with a hemoglobin of 10.2 and a hematocrit of 34%. WBC, differential and platelet count were within normal limits. Alkaline phosphatase was within normal limits. Serum AST and ALT were elevated to 2.5-3 times that of the upper normal limit. Serum HCV-RNA levels were found to be at 5.8 million copies/ml. The infecting hepatitis C strain was of genotype 1b. Antimitochondrial antibody serology was negative (titer less than 1:20). There were no other blood chemistry, hormone, or urine laboratory abnormalities.

Clinical assessment and treatment evaluation: the patient has a chronic Hepatitis C infection with relapse after combination ribavirin and interferon alpha-2b treatment. This is not uncommon in that the rate of relapse after an end-of-treatment response to interferon-ribavirin therapy may exceed 50%. She was unable to tolerate additional ribavirin therapy because of a related anemia.

Further, interferon dose escalation in non-responders to initial interferon therapy has only proved successful in a small number of cases. Despite her refusal to undergo any form of liver biopsy she agreed to undergo a combination of DNP and interferon therapy for a period of 12 weeks.

The liver is known to be one of the "hottest" organs in the human body. Liver temperatures exceeding 44° C. have been documented in humans undergoing strenuous exercise. The hepatitis C virus is an RNA encoded sphere containing several polyproteins comprising a capsid, 2 envelope proteins, and at least 6 enzymatic proteins with varied functions. Hepatitis C virus is known to be heat sensitive and is inactivated by standard blood banking heating techniques. Case reports of hepatitis C inactivation with the use of extracorporeal hyperthermia are known. It has been reported that HIV positive patients treated with extracorporeal hyperthermia, many of which were also positive for hepatitis C, the hepatitis C virus was cleared (as determined by serum viral PCR-RNA analysis).

Based on the this patients failure to respond to conventional treatment, anecdotal and case report studies showing beneficial results with whole body hyperthermia, the patient underwent a combination of DNP and interferon therapy. She was informed that she would undergo daily treatments with intravenous DNP for five days per week and receive interferon alpha at a dose of 1.5 million units subcutaneously every two days. This treatment protocol would continue until her hepatitis C-RNA blood viremia was no longer detectable.

Pretreatment protocol: each evening prior to treatment the patient was instructed not to eat after 7 pm and dress in cotton clothes. Approximately 6 hours prior to intravenous DNP administration she was to be given 1.5 million units of subcutaneous interferon-alpha every 3rd day. Repeat blood work, including CBC and platelet count, AST, ALT, and hepatitis C-RNA levels would be initially obtained at 48 hours and weekly thereafter. No efforts were to be made to prevent body heat loss. A single intravenous line was placed with a 21-gauge interacath. Heart rate, rectal thermistor, and $VO_2$ monitoring was conducted during therapy as outlined.

Treatment procedure: the patient presented herself for outpatient treatment and was given a subcutaneous dose of 1.5 million units of interferon-alpha. Approximately 6 hours thereafter, at 1 pm, a baseline $VO_2$ recording of 5 minutes was 160 cc/min. She was infused with 1 mg/kg DNP over a 2 minute period. At 20 minutes, her $VO_2$ increased and stabilized at approximately 210 cc/min. A second dose of 1 mg/kg DNP was infused and the $VO_2$ peaked 20 minutes later at 250 cc/min. An additional dose of 2.0 mg/kg DNP was given 30 minutes following the second dose. Repeat $VO_2$ showed a rise and stabilization 20 minutes thereafter at 360 cc/min. The patient's rectal temperature increased and never exceeded 1.3° C. above her normal baseline. Two hours after her last dose of DNP, her $VO_2$ declined to 280 cc/min. An additional 2 mg/kg dose of DNP was administered. The patients $VO_2$ increased and stabilized 20 minutes thereafter to a level of 420 cc/min. She was noted to sweat profusely. Throughout treatment the patient was permitted to drink fluids ad libitum. She was notably fatigued at hour 5 of therapy. Monitored parameters and flow chart are shown in FIG. 23. The 5 day treatment protocol was repeated after a 2 day "DNP rest period". This regimen was repeated times 3. Subcutaneous interferon-alpha was administered for a total of 10 weeks. FIG. 28 shows the patients DNP/interferon treatment flow chart.

Treatment outcome: by the treatment regimen outlined above, hepatitis C-RNA viral load decreased by approximately 2 logs after 48 hours. Over the next 5 days the viral load further decreased by an additional log. HCV-RNA became undetectable and the HCV viral genome remained cleared from the bloodstream at week 2 and thereafter. Alanine transaminase (ALT) levels increased 7 fold at 48 hours and remained elevated until week 3, at which time they returned to levels slightly below that which existed prior to therapy. CBC, bilirubin, and blood urea nitrogen (BUN) remained within normal limits. Alkaline phosphatase levels increased 2 fold at 48 hours but returned to pretreatment levels at day 7.

The patients HCV viral genome remained cleared from her bloodstream 18 months after therapy and there was normalization of her ALT.

EXAMPLE 11

Method of Using Dinitrophenol Induced Intracellular Hyperthermia to Increase Immunogenicity of Human Tumors DNP would be given as an intravenous solution, or as an oral preparation, so as to increase oxygen consumption 2.5-5 times above normal for a period of 2-3 hours. Such treatment would be administered every other day for a period of 5-10 days. At 8-24 hours after the last day of treatment, the patient would be administered standard chemotherapy or specific monoclonal antibody immunotherapy directed against known mutated or inappropriately expressed oncogenic proteins (e.g., ras, p53, HER/neu, etc.), or combination antioncogenic immunotherapy with chemotherapy or radiation.

Heat shock proteins (HSPs) or stress-induced proteins are constitutively expressed in all living cells and are among the most abundant proteins found. However, many members of the HSP family can further be expressed by cellular stress-causing conditions such as heat, drugs, glucose deprivation, etc. Of importance to the present method is that the expression of HSPs in tumors is associated with a heightened immune and/or cytotoxic T-lymphocyte response. In particular, it is known that members of the HSP70 family (HSPs are generally classified by their molecular weights e.g., HSP90 kdaltons, HSP27 kdaltons, HSP70 kdaltons, etc.) are expressed on cell surfaces. Due to the ability of DNP to induce intracellular hyperthermia, the enhanced expression of human HSPs in DNP treated tumors could greatly increase their immunogenicity.

This method could be used to broaden the antigen-specific repertoire of many poorly immunogenic tumors by increasing the expression of HSP-peptide immunogenic determinants on their cell surfaces. Such consequences would heighten any endogenous specific anti-tumor immune response. Moreover, DNP-intracellular heat-inducible immunogenic targets could further increase the efficacy of exogenously synthesized and administered monoclonal antibodies. By example, patients with HER-2/neu overexpressing metastatic breast cancer (25% of breast cancer patients) would be treated by the DNP method outlined above. This treatment would then be followed by a standard loading dose and weekly infusions of anti-HER-2/neu monoclonal antibodies. Clinical benefits would be evaluated by overall response rates and duration of response.

EXAMPLE 12

Synthesis and Use of Novel Conjugates and Derivatives of 2,4-Dinitrophenol

Formation of novel nitrophenol compounds is of importance in that their alkyl, alkene, fatty acid, aromatic and other derivatives may significantly enhance their biologic activity and/or improve the therapeutic index. Many reactions of the benzene ring of phenols through halogenation, sulfonation, and nitration are known. Numerous procedures for C-alkylation of phenols through reduction of benzylic alcohol, aldehydes, benzonitriles and Mannich bases are published.

Figure 30:
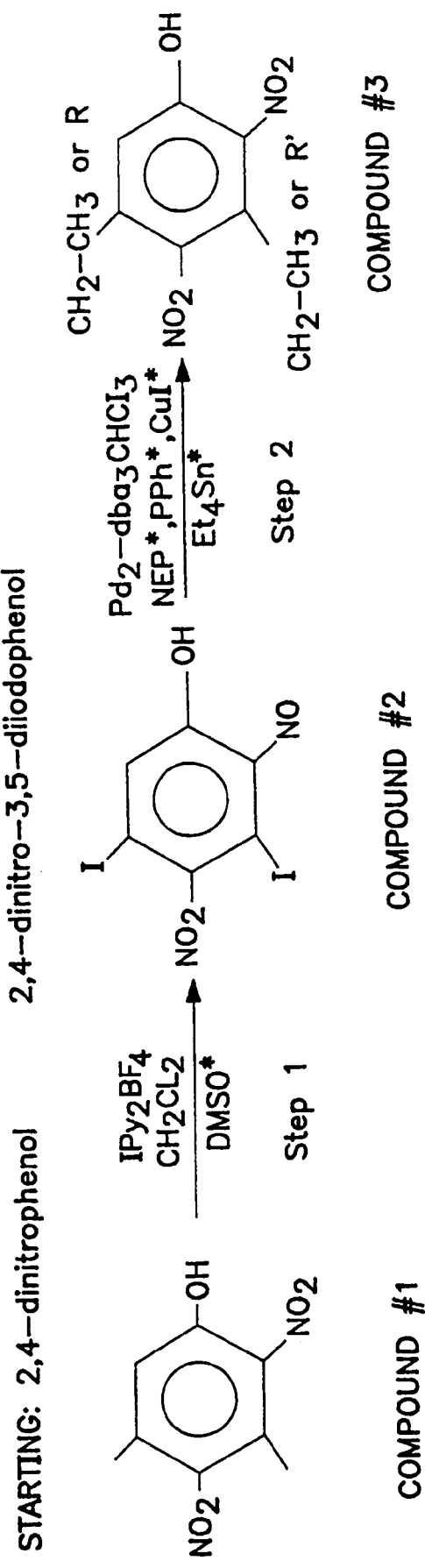
FIG. 30 shows an exemplary method of synthesis of novel 2,4-dinitrophenol conjugates and derivatives.
Figure 3I:
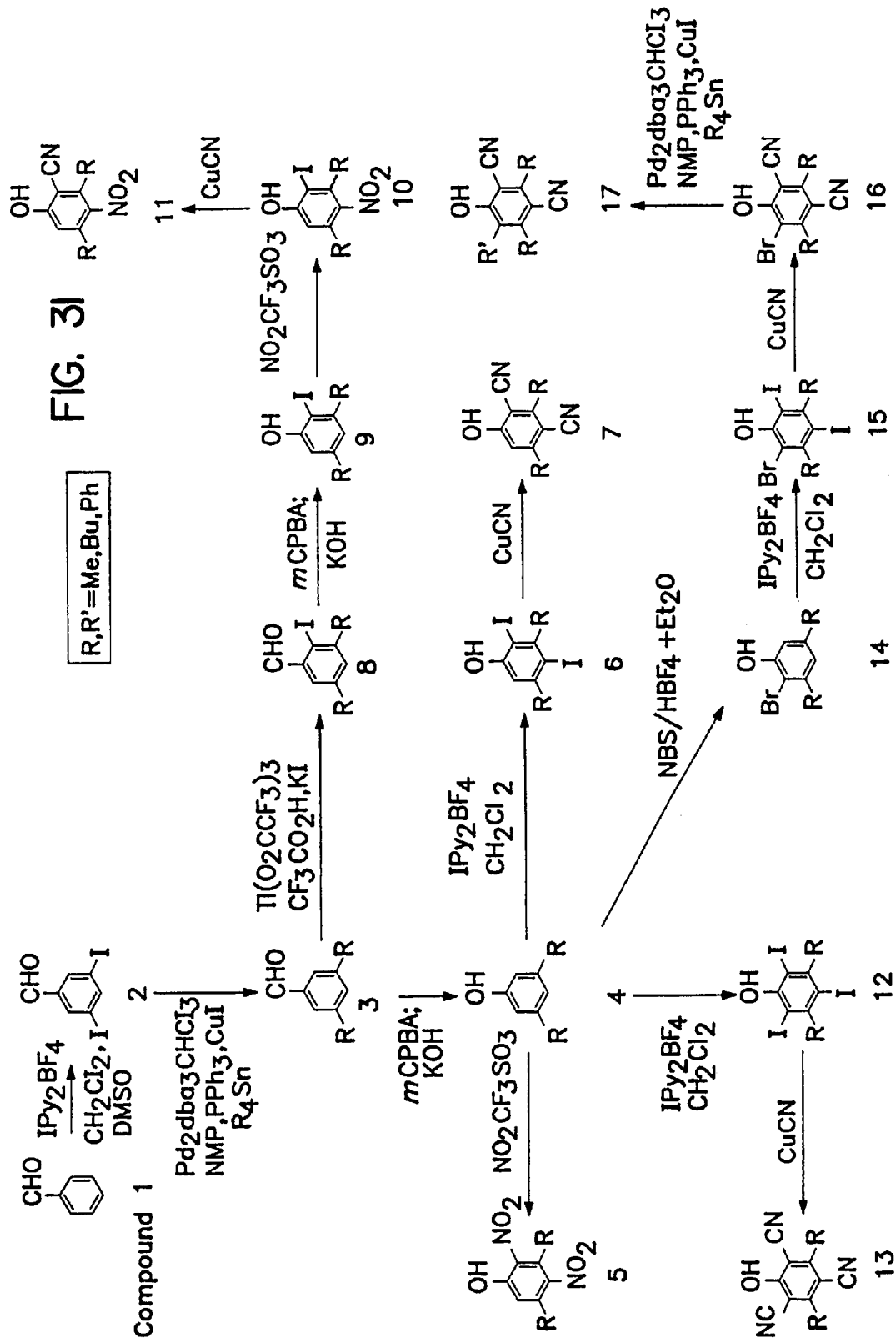

Alkylations or other "R" group additions have also been performed on various phenolic substrates using Stille or Negishi coupling reactions. An example of converting a nitrophenol compound to the desired alkylated (or other "R" group analog) by a 2 step procedure utilizing the Stille coupling reaction is illustrated in FIG. 30. As shown in step 1, DNP is first iodinated with Barluenga's reagent ($IPy_2BF_4$) to yield 2,4-dinitro-3,5-diiodophenol. In step 2, the nitroiodophenol is then converted to the alkylated derivative (in the instant example an ethylated derivative) via a co-catalytic, palladium-copper Stille reaction.

Compound 3 shown in FIG. 30 is an ethylated derivative of DNP and is designed to increase uncoupling activity by adding lipophilic alkyl substituents to the benzene ring. Such analogs with augmented activity may be particularly useful in the treatment of bulky tumors and malignancies which possess a high fat content, e.g. liposarcoma, glioblastoma, etc.

A representative approach (Step 2) to the palladium-copper, co-catalytic ethylation of a nitroiodophenol is illustrated by the conversion of 2,4-dinitro-3,5-diiodophenol to 2,4-dinitro-3,5-diethylphenol. Nitroiodophenol (500 mg, 9341 mmol) is added to a pressurized reaction to containing N-ethylpyrrolidinone (1.5 ml). $Pd_2dba_3CHCL_3$ (27 mg, 26 µmol) and triphenylphosphine (50 mg, 191 µmol) is added to the stirring solution and slowly heated to approximately 50° C. for 10 minutes. Copper iodide (17 mg, 91 µmol) is added to the stirring solution. The mixture is again heated to 50° C. for 10 minutes. The solution is cooled to 32° C. and tetraethyl tin (285 µL, 2.05 mmol) is added to the stirring solution. The reaction tube is sealed and heated with continuous stirring at 65° C. for 12-16 hours. Aqueous workup and ethyl acetate extraction with drying by magnesium sulfate ($MgSO_4$) and concentration yields the end product.

EXAMPLE 13

Synthesis of an Expanded Combinatorial Library of Putative Uncoupling Agents Capable of Inducing Intracellular Hyperthermia The spectrum of potential classic uncoupling agents that can induce intracellular hyperthermia can be greatly expanded through a designed convergent synthetic approach. An almost limitless variety of uncouplers can be synthesized through a "combinatorialized" scheme to produce an expanded "library" of uncoupling agents with related structures. The scheme specifically presented herein exemplifies the synthesis of 21 potential uncoupling agents, but can be expanded to 1,000 to 100,000 putative uncoupling agents.

Five classes of uncouplers are prepared via the convergent route shown in FIG. 31. The synthetic scheme depicted in FIG. 31 is designed as a combinatorial approach to allow access to a library of structurally related putative uncouplers for biological evaluation. While the given examples noted in FIG. 31 will allow formation of at least 21 novel uncouplers, a simple variation in this synthetic scheme will allow the library of uncouplers to be expanded to include from 1,000 to 100,000 novel uncoupling agents. After discussing the general synthetic approach in FIG. 31, the simple synthetic variations designed to expand the library of uncouplers will be described. Such variations will be apparent to those skilled in the art of synthetic organic chemistry and pharmaceutical development.

Starting from benzaldehyde (FIG. 31, Compound 1), diiodination at the 3- and 5-positions using Barluenga's reagent $(IPy_2BF_4)$ affords Compound 2 which is alkylated using a co-catalytic, palladium-copper Stille reaction to produce a 3,5-disubstituted Compound 3. This 2 step approach is known for producing a variety of methylated phenols. Use of tetramethyltin then produces the dimethyl derivatives [Compound 3, where R=Me (methyl)]; tetrabutyltin produces the dibutyl derivatives [Compound 3, where R=Bu (butyl)]; and, tetraphenyltin produces the diphenyl derivatives [Compound 3, where R=Ph (phenyl)]. A Baeyer-Villiger oxidation of Compound 3, with meta-chlorobenzoic peracid (mCPBA) followed by alkaline hydrolysis [KOH (potassium hydroxide)] of the resulting formate affords phenols, Compound 4. The homogeneous 2,4-dinitro- or 2,4-dicyano-derivatives are initially accessed from an intermediate Compound 4. Nitrosation of Compound 4 with nitrofluoromethylsulfonate salt $(NO_2CF_3SO_3)$ provides the 3,5-disubstituted-2,4-dinitrophenols shown in Compound 5. Three different uncoupling agents are produced via this synthetic route. Diiodination of Compound 4 at the 2- and 4-positions produces Compound 6 which is treated with copper(I) cyanide (CuCN) to give the 2,6-dicyanate derivative, Compound 7. Three additional uncouplers are synthesized by this route. The heterogeneous nitro-, cyano-uncouplers are also accessed from intermediate Compound 3. The 2-cyano-, 4-nitro-uncouplers are targeted as the steric effects of the cyano group at the 2-position is less than the corresponding 2-nitro-derivatives. Mono-iodination of Compound 3 through the thallium intermediate affords the selective 2-iodo-derivative, Compound 8. Conversion of Compound 8 to phenol, Compound 9, is accomplished as before through the Baeyer-Villiger oxidation and hydrolysis of the resulting formate. Selective 4-nitration to produce Compound 10 is readily accomplished with nitrotrifluoromethylsulfonate salt followed by cyanation to afford 2-cyano-, 4-nitro-uncouplers, Compound 11. Three additional uncouplers are produced by this route.

Additional uncouplers, such as the 2,4,6-tricyano compounds, can also be produced through the same convergent synthesis. Exhaustive iodination of Compound 4 affords 2,4,6-triiodinated Compound 12 which is then directly converted to tricyano-uncouplers, Compound 13, through copper catalyzed exchange. Three more uncouplers are produced by this modification. A 2,4-dicyano-uncoupler carrying three variable substituents at the 3-, 5- and 6-positions is also readily produced through this convergent approach. Initial selective monobromination of the phenol Compound 4 at the ortho-position affords Compound 14 which is diiodinated at the 2,4-positions to produce the 2,4-diiodo-, 6-bromo-Compound 15 derivatives. Selective cyano exchange at the more reactive aryliodide positions affords the dicyano Compound 16 derivatives. A final co-catalytic, palladium-copper Stille reaction results in the formation of the 3,5,6-trisubstituted, 2,4-dicyano-uncouplers. Use of the same tin reagents previously described allows the introduction of either methyl, ethyl, propyl, butyl, etc., or phenyl at the 6-position. In conjunction with the 3 different substituents at the 3- and 5-positions, 9 additional uncouplers are afforded by this additional expansive route.

The synthesis of 21 novel uncouplers depicted by the convergent approach in FIG. 31 can be further modified. To those skilled in the art, a simple variation in this exemplary synthetic approach will allow a greatly expanded library of potential uncouplers to be synthesized. The expanded library can be produced by introduction of an array of alkyl and aryl substituents at the 3-, 5-, and/or 6-positions while maintaining the 2,4-dinitro-, 2,4-dicyano, 2-cyano-4-nitro-, and/or the 2,4,6-tricyano-phenol substrate. This simple synthetic variation is accomplished by using a variety of well known palladium, zinc, or copper-mediated reactions at the stage of alkyl or aryl group incorporation, i.e., FIG. 31, Compound 2 to 3 and Compound 16 to 17 conversions. This synthesis is a variation on the Stille reaction, the Heck reaction, the Negishi coupling, Suzuki couplings, Semmelhack reactions and cuprate reactions. Such a variation can introduce a nearly of unlimited array of potential substituents onto the phenol core of the uncoupler. This combinatorial approach can even be further expanded by variable halogenation (either bromination or iodination) at the 3- and 5-positions to allow 2 different substituents to be introduced at these 2 positions in the ensuing metal-mediated halogen exchange reactions. This "combinatorial library" approach will allow a broad range of potential uncouplers to be synthesized and evaluated for potential biological activity, including safety and effectiveness.

Activity of the many diverse conjugates and derivatives of 2,4-dinitrophenol (and other uncoupling agents) may be tested by known in vitro methods for oxygen consumption, e.g., tissue or cellular suspensions with Clark type oxygen sensors. Toxicity, mutagenicity and LD50 studies in animals would be performed under recognized protocols prior to use of any such novel compounds in human subjects. Upon establishing toxicity and safety criteria, the various novel conjugates and derivatives can be administered under dose escalation trials as outlined previously for the clinical use of dinitrophenol.

It will be apparent to those skilled in the art that numerous modifications and variations can be made to the processes and compositions of this invention. Thus, it is intended that the present invention cover the modifications and variations of this invention provided they come within the scope of the appended claims and their equivalents.

REFERENCES

1.) Coley, W. B. (1893) "The Treatment of Malignant Tumors by Repeated Inoculations of Erysipelas" Am. Journal Medical Science; 105: 487-511.
2.) Sartin, J. S., Perry, O. H. (1995) "From Mercury to Malaria to Penicillin: The History of the Treatment of Syphilis at the Mayo Clinic-1916-1955" Journal of the American Academy of Pharmacology, February.
3.) O'Leary, P. A. (1955) "Neurosyphilis II: Treatment" Baker, A. B., Editor. Clinical Neurology. Volume 2. New York: Haeber-Harper: 846-865.
4.) Westermark, F. (1898) "Uber die Behandlung de Ulcerinded Cervixcarcinomas" Mittel Kontanter Warme. Zbe Gynak: 1335-1339.

5.) Busch, W. (1866) "Uber den Einfluss Welchen Heftigese Erysiphelen Zuwelen AVF Organisiete Neubildungen Amiben" Verhandlungen de Naturh: Preuss Rheinl; 23: 28-30.

6.) Suer, R. P., Fisher, W. B. et al. (1980) "Burkitt's Lymphoma: Tumor Lysis Following Malignant Hyperthermia" Cancer Treatment Reports: Volume 64. No. 2-3, February/March.

7.) Tsueda, K., Dubick, M. N. et al. (1978) "Intraoperative Hyperthermia Crisis in Two Children With Undifferentiated Lymphoma" Anesth. Analg. 57: 511-14.

8.) Green, I. (1991) "Hyperthermia Alone or Combined With Chemotherapy for the Treatment of Cancer" Hyperthermia in Conjunction with Cancer Chemotherapy, No. 2, AHCPR, Health Technology Assessment Reports, U.S. Department of Heath and Human Services.

9.) Overgaard, J., Gonzalez, M. C. et al. (1995) "Randomized Trial of Hyperthermia as Adjuvant to Radiotherapy for Recurrent or Metastatic Melanoma" The Lancet; 345: 540-43.

10.) Maeda, M., Watanabe, N., Yamauchi, N. et al. (1991) "Successful Treatment of a Case of Hepatocellular Carcinoma with Tumor Necrosis Factor and Local Hyperthermia" Gastroenterologia Japonica, Volume 26, No. 6: 774-778.

11.) Kitamura, K., Kwano, H., Watanabe, M. et al. (1995) "Prospective Randomized Study of Hyperthermia Combined with Chemoradiotherapy for Esophageal Carcinoma" Journal Surg. Oncol. September; 60 (1): 55-8.

12.) Kitamura, M., Sumiyoshi, K., Sonoda, K. et al. (1997) "The Clinical and Histopathological Contributing Factors Influencing the Effectiveness of Preoperative Hyperthermo-chemo-Radiotherapy for the Patients with Esophageal Cancer" Hepatogastroenterology, January/February; 44 (13): 175-180.

13.) Pontiggia, P., Curto, C. F. et al. (1995) "Is Metastatic Breast Cancer Refractory to Usual Therapy Curable?" Biomed. and Pharmacother. 49; 79-82.

14.) Myer, J. L. (1984) "Hyperthermia—A Historical Perspective". Front Radiat. Ther. Oncol. 18:1-22.

15.) Fujimoto, S. et al. (1997) "Improved Mortality Rate of Gastric Carcinoma Patients with Peritoneal Carcinomatosis Treated with Intraperitoneal Hyperthermia Chemoperfusion Combined with Surgery". Cancer Mar. 1; 79(5): 884-91.

16.) Ohno, S., Tomoda, M. et al. (1997) "Improved Surgical Results After Combining Preoperative Hyperthermia with Chemotherapy and Radiotherapy for Patients with Carcinoma of the Rectum". Dis. Colon Rectum April; 40 (4): 401-6.

17.) Gautherie, M. (Ed.), Robins, H. I., Cohen, J. D., Nevelle, A. J. (1997) "Whole Body Hyperthermia Biologic and Clinical Aspects. Clinical Thermology, Subseries Thermotherapy. New York; Springer-Verlag. 41-46.

18.) Donato, V. et al. (1997) "Multicentre Experience with Combined Hyperthermia and Radiation Therapy in the Treatment of Superficially Located Non-Hodgkin's Lymphomas" J. Exp. Clin. Cancer Res. 16(1):87-90.

19.) Kim, S. et al. (1976) "The Enhanced Killing of Irradiated HeLa Cells in Synchronous Culture by Hyperthermia" Br. J. Radiol. 48: 872-874.

20.) Moriyama, Y. et al. (1986) "Application of Hyperthermia to the Treatment of Human Acute Leukemia Purging Human Leukemic Progenitor Cells by Heat" Blood, Vol. 67, 3:802-804.

21.) Urano, M. (1988) "Tumor Response to Hyperthermia" Hyperthermia and Oncology, Vol. I, Urano, M. and Douple, E. Eds., NSP BV. 162-200.

22.) Moyalan, D. J. et al. (1989) "Hyperthermia-Scientific Basis and Clinical Applications" Therapeutic Radiology, Manfield, C. M. Ed., Elsevier-N.Y. 531-541.

23.) Buell, J. F. et al. (1997) "Synergistic Effect and Possible Mechanisms of Tumor Necrosis Factor and Cisplatin Cytotoxicity Under Moderate Hyperthermia Against Gastric Cancer Cells" Ann. Surg. Oncol. 4 (2): 141-8.

24.) Crile, G. (1963) "The Effects of Heat and Radiation on Cancers Implanted on the Feet of Mice" Cancer Res. 23: 372-380.

25.) Brown, M. R. W. et al. (1971) "Inhibition and Destruction of Microorganisms by Heat" Hugo, W. B. Ed., Inhibition and Destruction of the Microbial Cell. Academic Press, New York. 1-37.

26.) Brand, P. W. (1959) Int. J. Lepr. 27:1.

27.) Storrs, E. E. (1971) Int. J. Lepr. 39:703

28.) Muir, E. (1948) Manual of Leprosy. Baltimore, Williams & Wilkins.

29.) Bierman, W. (1942) "The History of Fever Therapy in Treatment of Disease" Bull NY Acad. Med. 18:65-75.

30.) Hollander, D. H. et al. (1959) Am. J. Syphilis 3, 8:489.

31.) Schwemlein, T. J. et al. (1948) Journal American Med. Assoc. 137: 1209.

32.) White, H. J. et al., (1938) J. Bacteriol. 36: 481.

33.) Simon, H. B. et al., (1996) "Pathophysiology of Fever and Fever of Undetermined Origin" Scientific American Medicine Vol. 2. Dale, D. C. et al. Eds. Scientific American, New York, Section 7, Subsection XXIV, 4.

34.) Sutherland, G. E. et al. (1980) "Heat Treatment for Certain Chronic Granulomatosis Skin Infections" Southern Med. J. 73, 12: 1564-1565.

35.) Hiruma, M. et al. (1992) "Hyperthermic Treatment of Sporotrichosis" Mycoses, 35: 293-299.

36.) Thomas, C. C. et al. (1951) "Sporotrichosis Responding to Fever Therapy" JAMA 147: 1342-1343.

37.) Rodbard, D. et al. (1980) "Temperature: A critical Factor Determining Localization and Natural History of Infectious, Metabolic, and Immunological Diseases" Perspectives in Biology & Medicine, Spring. 439-474.

38.) Mackinnon, J. E. (1968) "Systemic Mycosis", Wolstenholme, G. E., and Porter, R. (Eds.) Boston: Little, Brown.

39.) Mackinnon, J. E. et al. (1962) Sabouraudia, 2:31.

40.) Silva, M. (1958) "Fungi and Heat Sensitivity" Trans. N.Y. Acad. Sci., 2d series, 21: 46

41.) Dubos, R. J. (1952) "Bacterial and Mycotic Infections of Man" $2^{nd}$ ed. Philadelphia: Lippencott.

42.) Kuhn, L. R. (1939) "Growth and Viability of *Cryptococcus neoformans* at Mouse and Rabbit Body Temperatures" Proc. Soc. Exp. Biol. Med. 41:573-574.

43.) Samady, J. A. et al. (1996) "Cutaneous and Mucocutaneous Leishmaniasis" Cutis 57:13-20

44.) Sacks, D. L. et al. (1983) "Thermosensitivity Patterns of Old vs New World Cutaneous Strains of *Leishmania* Growing within Mouse Peritoneal Macrophages In Vitro" Am. J. Trop. Med. Hyg. 32(2):300-304.

45.) Junaid, A. J. N. (1986) "Treatment of Cutaneous Leishmaniasis With Heat" Int. J. Dermatol. 25:470-472.

46.) Kakahashi, M. (1992) "Effect of Thermochemotherapy on Alveolar Hydadid Disease of the Liver" J. of the Japanese Surg. Soc., 93(2):150-157.

47.) Baron, S. (1963) "Mechanism of Recovery from Viral Infection" Advan. Virus Res. 10:39-64.

48.) Kim, A. et al. (1983) "How Viruses May Overcome Non-specific Defense in the Host" Phil. Trans. R. Soc. Lond. B303, 115-122.
49.) Fenner, F. et al (1976) Medical Virology 2d ed. New York: Academic Press.
50.) Schmidt, J. R. et al (1960) "Temperature Effect on Herpes Simplex" J. Infect. Dis. 107:356-360.
51.) Vaczi, I. Et al. (1963) "Influence of Temperatures on the Multiplication of Varicella Virus" ACTA Virol. (Prague) 12:109-115.
52.) Carter, W. A. et al. (1974) "Viral Infection and Host Defense" Science, 186:1172-1177.
53.) Schweitzer-Thumann, C. et al. (1994). "Effect of an Elevated Temperature on the Replication of HIV-1 and Monocytic Cell Line" Res. Virol. 145:163-170.
54.) Lee, M. H. et al. (1996) "HIV-1 Load is Decreased in Chronic Infected ACH-2 Cell Line by Successive In Vitro Hyperthermia Treatment" XI International Conference On AIDS, Vancouver, Canada
55.) Wong, G. H. et al. (1991) "Tumor Necrosis Factor α Selectively Sensitizes Human Immunodeficiency Virus-Infected Cells to Heat and Radiation" Proc. Natl. Acad. Sci. USA 88:4372-4376.
56.) Alonso, K. et al. (1994) "Systemic Hyperthermia in the Treatment of HIV-Related Disseminated Kaposi's Sarcoma" Am. J. Clin. Oncol 17(4):353-359.
57.) Alonso, K. et al. (1995) "Whole Body Hyperthermia and the Augmentation of Cellular Cytotoxic Responses in the Treatment of Acquired Immune Deficiency Syndrome" Southern Med. J. 88:S142.
58.) Schecterle, L. M. et al. (1995) "Potential Role of Whole Body Hyperthermia to Treat Lyme Disease" Southern Med. J. 88:S142-143.
59.) Stone, R. (1993) "CDC Chokes on AIDS Treatment Proposal" Science 260:883.
60.) Ash, S. R. et al. (1994) "The Biologic-HT Sorbent System Maintains Normal Blood Chemistries During Whole-Body Hyperthermia" American Society for Artificial Internal Organs, 40th Anniversary Meeting, San Francisco, Calif.
61.) Kakinuma, K. et al. (1996) "Drug Delivery to the Brain Using Thermosensitive Liposome and Local Hyperthermia" Int. J. Hyperthermia 12(1):157-165.
62.) Iga, K. (1992) "Optimum Formation of Thermosensitive Liposome for Targeted Tumor Drug Delivery" J. of Takeda Research Lab. 5:45-72.
63.) Merlin, J. L. (1993) "Antiproliferative of Thermosensitive Liposome-Encapsulated Doxorubicin Combined with 43° C. Hyperthermia in Sensitive and Multi-Drug Resistant MCT-7 Cells" Eur. J. Cancer 29A:2264-2268.
64.) Kizer, K. W. (1992) "A Simple Solution to Scorpaenidae Stings" Emergency Medicine July, 209A-210-B.
65.) Hudgens, T. L., Turnbull, K. D. (1998) "C-Methylation of Phenols, Tyrosine Derivatives, and a Tyrosine Containing Peptide" Tetrahedron Letters 40:2719-2722.
66.) Cortopassi, G. et al. (1995) "Modelling the Effects of Age-Related mtDNA Mutation Accumulation: Complex I Deficiency, Superoxide and Cell Death" Biochem. Biophys. Acta 1271:171-176.
67.) Koga, S. et al. (1990) "Extracorporeally Induced Total-Body Hyperthermia for Disseminated Cancer" Adv. Exp. Med. Biol. 267:177-188.
68.) Parks, L. C. et al. (1979) "Treatment of Far-Advanced Bronchogenic Carcinoma by Extracorporeally Induced Systemic Hyperthermia" J. Cardiovasc. Surg. 78:883-892.
69.) Vertrees, R. E. et al. (1996) "Induction of Whole Body Hyperthermia and Venovenous Perfusion" American Society for Artificial Internal Organs J. 42(4):250-4.
70.) Pontiggia, P. et al. (1995) "Whole Body Hyperthermia Associated with Betacarotene Supplementation in Patients with AIDS" Biomed. And Pharmacother 5:263-265.
71.) Müller-Scholte, D. P. et al (1996) "AIDS Therapy Using Encapsulated Magnetic Nanoparticles" RWTH-AACHEN, Rechnerbetrieb Informatik, Germany. (German Patent #?)
72.) Cole, N. H. (1994) "Hyperthermia as Adjuvant Treatment for Recurrent Breast Cancer and Primary Malignant Glioma" JAMA 271(10):797-802.
73.) Gilden, D. (1995) "Hyperthermia. Study Finds Little Effect" GMHC Treat Issues 9:11.
74.) Roizen-Towle, L. et al. (1988) "Thermotolerance in Human Cells of Normal and Neoplastic Origin" Int. J. Hyperthermia 4(6):665-675.
75.) Gerwick, L. E. et al. (1980) "Influence of pH on the Response of Cells to Single and Split Doses of Hyperthermia" Cancer Research 40:4019-4024.
76.) Hirokawa, K. et al. (1997) "Effect of Lactic Acid in Tumors on Anti-tumor Activity of Hyperthermia" Int. J. Hyperthermia 13(11):115-123.
77.) Yoshikawa, T. et al. (1993) "The Role of Active Oxygen Species and Lipid Peroxidation in the Anti-tumor Effect of Hyperthermia" Cancer Research 53:2326-2329.
78.) Kang, S. et al. (1994) "Debilitating Verruca vulgaris in a Patient Infected with the Human Immunodeficiency Virus: Dramatic Improvement with Hyperthermia Therapy" Arch Dermatol. 130:294-296.
79.) Calderwood, S. K. et al. (1987) "Thermal Injury Causes Stimulation of Phospholipase $A_2$ Activity in Mammalian Cells" Walden, T. ed. Prostaglandin and Lipid Metabolism in Radiation Injury. New York, N.Y.: Plenum Press; 201-206.
80.) Stephenson, M. A. et al. (1986) "Rapid Increase in Inositol Triphosphate and Intracellular $Ca^{+2}$ After Heat Shock" Biochem. Biophys. Res. Commun. 137:826-833.
81.) Kroemer, G. et al. (1995) "The Biochemistry of Programmed Cell Death" The FASEB Journal 9:1278-1287.
82.) Decaudin, D. et al. (1997) "Bcl-2 and Bcl-$X_L$ Antagonize the Mitochondrial Dysfunction Preceding Nuclear Apoptosis by Chemotherapeutic Agents" Cancer Res. 57:62-67.
83.) Zamzami, N. et al. (1996) "Mitochondrial Control of Nuclear Apoptosis" J. Exp. Med. 183:1533-1544.
84.) Henry, K. et al. (1996) "Acute Effects of Whole Body Hyperthermia (WBH) on Plasma HIV RNA Levels" 3rd Conf. Retro. And Opportun. Infect. 1:122.
85.) McLaren, J. E. et al. (1990) "Consensus on Hyperthermia for 1990's" Adv. Exper. Med. Biol. 267:21-36.
86.) Sessler, D. I. et al (1990) "Skin-Surface Warming: Heat Flux and Central Temperature" Anesthesiology 73:218-224.
87.) Gordon, R. T. et al. (1979) "Intracellular Hyperthermia" Medical Hippothesis 5:83-102.
88.) Gonzalez, G. D. et al. (1995) "Radiotherapy and Hyperthermia" Eur. J. Cancer 31A (7-8):1351-1355.
89.) Strohbehn, J. W. (1994) "Hyperthermia Equipment Evaluation" Int. J. Hyperthermia 10(3):429-432.
90.) Multhoff, G. (1997) "Heat Shock Protein 72 (HSP72), A Hyperthermia-Inducible Immunogenic Determinant On Leukemic K562 and Ewing's Sarcoma Cells" Int. J. Hyperthermia 13:39-48.
91.) Brooks, G. A. et al. (1971) "Temperature, Skeletal Muscle Mitochondrial. Functions, and Oxygen Debt" Am. J. Physiol. 220:1053-1059.

92.) Brooks, G. A. et al. (1971) "Tissue Temperatures and Whole Animal Oxygen Consumption After Exercise" Am. J. Physiol. 221:427-431.

93.) Hynynen, K. et al. (1997) "Thermal Effects of Focused Ultrasound on the Brain: Determination with MR Imaging" Radiology 204(1):247-53.

94.) Skinkal, M. et al. (1996) "Intracellular Hyperthermia for Cancer Using Magnetic Cationic Liposomes In Vitro Study" Jpn. J. Cancer Res. 87(11):1179-83.

95.) Khogali, M. et al. (1993) "Heat Stroke and Temperature Regulation" (eds M. Khogali and J. R. S. Hales). Academic Press, Sydney.

96.) Benndorf, R. et al. (1997) "Cellular Stress Response: Stress Proteins-Physiology and Implication for Cancer" Recent Results Cancer Res. 143:129-144.

97.) Sneed, P. K. et al, (1998) "Survival Benefit of Hyperthermia in A Prospective Randomized Trial of Brachytherapy Boost+/–Hyperthermia for Glioblastoma Multiforme" Int. J. Radiat. Oncol. Biol. Phys. 40(2):287-95.

98.) Dahl, O. (1996) "Interaction of Heat and Drugs in vitro and in vivo" in Seegenschmidt, M. H., Vernon, C. C. (eds): Thermoradiotherapy and Thermochemotherapy, Vol 1. Berlin, Germany, Springer, 103-122.

99.) Hauck, M. L. et al (1995) "Enhancement of Radiolabeled Monoclonal Antibody Uptake in Tumors with Local Hyperthermia" in Torchlin, V. P. (ed): Targeted Delivery of Imaging Agents. Boca Raton, Fla., CRC, 335-361.

100.) Dewhirst, M. W. et al (1997) "Hyperthermic Treatment of Malignant Disease: Current Status and a View Toward the Future" Seminars in Oncology, 24 (6):616-625.

101.) Gaber, M. H. et al, (1996) "Thermosensitive Liposomes: Extravasation and Release of Contents in Tumor Microvascular Networks" Int. J. Radiat. Oncol. Biol. Phys. 36:1177-1187.

102.) Kato, H. et al (1998) "Research and Development of Hyperthermia Machines for Present and Future Clinical Needs" Int. J. Hyperthermia 14(1): 1-11.

103.) Clegg, S. T. et al, (1996) "Verification of a Hyperthermia Model Method Using MR Thermometry" Int. J. Hyperthermia, 11: 409-424.

104.) Keyserlingk, J. R. (1998) "Is It Time To Reassess the Value of Infrared Breast Imaging" Primary Care & Cancer, February Issue, 9.

105.) Kamiya, M. et al (1998) "A Case of Cutaneous Pseudallescheriosis Resembling Sporotrichosis" Nippon Ishinkin Gakkai Zasshi, 39(1):33-36.

106.) Youngblood, D. et al (1998) "First Circle Tries to Advance" Minneapolis Star Tribune, April 13 Issue, page D2.

107.) Szreder, Z. et al (1991) "A comparative Study on the Thermoregulatory Effects of Prazosin, Dihydrobenzperidol and Nifedipin on 2,4-Dinitrophenol Induced Hyperthermia in Rabbits" Gen. Pharmac., Vol. 22(6):1139-1142.

108.) Koga, S. et al (1990) "Extracorporeal Induced Total-Body Hyperthermia for Disseminated Cancer" Adv. Exp. Mod. Biol., 267:177-188.

109.) Robins, H. I. et al (1990) "Whole Body Hyperthermia in the Treatment of Neoplastic Disease" Radiol. Clin. North, 17(3):603-610.

110.) Thrall, D. E. et al (1990) "A Comparison of Temperature in Canine Solid Tumors During Local and Whole-Body Hyperthermia Administered Alone and Simultaneously" Int. J. Hyperthermia, 6(2):305-317.

111.) Raaphorst, G. P. et al (1994) "Hyperthermia Radiosensitization in Human Glioma Cells Comparison of Recovery of Polymerase Activity Survival, and Potentially Lethal Damage Repair" Int. J. Radiat. Oncol. Biol. Phys., 29(1): 133-139.

112.) Eisler, K. et al (1990) "New Clinical Aspects of Whole Body Hyperthermia" Adv. Exp. Med. Biol. 267:393-398.

113.) Thrall, D. E. et al (1989) "Whole Body Hyperthermia in Dogs Using a Radiant Heating Device: Effect of Surface Cooling on Temperature Uniformity" Int. J. Hyperthermia 5(2):137-143.

114.) Young, R. A. et al (1989) "Stress Proteins, Infection, and Immune Surveillance" [Review] Cell 59(1): 5-8.

115.) Lindquist, S et al (1988) "The Heat Shock Proteins" [Review] Annu. Rev. Genet. 22:631-677.

116.) Henle, K. J. et al (1980) "Time-Temperature Conversions in Biological Applications of Hyperthermia" Radiat. Res. 82(1):138-145.

117.) Riviere, J. E. et al (1986) "Effect of Hyperthermia on Cisplatin Pharmokinetics in Normal Dogs" Int. J. Hyperthermia. 2(4):351-358.

118.) Santinami, M. et al (1989) "Seven Year Experience with Hyperthermic Perfusion in Extracorporeal Circulation for Melanoma of the Extremities" J. Surg. Oncol. 42(3):201-208.

119.) Yerushaimi, A. et al (1982) "Antitumor Effects of Combined Interferon and Hyperthermia in Mice" Proc. Soc. Exp. Biol. Med. 169(3)-413-415.

120.) Kerr, J. F. et al 1994 "Apoptosis. Its Significance in Cancer and Cancer Therapy" (Published erratum appears in Cancer 1994 Jun. 15; 73(12):3108) [Review] Cancer 73(8):2013-2026.

121.) Kozak, W. (1993) "Fever a Possible Strategy for Membrane Homeostasis During Infection" [Review] Perspect. Biol. Med. 37(1):14-34.

122.) Villar, J. et al (1994) "Induction of the Heat Shock Response Reduces Mortality Rate and Organ Damage in a Sepsis-Induced Acute Lung Injury Model" (See Comments) Crit. Care Med. 22(6):914-921.

123.) Page, R. I. et al (1994) "Effect of Whole Body Hyperthermia on Carboplatin Disposition and Toxicity in Dogs" Int. J. Hyperthermia 10(6):807-816.

124.) Jain, R. K. et al (1994) "Barriers to Drug Delivery in Solid Tumors" [Review] Sci. Am. 271(1):93-127.

125.) Bowler, K. (1981) "Heat Death and Cellular Heat Injury" J. Therm. Biol. 6:171-178.

126.) Heron, I. et al (1978) "The Actions of Interferon are Potentiated at Elevated Temperatures" Macmillan Journals Ltd. Nature 274:508-510.

127.) Parks, L. C. et al (1995) "Systemic Hyperthermia by Extracorporeal Induction: Techniques and Results. In: Unk. Anonymous. Pp 407-446.

128.) Harmon, B. V. et al (1990) "Cell Death Induced in a Murine Mastocytoma by 42-47 Degrees C. Heating in Vitro Evidence that the Form of Death Changes from Apoptosis to Necrosis above a Critical Heat Load" Int. J. Radiat. Biol. 58(5):845-858.

129.) Gabriele, P. et al (1990) "Hyperthermia Alone in the Treatment of Recurrences of Malignant Tumors. Experience with 60 lesions" Cancer 66(10):2191-2195.

130.) Brinnel, H. et al (1987) "Enhanced Brain Protection During Passive Hyperthermia in Humans" Eur. J. Appl. Physiol. 56(5):540-545.

131.) Harmon, B. V. et al (1991) "The Role of Apoptosis in the Response of Cells and Tumors to Mild Hyperthermia" Int. J. Radiat. Biol. 59(2):489-501.

132.) Cohen, J. D. et al (1990) "Whole Body Hyperthermia and Intraperitoneal Carboplatinum in Residual Ovarian Cancer" In: Bicher, H I, McLAren, J. R., Pigluicci, G. (eds)

Consensus of Hyperthermia for the 1990's: Advances in Medicine and Biology Series. Plenum, New York, pp 197-202.

133.) Sellins, K. S. et al (1991) "Hyperthermia Induces Apoptosis in Thymocytes (published erratum appears in Radiat. Res. 1992 March: 129(3); 370-371). Radiat. Res. 126(1):88-95.

134.) Freeman, M. L. et al (1977) "Effects of pH on Hyperthermic Cell Survival" J. Natl. Cancer Inst. 5B(6):1837-1839.

135.) Kamura, T. et al (1982) "Development of Thermotolerance During Fractionated Hyperthermia in a Solid Tumor in Vivo" Cancer Res. 42(5):1744-1748.

136.) Reisinger, E. et al (1996) "Antibiotics and Increased Temperatures Against *Borrelia Burgdorferi* in vitro" Scand. J. Infect. Dis. 28(2):155-7.

137.) Schecterle, L. M. et al (1995) "Altered Lipid Metabolism with Hyperthermia" FASEB 9(4):A646.

138.) Groom, R. C. et al (1987) "Hyperthermic Cancer Treatment: Systemic Hyperthermia and Isolated Limb Perfusion" Proc. Am. Aca. Of Cardiov. Per. 8:105-111.

139.) Yang, H. X. et al (1991) "Hyperthermic Inactivation, Recovery and Induced Thermotolerance of Human Natural Killer Cell Lytic Function" Int. J. Hyperthermia 7(1):35-49.

140.) Arkin, H. et al (1994) "Recent Developments in Modeling Heat Transfer in Blood Perfused Tissues" [Review] IEEE Trans. Biom. Eng. 41(2):97-107.

141.) St. Cyr et al (1996) "Whole Body Extracorporeal Low Flow Hyperthermia in a Canine Model" J. Extracorporeal Technology 28(3):140-146.

142.) Macy, D. W. (1985) "Physiological Studies of Whole-Body Hyperthermia of Dogs" Cancer Res. 45:2769-2773.

143.) Schecterle, L. M. et al (1995) "Could Whole Body Hyperthermia Offer a Treatment Option in Lyme Disease?" Alternative Med. J. pp 19-20.

144.) O'Leary, P. S. (1927) "Treatment of Neurosyphilis by Malaria: Report on the Three Year Observation of the First One Hundred Patients Treated" JAMA 89:95-100.

145.) Field, S. B. et al (1983) "The Relationship Between Heating Time and Temperature: Its Relevance to Clinical Hyperthermia" Rediother. Oncol. 1:179-186.

146.) Omar, R. A. et al (1987) "Antioxidant Enzymes and Survival of Normal and Simian Virus 40-Transformed Mouse Embryo Cells After Hyperthermia" Cancer Res. 47:3473-3476.

147.) Rowell, L. B. (1974) "Human Cardiovascular Adjustments to Exercise and Thermal Stress" [Review] Physiol. Rev. 5(1):75-159.

148.) Nadel, E. R. et al (1979) "Circulatory Regulation During Exercise in Different Ambient Temperatures. J. Appl. Physiol. 46(3):430-437.

149.) Frey, M. A. et al (1979) "Cardiac Response to Whole-Body Heating" Aviat. Space Envirn. Med. 50(4):387-389.

150.) Rowell, L. B. (1983) "Cardiovascular Aspects of Human Thermoregulation" [Review] Circ. Res. 52(4):367-379.

151.) Rowell, L. B. (1972) "Importance of the Splanchnic Vascular Bed in Human Blood Pressure Regulation" J. Appl. Physio. 32(2):213-220.

152.) Page, R. L. et al (1994) "Therapeutic Hyperthermia: Contribution from Clinical Studies in Dogs with Spontaneous Neoplasia" [Review] In Vivo 8(5):851-858.

153.) Gillette, S. M. et al (1992) "Response of Canine Soft Tissue Sarcomas to Radiation or Radiation Plus Hyperthermia: A Randomized Phase II Study" Int. J. Hyperthermia 8(3):309-320.

154.) Thrall, D. E. et al (1992) "Serious Toxicity Associated with Annular Microwave Array Induction of Whole-Body Hyperthermia in Normal Dogs" Int. J. Hyperthermia 8(1):23-32.

155.) Meyer, R. E. et al (1991) "Effect of a Passive Heat and Moisture Exchanger on Esophageal Temperature in Tumor-Bearing Dogs During Whole-Body Hyperthermia" Am. J. Vet. Res. 52(10):1688-1691.

156.) Page, R. L. et al (1991) "Phase I Study of Melphalan Alone and Melphalan Plus Whole Body Hyperthermia in Dogs with Malignant Melanoma" Int. J. Hyperthermia 7(4):559-566.

157.) Herman, T. S. et al (1982) "Effect of Heating on Lethality Due to Hyperthermia and Selected Chemotherapeutic Drugs" J. Natl. Cancer Ins. 68(3):487-491.

158.) Overgaard, J. et al (1983) "The Importance of Thermotolerance for the Clinical Treatment with Hyperthermia" Radiother. Oncol 1(2):167-178.

159.) Mackowiak, P. A. (1981) "Direct Effects of Hyperthermia on Pathogenic Microorganisms: Teologic Implications with Regard to Fever" [Review] Rev. Infect. Dis. 3(3):508-520.

160.) Li, G. C. et al (1992) "Heat Shock Protein hsp70 Protects Cells from Thermal Stress even After Deletion of its ATP-Binding Domain" Proc. Natl. Aca. Sci. USA 89(5):2036-2040.

161.) Mitsudomi, T. et al (1993) "Transformation by Viral Oncogenes Increased Sensitivity to Heat in Rat 3Y1 Fibroblasts" Anticancer Res. 13(4):995-999.

162.) Clocca, D. R. et al (1993) "Biological and Clinical Implications of Heat Shock Protein 27,000(Hsp27): a Review [Review] J. Natl. Cancer Instit. 85(19): 1558-1570.

163.) Faulus, J. A. et al (1993) "Heat Shock Protein Response in a Prostate Tumor Model to Interstitial Thermotherapy Implications for Clinical Treatment" Prostate 23(3):263-270.

164.) Trieb, K. et al (1994) "Hyperthermia Inhibits Proliferation and Stimulates the Expression of Differentiation Markers in Cultured Thyroid Carcinoma Cells" Cancer Lett. 87(1):65-71.

165.) Tauchi, K. et al (1991) "Expression of Heat Shock Protein in Human Breast Cancer: An Immunohistochemical Study" Jpn. J. Clin. Oncol. 21(4):256-263.

166.) Oleson, J. R. et al (1993) "Sensitivity of Hyperthermia Trial Outcomes to Temperature and Time: Implications for Thermal Goals of Treatment" Int. J. Radiat. Oncol. Biol. Phys. 25(2):289-297.

167.) Dickson, J. A. et al (1980) "Temperature Range and Selective Sensitivity of Tumors to Hyperthermia: A Critical Review" Ann. N>Y. Acad. Sci. 335:180-205.

168.) Meyer, J. L. et al (1989) "Hyperthermic Oncology: Current Biology, Physics and Clinical Results" [Review] Pharmacol. Ther. 42(2):251-288.

169.) Sapareto, S. A. (1987) :Thermal Isoeffect Dose: Addressing the Problem of Thermotolerance" Int. J. Hyperthermia 3(4):297-205.

170.) Field, S. B. et al (1983) "The Relationship Between Heating Time and Temperature: Its Relevance to Clinical Hyperthermia" Radiotherap., Oncol. 1(2):179-186.

171.) Armour, M. et al (1993) "A Sensitivity of Human Cells to Mild Hyperthermia" Cancer Res. 53(12):2740-2744.

172.) Amrani, M. et al (1996) "Kinetics of Induction and Protective Effect of Heat-Shock Proteins After Cardioplegic Arrest" Ann. Thorac. Surg. 61:1407-1412.

173.) Marber, M. S. et al (1993) "Cardiac Stress Protein Elevation 24 Hours After Brief Ischemic or Heat Stress is Associated with Resistance to Myocardial Infarction" Circ. 88:1264-1272.

174.) Hutter, M. M. et al (1994) "A Direct Correlation Between the Amount of Heat-Shock Protein Induced and the Degree of Myocardial Protection" Circ. 89:355-360.

175.) Donnelly, T. J. et al (1992) "Heat-Shock Protein Induction in Rat Hearts. A Role for Improved Myocardial Salvage After Ischemic and Reperfusion?" Circ. 85:769-778.

176.) Amrani, M. et al (1994) "Induction of Heat-Shock Proteins Enhances Myocardial and Endothelial Functional Recovery After Prolonged Cardio[legic Arrest" Ann. Thorac. Surg. 57:157-160.

177.) Liu, X. et al (1992) "Heat Shock: A New Approach for Myocardial Preservation in Cardiac Surgery" Circ. 86(suppl 2):358-363.

178.) Walker, D. M. et al (1993) "Heat Stress Limits Infarct Size in the Isolate Perfused Rabbit Heart Cardiovasc. Res. 27:962-967.

179.) Downing, J. F. et al (1987) "The Effect of in vivo Hyperthermia on Selected Lymphokines in Man" Lymphokine Res. 6:103-109.

180.) Englehardt, R. (1988) "Summary of Recent Clinical Experience in Whole-Body Hyperthermia Combined with Chemotherapy" In: Issels, R D Wilmanns, W. (eds) Application of Hyperthermia in the Treatment of Cancer pp 200-204.

181.) Aloia, R. C. et al (1988) "Lipid Composition and Fluidity of the Human Immunodeficiency Virus" Proc. Natl. Acad. Sci. 85:900-904.

182.) Hager, E. D. et al (1996) "Intraperitoneal Hyperthermic Perfusion (IPHP) Chemotherapy of Patients with Advanced Ovarian Cancer" Hyperthermic Oncol. Proc. 7th Int. Congress Hyperthermic Oncol. II:261.

183.) Robins, H. I. et al (1993) "Phase I Clinical Trials of Carboplatin and 41.8 degrees C. Whole-Body Hyperthermia in Cancer Patients" J. Oncol. 11(9):1787-1794.

184.) Schecterle, L. M. et al (1995) "Current and Future Prospects of Whole Body Hyperthermia for Deactivation of HIV" AIDS Patient Care 9(2):85-86.

185.) Zippel, D. et al (1996) "Continuous Hyperthermic Peritoneal Perfusion for Malignant Ascites and Irresectable-Intra_Abdominal Cancer" Hyperthermic Oncol. Proc. 7$^{th}$ Int. Congress Hyperthermia Oncol. 11:258-260.

186.) Schecterle, L. M. et al (1995) "Hyperthermia as a Potential Treatment in HIV Disease" Alternative Med. J. 2(3): 28-32.

187.) Schecterle, L. M. et al (1997) "Hyperthermia Alters HIV Kinetics" Alternative Therapies in Clinical Practice 4(5):162-164.

188.) Henry, K. et al (1996) "Acute Effects of Whole Body Hyperthermia (WBH) on Plasma HIV RNA Levels" Third Conf. On Retroviruses and Opportunistic Infections" Abstract #373.

189.) Schecterle, L. M. et al (1995) "Rate of Temperature Rise Using a Hot Air Whole Body Hyperthermia Device" Southern Med. J. 88(10):PS143.

190.) Schecterle, L. M. et al (In Press) "Twelve Month Follow-up in Advanced HIV Patients Treated with Whole Body Hyperthermia" 20$^{th}$ Int. Mtg. On Clinical Hyperthermia 191.) St. Cyr, J. A. et al (1996) "Cranial Venous Effluent Temperature Assessment During Extracorporeal Whole Body Hyperthermia" FASEB j. 10(3):A118.

192.) Schecterle, L. M. et al (1996) "Maintenance of Renal and Hepatic Function with Dopamine During and following Extracoporeal Whole Body Hyperthermia" SASEB j. 10(3):A119.

193.) Schecterle, L. M. et al (1996) "Alternative HIV Therapies" The Scientist 11(9):10.

194.) Kapp, D. (1982) 'Discussion: Hyperthermia and Drugs" NCI Monogr. 61:322.

195.) Martin, P. A. et al (1987) "Monitoring Body Site Temperature During Systemic Hyperthermia" Crit. Care Med. 15:163-164.

196.) Ohnoshi, t. et al (1985) "Combined Cytotoxicity Effect of Hyperthermia and Anthracycline Antibiotics on Human Tumor Cells" JNCI 74:275-281.

197.) Van der Zee, J. et al (187) "Whole Body Hyperthermia as a Treatment Modality" In: Fields, S. B., Hand, J. W. (eds) An Introduction to the Practical Aspects of Clinical Hyperthermia. Taylor and Francis, London pp 185-212.

198.) Thrall, D. E. et al (1990) "A Comparison of Temperature in Canine Solid Tumors During Local and Whole-Body Hyperthermia Administered Alone and Simultaneously" Int. J. Hyperthermia 6:305-317.

199.) Oleson, J. et al (1984) "Analysis of Prognostic Variables in Hyperthermia Treatment of 161 Patients" Int. J. Radiat. Oncol. Biol. Phys. 10:2231-2240.

200.) Ostrow, S. et al (1981) "Physiologic Response and Toxicity in Patients Undergoing Whole-Body Hyperthermia for the Treatment of Cancer" Cancer Treat. Rep. 65"323-325.

201.) Robins, H. I. et al (1986) "Interferon-alpha (IFN-alpha) and Whole Body Hyperthermia (WBH): a Phase I Trial" Am. Assoc. Cancer Res. 27:205.

202.) Schonbaum, E. et al (1990) "Thermoregulation Physiology and Biochemistry" Pergamon, New York, pp 1-506.

203.) Tamura, K. et al (1991) "High Pressure Antagonism of Alcohol Effects on the Main Phase-Transition Temperature of Phospholipid Membranes: Biphasic Response" Biochemica et Biophysica Acta, 1066, 219-224.

204.) Hayashi, H. et al (1998) "Temperature-Dependent Associating Property of Liposomes Modified with a Thermosensitive Polymer" Bioconjug. Chem. May-June: 9(3): 382-9.

205.) Liang, Chang-seng et al (1973) "Comparison of Cardiac Output Responses to 2,4 Dinitrophenol-Induced Hypermetabolism and Muscular Work" The Journal of Clinical Investigation, September, Volume 52: 2283-2292.

206.) Matsuda, T. (1996) "The Present Status of Hyperthermia in Japan" Ann. Acad. Med. Singapore, May; 25(3): 420-4.

207.) Ikeda, S. et al (1998) "Enhancement of the Effect of an Angiogenesis Inhibitor on Murine Tumors by Hyperthermia" Oncol. Rep., January-February; 5(1):181-4.

208.) Kakeya, H. (1997) "Heat Shock Protein of *Cryptococcus Neoformans* in Cryptococcosis" Abstr. Gen. Meet. Am. Soc. Microbiol., May 408; 97:271 (abstract no. F67).

209.) Multhoff, G. (1997) "Heat Shock Protein 72 (HSP72), a Hyperthermia-Inducible Immunogenic Determinant on Leukemic K562 and Ewing's Sarcoma Cells" Int. J. Hyperthermia, January-February; 13(1):39-48.

210.) Kato, H. et al (1998) "Research and Development of Hyperthermia Machines for Present and Future Clinical Needs" Int. J. Hyperthermia, Volume 14: No. 1; 1-11.

211.) Monti, M. et al (1986) "Microcalorimetric Investigation of Cell Metabolism in Tumour Cells from Patients with non-Hodgkin Lymphoma (NHL)" Scand. J. Haematol.; 36:353-357.

212.) Kallerhoff, M. et al (1996) "Microcalorimetric Measurements Carried out on Isolated Tumorous and Nontumorous Tissue Samples from Organs in the Urogenital Tract in Comparison to Histological and Impulse-Cytophotometric Investigations" Urol. Res.; 24:83-91.

213.) Alpard, S. K. et al (1996) "Therapeutic Hyperthermia" Perfusion 11:425-435.

214.) Bachmann, Barbara et al (1995) "Target Structures for HIV-1 Inactivation by Methylene Blue and Light" Journal of Medical Virology 47:172-178.

215.) Castedo, M. et al (1995) "Mitochondrial Perturbation Define Lymphocytes Undergoing Apoptotic Depletion in Vivo" Eur. J. Immunol. 25:3277-3284.

216.) Dryer, S. E. et al (1980) "Enhancement of Mitochondrial, Cyanide-Resistant Superoxide Dismutase in the Livers of Rats Treated with 2,4 Dinitrophenol" The Journal of Biol. Chem. 255(3):1054-1057.

217.) Gibellini, D. (1995) "Tat-expressing Jurkat Cells Shown an Increased Resistance to Different Apoptotic Stimuli, Including Acute Human Immunodeficiency Virus-type1 (HIV-1) Infection" British J. of Haema. 89:24-33.

218.) Ho, D. D. et al (1995) "Rapid Turnover of Plasma Virions and CD4 Lymphocytes in HIV-1 Infection" Nature 373:123-126.

219.) Macho, A. et al. (1995) "Mitochondrial Dysfunctions in Circulating T Lymphocytes from Human Immunodeficiency Virus-1 Carriers" Blood 86(7):2481-2487.

220.) Ornstein, M. H. et al "The Antiinflammatory and Antiviral Effects of Hydroxychloroquine in Two Patients with Acquired Immunodeficiency Syndrome and Active Inflammatory Arthritis" Arthritis and Rheumatism 39(1): 157-161.

221.) Owens, S. D. et al (1995) "Hyperthermic Therapy for HIV Infection" Medical Hypotheses 44:235-242.

222.) Pennypacker, C. et al (1995) "Localized or Systemic In Vivo Heat Inactivation of Human Immunodeficiency Virus (HIV): A Mathematical Analysis" Journal of Acquired Immune Deficiency Syndrome and Human Retrovirology 8:321-329.

223.) Perelson, A. S. et al (1994) "Does Hyperthermia Have a Therapeutic Role in HIV Disease" Science 271:1582-11586.

224.) Schecterle, L. M. et al (1994) "Does Hyperthermia Have a Therapeutic Role in HIV Disease" Research News, Journal of the Minn. Aca. Schience 58(2):27-30.

225.) Sweitzer-Thumann, C. et al (1994) "Effects of an Elevated Temperature on the Replication of HIV I in a Monocytic Cell Line" Res. Virol. 145:163-170.

226.) Somasundaran, M. et al (1994) "Localization of HIV RNA in Mitochondria of Infected Cells Potential Role in Cytopathogenicity" The Journal of Cell Biology 126(6): 1353-1360.

227.) Sperber, K. et al. (1993) "Inhibition of Human Immunodeficiency Virus Type I Replication by Hydroxychloroquine in T Cells and Monocytes" AIDS Research and Human Retroviruses 9(1): 91-98.

228.) Spire, B. et al. (1985) "Inactivation of Lymphadenopathy-Associated Virus by Heat, Gamma Rays, and Ultraviolet Light" The Lancet, January 26: 188-189.

229.) Steinhart, C. P., et al. (1996) "Effect of Whole-Body Hyperthermia on AIDS Patients with Karposi's Sarcoma: A Pilot Study" Journal of Acquired Immune Deficiency Syndrome and Human Retrovirology 11:271-281.

230.) Ursini, M. V. (1993) "Enhanced Activity of Human G6PD Promoter Transfected in HeLa Cells Producing High Levels of HIV-I Tat" Virology 196:338-343.

231.) Weatherbum, H. et al. (1990) "Joint Use of Hyperthermia and Chemotherapy in HIV Infection" International Journal of Immunopathology and Pharmacology 3(2):55-58.

232.) Westendorp, M. O. et al. (1995) "HIV-1 Tat Potentiates-induced TNF-κB Activation and Cytotoxicity by Altering the Cellular Redox State" The EMBO Journal 14(3):546-554.

233.) Yamauchi, N. (1992) "Mechanism of Synergistic Cytotoxic Effect Between Tumor Necrosis Factor and hyperthermia" Jpn. J. Cancer Res. 83:540-545.

234.) Yatvin, M. et al. (1995) "Whole Body Hyperthermia to Treat HIV Infection (Meeting Abstract)" $18^{th}$ International Symposium on Clinical Hyperthermia. p 12, Kiev, Ukraine.

235.) Flores, S. C. et al. (1996) "Alterations and Redox Status by the HIV-1 TAT Protein Affect Cellular Gene Expression and Function" Presentation, Oxidative and Redox Regulation Conference, Institut Pasteur, Paris, France.

236.) Chernin, E. (1984) "The Malariatherapy Of Neurosyphilis" J. Parasit. 70(5):611-617.

237.) Shvets, M. A. (1974) "Oxidative Phosphorylation in the Skeletal Muscles of Rabbits During Dinitrophenol Hyperthermia" Bulletin of Experimental Biol. And Medicine, 238.) de las Alas, V. et al (1990) "Oxygen Uptake and Mean Blood Pressure as Indicators of Induced Hyperthermia" J. Clinical Monitoring Volume 6(3):186-188.

239.) Scott. J. C. et al (1968) "Influence of 2,4-Dinitrophenol on Myocardial Metabolism in Hemodynamics" Metabolism 17:370-376.

240.) Levine. S. et al (1975) "Ventilatory Response to Drug-Induced Hypermetabolism" J. Appl. Physio. Volume 38(5):827-833.

241.) Tainter, M. L. (1934) "Dintrophenol in Diet, on Growth and Duration of Life of the White Rat" Proc. Soc. Exper. Biol. Med., 31:1161-1162

242.) Wood, D. A. et al (1934) "A Case of Fatal Dinitrophenol Poisoning" J.A.M.A. 102:1147.

243.) Bachynsky, N. (1987) "A Testing Program Using the Thermogenic drug 2,4-Dinitrophenol to save lives in Freezing Environments J. Environ. Sci. 30:50-56.

244.) Hoch, Frederic L. et al (1973) "Hyperthermia, Muscle Rigidity, and Uncoupling in Skeletal Muscle Mitochondria in Rats Treated with Halothane and 2,4-Dinitrophenol" Anesth. Volume 38(3):237-243.

245.) Takehiro, T. N. et al (1979) "Effects of 2,4-Dinitrophenol on the Body Temperature and Cardiopulmonary Functions in Unanaesthetized Rats" J. Therm. Biol. Volume 4: 297-301.

246.) Leutsker, R. J. et al (1935) "An Instance of Circulatory Collapse Attributed to Dinitrophenol' U.S. Navel Bulletin, Volume 33(2):394-395.

247.) Bachynsky, N. (1986) "A Reassessment of the Potential of 2,4-Dinitrophenol in Weight Reduction" $5^{th}$ Int. Conf. On Obesity Jerusalem, Israel.

248.) Schulte, T. L. et al (1934) "Chronic Toxicity of Dinitrophenol: Renal Function" Proc. Soc. Exper. Biol. Med., 31:1163.

249.) Blackburn, R. V. et al (1998) "Adenoviral-Mediated Transfer of a Heat-Inducible Double Suicide Gene into Prostate Carcinoma Cells" Cancer Res. 1; 58(7):1358-1362.

250.) Wierenga, P. K. et al (1998) "Enhanced Selectivity of Hyperthermic Purging of Human Progenitor Cells Using Goralatide, an Inhibitor of Cell Cycle Progression" Bone Marrow Transplant January; 21(1): 73-78.

251.) Osman, Yasser et al (1995) "Enhanced Elimination of Ph⁺ Chromosome Cells In Vitro by Combined Hyperthermia and other Drugs (AZT, IFN-α, TNF, and quercetin): Its application to Autologous Bone Marrow Transplantation for CML" Exp. Hema. 23:444-452.

252.) Carr, Andrew W. et al (1993) "Uncoupling of Rat Liver Mitochondrial Oxidative Phosphorylation by the Fasciolicide Triclabendazole and its Sulfoxide and Sulfone Metabolites" J. Parasitol., 79(2); 198-204.

253.) Tainter, M. L. et al (1932) "Actions of Dinitrophenol" Proc. Soc. Exper. Biol. Med. 29:1268-1275.

254.) Tainter, M. L. et al (1933) "Febrile, Respiratory and Some Other Actions of Dinitrophenol" J. Pharmacol. Exp. Therap., 48:410-418.

255.) Tainter, M. L. (1933) "Dinitrophenol as a Metabolic Stimulant" Bull. Calif. Dietetic Assoc., 1:3-6.

256.) Tainter, M. L. et al (1934) "A Case of Fatal Dinitrophenol Poisoning" J.A.M.A., 102:1147.

257.) Tainter, M. L. (1934) "Dinitrophenol in Diet, on Growth and Duration of Life of the White Rat" Proc. Soc. Exper. Biol. Med., 31:1161-1163.

258.) Tainter, M. L. et al (1935) "Metabolic Activity of Compounds Related to Dinitrophenol" J. Pharmacol. Exper. Ther., 53:58-62.

259.) Tainter, M. L. et al (1934) "Metabolic Response of White Rats to Continued Administration of Dinitrophenol" J. Pharmacol. Exper. Ther., 54:454-458.

260.) Tainter, M. L. (1938) "Growth, Life-Span and Food Intake of White Rats Fed Dinitrophenol Throughout Life" J. Pharm. Exp. Ther., 63, No. 1.

261.) Tainter, M. L. et al (1934) "Chronic Toxicity of Dinitrophenol: Renal Function" Proc. Soc. Exper. Biol. Med., 31:1163-1166.

262.) Tainter, M. L. et al (1935) "Dinitrophenol on Liver Function" Calif. and West. Med., 43: No. 5.

263.) Tainter, M. L. et al (1937) "Chronic Toxicity of Dinitrophenol: Functional and Morphological Changes in the Liver" J. Pharm. Exp. Ther., 59:419-423.

264.) Tainter, M. L. (1986) "Dinitrophenol: In Retrospect" Affidavit, Notarized by Marie J. Panella, Westchester County, N.Y., No. 60-4798577.

265.) Emge, L. A. et al (1933) "Effects of Dinitrophenol on an Experimental Sarcoma of the White Rat" Proc. Soc. Exper. Biol. Med., 31:152.

266.) Saiki, C. et al (1997) "Effect of 2,4-Dinitrophenol on the Hypometabolic Response to Hypoxia of Conscience Adult Rats" J. Appl. Physiol., 83(2):537-542.

267.) Williams, T. F. et al (1958) "Effects of 2,4-Dinitrophenol on Respiration in the Dog" Am. J. Physiol., 193(1): 181-188.

268.) Johannesen, J. et al (1977) "Renal Energy Metabolism and Sodium Reabsorption after 2,4-Dinitrophenol Administration" Am. J. Physiol., 233(3):F207-F212.

269.) Rognstad, R. et al (1969) "The Effect of 2,4-Dinitrophenol on Adipose-Tissue Metabolism" Biochem. J., 111: 431-444.

270.) Millhorn, D. E. et al (1982) "Effects of Salicylate and 2,4-Dinitrophenol on Respiration and Metabolism" J. Appl. Physiol., 53:925-929.

271.) Huch, A. D. et al (1969) "Oxygen Transport in Anesthetized Dogs in Hypoxia, with Oxygen Uptake Increased by 2,4-Dinitrophenol" Respir. Physiol., 6:187-201.

272.) Vollmer, R. T. et al (1999) "A prognostic score for hormone-refractory prostate cancer: analysis of two cancer and leukemia group B studies" Clin. Cancer Res., 5(4): 831-7.

273.) Vollmer, R. T. et al (1998) "The dynamics of prostate specific antigen in hormone refractory prostate carcinoma: an analysis of cancer and leukemia group B study 9181 of megestrol acetate" Cancer, 83(9):1989-94.

274.) Hawkins, R. A. et al (1998) "Apoptic Death of Pancreatic Cancer Cells Induced by Polyunsaturated Fatty Acids Varies with Double Bond Number and Involves an Oxidative Mechanism" J. of Pathology, 185:61-70.

275.) Marzo, A. et al (1999) "Tumor Antigens are Constitutively Presented in the Draining Lymph Nodes" J. of Immunology, 162:5838-5845.

276.) Asaumi, J. et al (1999) "Influence of Metabolic Inhibitors on the Intracellular Accumulation and Retention of Adriamycin" Anticancer Research, 19:615-618.

277.) Linsinger, G. et al (1999) "Uncouplers of Oxidative Phosphorylation Can Enhance a Fas Death Signal" Mol and Cell Biology, 19:3299-3311.

278.) Issekutz, Jr., B. (1984) "Effects of Propanolol in Dinitrophenol Poisoning" Arch. Int. Pharmacodyn., 272:310-319.

279.) Marcus, M. (1988) "The Regulation of Myocardial Perfusion in Health and Disease" Hospital Practice, July 15:203-230.

280.) U.S. Navy (1935) "Treatment of Obesity With Dinitrophenol" United States Naval Bulletin, XXXIII:238-243.

281.) Scythes, J. B., Jones, C. M. (1999) "Implications of the Recent Lyme Culture Technique for the Diagnosis of Syphilis" 12$^{th}$ International Conference on Lyme Disease and Other Spirochetal and Tick-Borne Disorders, New York, p. 58.

282.) Phillips, S. E., Mattman, L. H. et al (1998) "A Proposal for the Reliable Culture of Borrelia burgdorferi from Patients with Chronic Lyme Disease, Even from Those Previously Aggressively Treated" Infection 26:364-367.

283.) Flanagan, S. et al (1998) "Increased flux of free radicals in cells subjected to hyperthermia: detection by electron paramagnetic resonance spin trapping" FEBS 431:285-286.

284.) Kelly, P. J., Daumas-Duport C. et al (1987) "Imaging-based Stereotaxis Serial Biopsies in Untreated Intracranial Glial Neoplasms" J Neurosurg 66:865-874.

285.) Levivier, M., Goldman S. et al (1992) "Positron Emission Tomography-guided Stereotaxic Brain Biopsy" Neurosurgery 31:792-797

286.) Biaglow, J. et al (1998) "The Measurement Of Bioreductive Capacity Of Tumor Cells Using Methylene Blue" Int. J. Radiation Oncology Biol. Phys. 42:769-773.

287.) Sibille, B. et al (1998) "2,4 Dinitrophenol-Uncoupling Effect on $\Delta\Psi$ in Living Hepatocytes Depends on Reducing-Equivalent Supply" Cytometry 32:102-108.

288.) Jones, B. F. (1998) "A Reappraisal of the Use of Infrared Thermal Image Analysis in Medicine" IEEE Trans Med Imaging 17 (6):1019-27.

289.) Head, J. F. et al (1996) "Thermography. Its Relation to Pathologic Characteristics, Vascularity, Proliferation Rate, and Survival of Patients With Invasive Dutal Carcinoma of the Breast" Cancer 77 (7):1324-8.

290.) Head, J. F. et al (1993) "Breast Themography is a Noninvasive Prognostic Procedure That Predicts Tumor Growth Rate in Breast Cancer Patients" Ann N Y Acad Sci 698:153-8.

291.) Livertoux, M., Lagrange, P. et al (1996) "The Superoxide Production Mediated By The Redox Cycling Of Xenobiotics In Rat Brain Microsomes Is Dependent On Their Reduction Potential" Brain Research 725:207-216.

292.) Flanagan, S. et al (1998) "Increased Flux Of Free Radicals In Cells Subjected To Hyperthermia: Detection By Electron Paramagnetic Resonance Spin Trapping" FEBS 431:285-286.

293.) Daut, J., Elzinga, G. (1988) "Heat Production Of Quiescent Ventricular Trabeculae Isolated From Guinea-Pig Heart" Journal of Physiology 398:259-275.

294.) Yanase, M. et al (1998) "Intracellular Hyperthermia for Cancer Using Magnetite Cationic Liposomes An in vivo Study" Jpn. J. Cancer Res. 89:463-469.

295.) Brenner, B. et al (1995) "Altered Constitutive and Stress-Regulated Heat Shock Protein 27 Expression in HIV Type 1-Infected Cell Lines" AIDS Research and Human Retroviruses 11:713-717.

296.) Loven, D. P. et al (1988) "A Role for Reduced Oxygen Species in Heat Induced Cell Killing and the Induction of Thermotolerance" Medical Hypotheses 26:39-50.

297.) McHutchison, J. G. et al (1998) "Interferon Alfa-2b Alone Or In Combination With Ribavirin As Initial Treatment For Chronic Hepatitis C" NEJM 339:1485-1499.

298.) Bassett, D. J. P. et al (1976) "Stimulation of Rat Lung Metabolism With 2,4-dinitrophenol and Phenazine Methosulfate" American Journal of Physiology 231:898-902.

299.) Biaglow, J. E. et al (1998) "The Measurement Of Bioreductive Capacity Of Tumor Cells Using Methylene Blue" Int. J. Radiation Oncology Biol. Phys. 42:769-773.

300.) Lagrange, P et al (1994) "Superoxide Anion Production During Monoelectronic Reduction Of Xenobiotics By Preparations Of Rat Brain Cortex, Microvessels, And Choroid Plexus" Free Radical Biology & Medicine 17:355-359.

301.) Visarius, T. M. et al (1997) "Stimulation Of Respiration By Methylene Blue In Rat Liver Mitochondria" FEBS Letters 412:157-160.

302.) MacEwen, E. G. (1990) "Biologic Response Modifiers: The Future Of Cancer Therapy?" Vet Clin North Am Small Anim Pract 20:1055-73.

303.) Blachere, N. E. et al (1995) "Heat Shock Protein-Based Cancer Vaccines and Related Thoughts On Immunogenicity Of Humor Tumors" Cancer Biology 6:349-355.

304.) Tamura, Y. et al (1997) "Immunotherapy Of Tumors With Autologous Tumor-Derived Heat Shock Protein Preparations" Science 278:117-120.

305.) Jatoi, A. et al (1999) "The Prognostic Effect of Increased Resting Energy Expenditure Prior to Treatment for Lung Cancer" Lung Cancer 23:153-8.

306.) Nakanoma, T. et al (1998) "Anti-Proliferative Effects of Heating on the Human Prostatic Carcinoma Cells in Culture" Hum Cell 11(3): 167-74.

307.) (a) Barluenga, J. et al (1996) G. Chem. Commun. 1505-1506. (b) Arsequell, G. et al (1998) Tetrahedron Lett. (39): 7393-7396.

308.) Farina, V. et al (1999) J. Org. Chem., (59):5905-5911.

309.) Godfrey, I. M. et al (1974) J. Chem. Soc. Perkin Trans I, 1353-1356.

310.) Coon, C. L. (1973) J. Org. Chem. (38):4243-4248.

311.) Bacon, R. G. R. (1965) Quart. Rev. (19) 95.

312.) (a) Mitchell, T. N. et al (1992) Synthesis, 803-815. (b) Farina, V. (1996) Pure & Appl. Chem., (68), 73-78.

313.) (a) de Meijere, A. et al (1994) Angew. Chem. Int. Engl., (33):2379-2411. (b) Heck, R. F. (1982) Org. React., (27): 345-390.

314.) (a) Knochel, P. et al (1998) Tetrahedron, (54):8275-8319. (b) Knoehel, P. et al (1993) Chem. Rev., (93):2117-2188. (c) Erdick, E. (1992) Tetrahedron, (48):9577-9648. (d) Negishi, e.I. (1982) Acc. Chem. Res. (15):340-348.

315.) Miyaura, N. et al (1995) A. Chem. Rev. (95):2457-2483.

316.) Semmelhack, M. F. et al (1971) J. Am. Chem. Soc., (93):5980.

317.) Whitesides, G. M. et al (1969) J. Am. Chem. Soc., (91):4871-4882.

What is claimed is:

1. A method for inducing intracellular hyperthermia in a subject comprising the step of administering to a subject having an infection of *Borrelia burgdorferi, Mycobacterium leprae, Treponema pallidum*, HIV, hepatitis C, or herpes virus, an amount of 2,4-dinitrophenol sufficient to induce whole body intracellular hyperthermia in the subject, wherein the whole body intracellular hyperthermia is sufficient to treat the *Borrelia burgdorferi, Mycobacterium leprae, Treponema pallidum*, HIV, hepatitis C, or herpes virus infection in the subject.

2. The method of claim 1, wherein a second medication is administered, wherein the second medication increases the overall metabolic rate of the subject, or an increase in free radical flux.

3. The method of claim 1, wherein the induced intracellular hyperthermia involve the induction of heat shock proteins.

4. The method of claim 1 further comprising administering an anti-bacterial agent selected from the consisting of beta-lactam, macrolide, tetracycline, aminoglycoside, peptide antibiotic, sulfonamide, quinolone, nucleoside, oligosaccharide, polyene, nitrofuran, and a combination thereof.

5. The method of claim 1 further comprising administering an antiviral agent selected from the group consisting of amantadine, rimantadine, arildone, ribaviran, acyclovir, abacavir, vidarabine, 9-1,3-dihydroxy-2-propoxy methylguanine, ganciclovir, enviroxime, foscarnet, ampligen, podophyllotoxin, 2,3-dideoxytidine, iododeoxyuridine, trifluorothymidine, dideoxyMosine, d4T, 3TC, zidovudine, efavirenz, indinavir, saquinavir, ritonavir, nelfinavir, amprenavir, and a combination thereof.

6. A method for inducing intracellular hyperthermia in a subject comprising the step of administering to a subject having an infestation of *Sporothrix schenkii, Histoplasma, paracoccidiodes, Aspergillus, Leishmania*, malaria, *acanthamoeba*, or cestodes, an amount of 2,4-dinitrophenol sufficient to induce whole body intracellular hyperthermia in the subject, wherein the whole body intracellular hyperthermia is sufficient to treat the *Sporothrix schenkii, Histoplasma, Paracoccidiodes, Aspergillus, Leishmania*, malaria, *acanthamoeba* or cestodes infestation in the subject.

7. The method of claim 6 further comprising administering an antifungal agent selected from the group consisting of Amphotericin B, Griseofulvin, Fluconazole, Intraconazole, 5 fluoro-cytosine, Ketatoconazole and Miconazole.

8. The method of claim 6, wherein second medication is administered, wherein the second medication increases the overall metabolic rate of the subject, or causes an increase in free radical flux.

9. The method of claim 6, wherein the induced intracellular hyperthermia involve the induction of heat shock proteins.

* * * * *